US008877946B2

(12) United States Patent
Go et al.

(10) Patent No.: US 8,877,946 B2
(45) Date of Patent: Nov. 4, 2014

(54) BENZYLIDENE-INDOLINONE COMPOUNDS AND THEIR MEDICAL USE

(75) Inventors: Mei Lin Go, Singapore (SG); Han Kiat Ho, Singapore (SG); Xiao Chen, Singapore (SG)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 13/564,179

(22) Filed: Aug. 1, 2012

(65) Prior Publication Data

US 2013/0035364 A1 Feb. 7, 2013

Related U.S. Application Data

(60) Provisional application No. 61/514,950, filed on Aug. 4, 2011.

(51) Int. Cl.
*A61K 31/4015* (2006.01)
*A61K 31/404* (2006.01)
*C07D 209/34* (2006.01)
*C07D 209/40* (2006.01)

(52) U.S. Cl.
CPC ............ *A61K 31/404* (2013.01); *C07D 209/40* (2013.01); *C07D 209/34* (2013.01)
USPC ......................................... 548/483; 548/486

(58) Field of Classification Search
CPC . C07D 209/34; A61K 31/4015; A61K 31/404
USPC ................................. 548/483, 486
See application file for complete search history.

(56) References Cited

U.S. PATENT DOCUMENTS 6,147,106 A 11/2000 Tang et al. .................... 514/414

FOREIGN PATENT DOCUMENTS

WO    WO 96/40116           12/1996
WO    WO 2005/044817 A1     5/2005
WO    WO 2010/044753        4/2010

OTHER PUBLICATIONS

Lai, et al. Document No. 154:133035 retrieved from CAPLUS; Nov. 24, 2010.*
Lai, et al. Document No. 154:259396 retrieved from CAPLUS; Feb. 22, 2011.*
Tang, et al. Document No. 130:3771, retrieved from CAPLUS, Nov. 25, 1998.*
Liu, et al. Document No. 148:561720, retrieved from CAPLUS, May 16, 2008.*
Blake, et al. Document No. 80:26692, retrieved from CAPLUS, May 12, 1984.*
Chatten, et al. Document No. 78:118480, retrieved from CAPLUS, May 12, 1984.*
Zhou, et al. Document No. 149:448145, retrieved from CAPLUS, Jan. 18, 2008.*
T. Aboul-Fadl et al., "Schiff bases of indoline-2,3-dione (isatin) derivatives and nalidixic acid carbohydrazide, synthesis, antitubercular activity and pharmacophoric model building", European Journal of Medicinal Chemistry, vol. 45 (2010) pp. 4578-4586.
J. Azizian et al., "A Facile One-Pot Method for the Preparation of N-Alkyl Isatins Under Microwave Irradiation", Synthetic Communications, vol. 33, No. 5 (2003) pp. 789-793.
P. Diaz et al., "Design and Synthesis of a Novel Series of N-Alkyl Isatin Acylhydrazone Derivatives that Act as Selective Cannabinoid Receptor 2 Agonists for the Treatment of Neuropathic Pain", J. Med. Chem., vol. 51 (2008) pp. 4932-4947.
S. Garden et al., "A Convenient Methodology for the N-Alkylation of Isatin Compounds", Synthetic Communications, vol. 28, No. 9 (1998) pp. 1679-1689.
M. Sol Shmidt et al., "Simple and Efficient Microwave Assisted N-Alkylation of Isatin", Molecules, vol. 13, ISSN 1420-3049 (2008) pp. 831-840.
K. Ding et al., "Synthesis of spirooxindoles via asymmetric 1,3-dipolar cycloaddition", Science Direct, Tetrahedron Letters, vol. 46 (2005) pp. 5949-5951.
B. Pandit et al., "Structure-activity-relationship studies of conformationally restricted analogs of combretastatin A-4 derived from SU5416", Science Direct, Bioorganic & Medicinal Chemistry, vol. 14 (2006) pp. 6492-6501.
W. Zhang et al., "Functionalized 3-benzylidene-indolin-2-ones: Inducers of NAD(P)H-quinone oxidoreductase 1 (NQO1) with antiproliferative activity", Bioorganic & Medicinal Chemistry, vol. 17 (2009) pp. 2077-2090.
M. Konkel et al., "3-Arylimino-2-indolones Are Potent and Selective Galanin $GAL_3$ Receptor Antagonists", J. Med. Chem., vol. 49 (2006) pp. 3757-3758.
I. Cervena et al., "Fluorinated analogues of the tricyclic neuroleptics 2,3-Difluoro derivative of clorothepin", Eur. J. Med. Chem.—Chimica Therapeutica, vol. 15, No. 4, (1980) pp. 330-332.
B. Liégault et al., "Modulating Reactivity and Diverting Selectivity in Palladium-Catalyzed Heteroaromatic Direct Arylation Through the Use of a Chloride Activating/Blocking Group", J. Org. Chem., vol. 75 (2010) pp. 1047-1060.

* cited by examiner

*Primary Examiner* — Shawquia Young
(74) *Attorney, Agent, or Firm* — Klarquist Sparkman, LLP

(57) ABSTRACT

Compounds of general formula I:

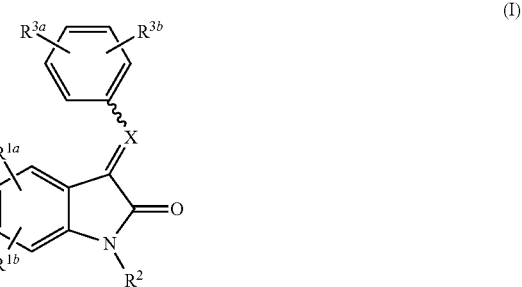

wherein
$R^{1a}$, $R^{1b}$, $R^2$, $R^{3a}$, $R^{3b}$ and X are as defined herein are tyrosine kinase inhibitors and are useful for the treatment of various diseases and conditions, for example cancer.

21 Claims, 3 Drawing Sheets

BENZYLIDENE-INDOLINONE COMPOUNDS AND THEIR MEDICAL USE

CROSS-REFERENCE TO RELATED APPLICATIONS

This application claims the benefit of priority of U.S. provisional application No. 61/514,950, file Aug. 4, 2011, the contents of the application being hereby incorporated by reference in its entirety.

FIELD OF THE INVENTION

The present invention relates to 3-benzylidene-indolin-2-one compounds and their use as inhibitors of tyrosine kinase. The invention also relates to methods of treating diseases or conditions associated with increased protein kinase activity, more particularly diseases and conditions which are related to increased tyrosine kinase activity. Such diseases and conditions include cell proliferative diseases such as cancer, atherosclerosis, arthritis and restenonsis and metabolic diseases such as diabetes.

BACKGROUND OF THE INVENTION

The use of tyrosine kinase inhibitors (TKIs) for treating diseases related to unregulated protein kinase, signal transduction have been subject to extensive research over the past two decades. For example, the use of indolinone compounds useful for the treatment of diseases including cell proliferative diseases such as cancer, atherosclerosis, arthritis and restenonsis and metabolic diseases such as diabetes was described in U.S. Pat. No. 6,147,106.

TKIs are generally important pharmacological agents in the growing field of targeted therapy against tyrosine kinase related diseases including cancers. Indeed, a number of tyrosine kinase inhibitors are currently available for the treatment of such conditions. These include sorafenib, gefitinib, elotinib and sunitinib, all of which are currently marketed for the treatment of various cancers. There remains a need, however, for potent broad spectrum tyrosine kinase inhibitors with directed efficacy against cancer.

WO96/40116 relates to indolin-2-ones having tyrosine kinase inhibitor activity. The indolinones are substituted at the 3-position with a benzylidene group.

Ding et al, *Tetrahedron Letters*, 46 (2005), 5949-5951 teaches compounds similar to those of WO96/40116 as intermediates in the synthesis of spirooxindoles.

Pandit et al, *Bioorg. Med. Chem.*, 14 (2006), 6492-6501 discloses anti-proliferative compounds which are similar to those of WO96/40116.

WO 2010/044753 and Zhang et al, *Bioorg. Med. Chem.* 17 (2009), 2077-2090 teach 3-benzylidene-indolin-2-one compounds which have activity as tyrosine kinase inhibitors. The present inventors have now developed further compounds which have similar activity but which have additional advantages over the compounds of WO 2010/044753.

SUMMARY OF THE INVENTION

The present invention relates to tyrosine kinase inhibitors of general formula (I)

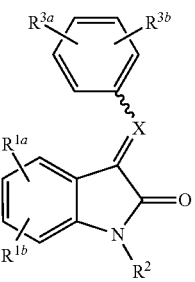

(I)

wherein
$R^{1a}$ is hydrogen, halo or —O($C_{1-6}$ alkyl);
$R^{1b}$ is hydrogen or, when $R^{1a}$ is halo, $R^{1b}$ may also be halo;
$R^2$ is hydrogen or $C_{1-6}$ alkyl;
$R^{3a}$ is hydrogen, halo, CN, $C_{1-4}$ alkyl, —O($C_{1-4}$ alkyl), $C_{1-4}$ haloalkyl, —O($C_{1-4}$ haloalkyl), $SO_2(C_{1-4}$ alkyl), $SO_2NR^{4a}R^{4b}$ or $NO_2$;
where each $R^{4a}$ and $R^{4b}$ is independently H or $C_{1-4}$ alkyl;
$R^{3b}$ is hydrogen or, when $R^{3a}$ is halo, $R^{3b}$ may also be halo;
X is CH or N;
or a pharmaceutically acceptable salt thereof;
provided that when $R^{1a}$ is fluoro, chloro or methoxy and $R^{1b}$ and $R^2$ are hydrogen, $R^{3a}$ is not 3'-methoxy or 3'-trifluoromethyl.

DETAILED DESCRIPTION OF THE INVENTION

Figure 1:
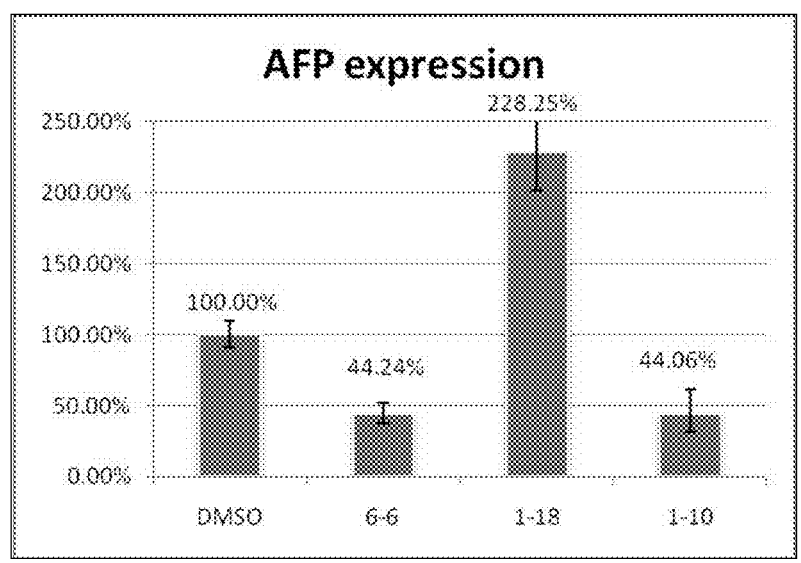
FIG. 1 is a plot showing the effect of Compounds 1-10, 1-18 and 6-6 on AFP mRNA transcription in HuH7 cells.

In a first aspect of the invention there is provided a compound of general formula (I)

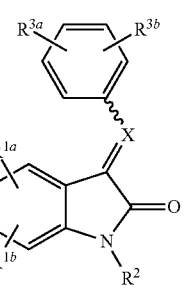

(I)

wherein
$R^{1a}$ is hydrogen, halo or —O($C_{1-6}$ alkyl);
$R^{1b}$ is hydrogen or, when $R^{1a}$ is halo, $R^{1b}$ may also be halo;
$R^2$ is hydrogen or $C_{1-6}$ alkyl;

$R^{3a}$ is hydrogen, halo, CN, $C_{1-4}$ alkyl, —O($C_{1-4}$ alkyl), $C_{1-4}$ haloalkyl, —O($C_{1-4}$ haloalkyl), $SO_2(C_{1-4}$ alkyl), $SO_2NR^{4a}R^{4b}$ or $NO_2$;
where each $R^{4a}$ and $R^{4b}$ is independently H or $C_{1-4}$ alkyl;
$R^{3b}$ is hydrogen or, when $R^{3a}$ is halo, $R^{3b}$ may also be halo;
X is CH or N;
or a pharmaceutically acceptable salt thereof;
provided that when $R^{1a}$ is fluoro, chloro or methoxy and $R^{1b}$ and $R^2$ are hydrogen, $R^{3a}$ is not 3'-methoxy or 3'-trifluoromethyl.

In the present invention, "$C_{1-6}$ alkyl" refers to a fully saturated straight or branched chain hydrocarbon group having from one to six carbon atoms. Examples of such alkyl groups include methyl, ethyl, isopropyl, n-propyl, n-butyl, isobutyl, t-butyl, n-pentyl and n-hexyl. "$C_{1-4}$ alkyl" and "$C_{1-2}$ alkyl" refer to alkyl groups having from 1-4 and 1-2 carbon atoms respectively.

The term "halo" refers to fluoro, chloro, bromo or iodo. More usually it refers to fluoro, chloro or bromo, especially fluoro or chloro.

The terms "$C_{1-6}$ haloalkyl" "$C_{1-4}$ haloalkyl" and "$C_{1-2}$ haloalkyl" refer respectively to alkyl groups having 1-6, 1-4 or 1-2 carbon atoms and substituted with at least one halo atom, particularly fluoro or chloro. More usually, a halo alkyl group will be substituted with more than one halo atom and may be up to perhalo-substituted. Examples include trifluoromethyl, 1,2-dichloro ethyl and 1,1,1,2,2-pentafluoroethyl. Trifluoromethyl is a particularly suitable example of a haloalkyl group.

As used herein, the term "pharmaceutically acceptable salt" refers to those salts which retain the biological effectiveness and properties of the parent compound. Such salts include, but are not restricted to: (1) an acid addition salt which is obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid or malonic acid and the like, preferably hydrochloric acid or (L)-malic acid; or (2) salts formed when an acidic proton present in the parent compound either is replaced by a metal ion, e.g., an alkali metal ion, such as sodium or potassium, an alkaline earth ion, such as magnesium or calcium, or an aluminium ion; or coordinates with an organic base such as ethanolamine, diethanolamine, triethanolamine, tromethamine, N-methylglucamine, and the like.

In one embodiment of the invention, compounds where $R^{1a}$ is fluoro, chloro or methoxy, $R^{1b}$ is hydrogen and $R^{3a}$ is 3'-methoxy or 3'-trifluoromethyl are also excluded.

The compounds of general formula (I) may be present as either the E-isomer or the Z-isomer or a mixture of both E- and Z-isomers.

In one embodiment, in compounds of general formula (I), $R^{1a}$ is hydrogen, fluoro, chloro or —O($C_{1-4}$ alkyl).

In more suitable compounds according to this embodiment:
$R^{1a}$ and $R^{1b}$ are both hydrogen; or
$R^{1a}$ is chloro, fluoro or —O($C_{1-4}$ alkyl) and $R^{1b}$ is hydrogen; or
$R^{1a}$ and $R^{1b}$ are each independently chloro or fluoro.

Still more suitably $R^{1a}$ and $R^{1b}$ are both hydrogen; or
$R^{1a}$ is chloro, fluoro or methoxy and $R^{1b}$ is hydrogen; or
$R^{1a}$ and $R^{1b}$ are both chloro; or
$R^{1a}$ and $R^{1b}$ are both fluoro.

In one embodiment, $R^{1b}$ is hydrogen and $R^{1a}$ is at the 5- or 6-position.

Particularly suitable compounds of this embodiment are those in which $R^{1a}$ is chloro, fluoro or methoxy, especially 5-chloro, 5-fluoro, 6-chloro, 6-fluoro or 6-methoxy.

In an alternative embodiment, $R^{1a}$ and $R^{1b}$ are both halo and are at the 4- and 5-positions or at the 5- and 6-positions. In particularly suitable compounds of this embodiment, $R^{1a}$ and $R^{1b}$ are 4,5-dichloro, 5,6-dichloro, 4,5-difluoro or 5,6-difluoro compounds. The difluoro compounds are particularly suitable.

In some suitable compounds of general formula (I), $R^2$ is hydrogen, methyl or ethyl, but particularly hydrogen or methyl. Compounds where $R^2$ is hydrogen are preferred.

In one embodiment of the invention, $R^{3a}$ is hydrogen, chloro, fluoro, CN, $C_{1-2}$ alkyl, —O($C_{1-2}$ alkyl), $C_{1-2}$ haloalkyl, —O($C_{1-2}$ haloalkyl), $SO_2$—($C_{1-4}$ alkyl), $SO_2NH_2$, $SO_2NH(C_{1-4}$ alkyl) or $SO_2N(C_{1-2}$ alkyl$)_2$ and $R^{3b}$ is hydrogen.

Suitably, $R^{3a}$ is hydrogen, chloro, fluoro, CN, methyl, methoxy, trifluoromethyl, trifluoromethoxy, $SO_2$—$CH_3$, $SO_2NH_2$, $SO_2NHCH_3$, $SO_2NH$(ethyl), $SO_2NH$(n-propyl), $SO_2NH$(isopropyl) or $SO_2N(CH_3)_2$ and $R^{3b}$ is hydrogen.

More suitably, $R^{3a}$ is hydrogen, chloro, fluoro, methyl, trifluoromethyl methoxy, trifluoromethoxy, $SO_2NH_2$, $SO_2NHCH_3$, $SO_2NH$(ethyl), $SO_2NH$(n-propyl), $SO_2NH$(isopropyl) or $SO_2N(CH_3)_2$ and $R^{3b}$ is hydrogen.

For example $R^{3a}$ may be trifluoromethyl, $SO_2NH(CH_3)$, $SO_2NH$(ethyl), $SO_2NH$(n-propyl), $SO_2NH$(isopropyl) or fluoro.

In this embodiment, $R^{3a}$ may be in the 2'-, 3'- or 4'position. However, more suitably, it is in the 2'- or 3'-position.

In one particularly suitable embodiment, $R^{3a}$ is $SO_2NH$(n-propyl), especially 3'-$SO_2NH$(n-propyl).

In the embodiment where $R^{3a}$ and $R^{3b}$ are both halo, they are suitably either chloro or fluoro and, although $R^{3a}$ and $R^{3b}$ may be different, they are usually the same. In particularly suitable compounds $R^{3a}$ and $R^{3b}$ are both fluoro. In compounds of this embodiment, $R^{3a}$ and $R^{3b}$ are suitably at the 3'- and 4'-positions.

In yet another embodiment of the invention, $R^{1a}$ is 6-chloro or 6-fluoro; $R^{1b}$ is H and either:
$R^{3b}$ is H and $R^{3a}$ is selected from the group consisting of hydrogen, 3'-halo, 4'-halo, 3'-$C_{1-4}$ alkyl, 4-trifluoromethyl, trifluoromethoxy, cyano or $SO_2(C_{1-4}$ alkyl), $SO_2NR^{4a}R^{4b}$; where each $R^{4a}$ and $R^{4b}$ is independently H or methyl; or
$R^{3a}$ is 3'-fluoro and $R^{3b}$ is 4-fluoro.

In this embodiment, a suitable example of halo is fluoro and the $C_{1-4}$ alkyl group is methyl.

In a further embodiment of the invention, $R^{1a}$ is 5-chloro or 5-fluoro; $R^{1b}$ is H and either:
$R^{3b}$ is H and $R^{3a}$ is selected from the group consisting of hydrogen, 3'-halo, 4'-halo $C_{1-4}$ alkyl, 4-trifluoromethyl, trifluoromethoxy, cyano or $SO_2(C_{1-4}$ alkyl), $SO_2NR^{4a}R^{4b}$; where each $R^{4a}$ and $R^{4b}$ is independently H or methyl; or
$R^{3a}$ is 3'-fluoro and $R^{3b}$ is 4-fluoro.

In this embodiment, a suitable example of halo is fluoro and the $C_{1-4}$ alkyl group is methyl.

In yet another embodiment of the invention, $R^{1a}$ is 6-methoxy; $R^{1b}$ is H and either:
$R^{3b}$ is H and $R^{3a}$ is selected from the group consisting of hydrogen, 2'-halo, 3'-halo, 4'-halo, $C_{1-4}$ alkyl, 2-trifluoromethyl, 4-trifluoromethyl, trifluoromethoxy, cyano or $SO_2(C_{1-4}$ alkyl), $SO_2NR^{4a}R^{4b}$; where each $R^{4a}$ and $R^{4b}$ is independently H or methyl; or
$R^{3a}$ is 3'-fluoro and $R^{3b}$ is 4-fluoro.

In this embodiment, a suitable example of halo is fluoro and the $C_{1-4}$ alkyl group is methyl.

In another embodiment of the invention, $R^{1a}$ and $R^{1b}$ are 4,5-difluoro, $R^{3b}$ is hydrogen and $R^{3a}$ is halo, 3'-trifluoromethyl, trifluoromethoxy cyano or $SO_2(C_{1-4}$ alkyl), $SO_2NR^{4a}R^{4b}$; where each $R^{4a}$ and $R^{4b}$ is independently H or methyl.

In this embodiment, a suitable example of halo is fluoro.

In another embodiment of the invention, $R^{1a}$ and $R^{1b}$ are 5,6-difluoro, $R^{3b}$ is hydrogen and $R^{3a}$ is 3'-halo, 3'-trifluoromethyl, 4'-trifluoromethyl, trifluoromethoxy cyano or $SO_2(C_{1-4}$ alkyl), $SO_2NR^{4a}R^{4b}$; where each $R^{4a}$ and $R^{4b}$ is independently H or methyl.

In this embodiment, a suitable example of halo is fluoro.

More suitable compounds of the invention are those in which X is CH.

Example compounds of the invention are (E)-3-Benzylidene-6-chloro-1,3-dihydro-indol-2-one (1-1);
(E)-6-Chloro-3-(2-fluoro-benzylidene)-1,3-dihydro-indol-2-one (1-2);
(E)-6-Chloro-3-(3-fluoro-benzylidene)-1,3-dihydro-indol-2-one (1-3);
(E)-6-Chloro-3-(4-fluoro-benzylidene)-1,3-dihydro-indol-2-one (1-4);
(E)-6-Chloro-3-(3-methyl-benzylidene)-1,3-dihydro-indol-2-one (1-5);
(E)-6-Chloro-3-(2-methoxy-benzylidene)-1,3-dihydro-indol-2-one (1-6);
(E)-6-Chloro-3-(3-methoxy-benzylidene)-1,3-dihydro-indol-2-one (1-7);
(E)-6-Chloro-3-(4-methoxy-benzylidene)-1,3-dihydro-indol-2-one (1-8);
(E)-6-Chloro-3-(2-trifluoromethyl-benzylidene)-1,3-dihydro-indol-2-one (1-9);
(E)-6-Chloro-3-(4-trifluoromethyl-benzylidene)-1,3-dihydro-indol-2-one (1-11);
(E)-6-Chloro-3-(3,4-difluoro-benzylidene) 1,3-dihydro-indol-2-one (1-12);
(E)-6-Chloro-3-(2-trifluoromethoxyl-benzylidene)indol-2-one (1-13);
(E)-6-Chloro-3-(3-trifluoromethoxyl-benzylidene)indol-2-one (1-14);
(E)-6-Chloro-3-(4-trifluoromethoxyl-benzylidene)indol-2-one (1-15);
(E)-6-Chloro-3-(3-methylsulfonyl-benzylidene)indol-2-one (1-16);
(E) 3-(6-Chloro-2-oxo-1,2-dihydro-indol-3-ylidenemethyl)-benzene-sulfonamide (1-17);
(E)-3-(6-Chloro-2-oxo-1,2-dihydro-indol-3-ylidenemethyl)-N-methyl-benzenesulfonamide (1-18);
(E) 3-(6-Chloro-2-oxo-1,2-dihydro-indol-3-ylidenemethyl)-benzonitrile (1-19)
(E)-3-(6-Chloro-2-oxo-1,2-dihydro-indol-3-ylidenemethyl)-N,N-dimethyl-benzenesulfonamide(1-20);
(E)-4-(6-Chloro-2-oxo-1,2-dihydro-indol-3-ylidenemethyl)-N-methyl-benzenesulfonamide (1-21);
(E)-3-(6-Chloro-2-oxo-1,2-dihydro-indol-3-ylidenemethyl)-N-ethyl-benzenesulfonamide (1-22)
(E/Z)-3-(6-Chloro-2-oxo-1,2-dihydro-indol-3-ylidenemethyl)-N-propyl-benzenesulfonamide (1-23)
(E/Z)-3-(6-Chloro-2-oxo-1,2-dihydro-indol-3-ylidenemethyl)-N-isopropyl-benzenesulfonamide (1-24)
(E)-3-Benzylidene-5-chloro-1,3-dihydro-indol-2-one (2-1);
(E)-5-Chloro-3-(2-fluorobenzylidene)indol-2-one (2-2);
(E)-5-Chloro-3-(3-fluorobenzylidene)indol-2-one (2-3);
(E)-5-Chloro-3-(4-fluorobenzylidene)indol-2-one (2-4);
(E)-5-Chloro-3-(3-methoxybenzylidene)indol-2-one (2-5);
(E)-5-Chloro-3-(2-trifluoromethylbenzyl idene)indol-2-one (2-6);
(E)-5-Chloro-3-(4-trifluoromethylbenzylidene)indol-2-one (2-8);
(E)-5-Chloro-3-(3,4-difluoro-benzylidene) 1,3-dihydro-indol-2-one (2-9);
(E)-5-Chloro-3-(3-trifluoromethoxyl-benzylidene)indol-2-one (2-10);
(E)-5-Chloro-3-(3-methanesulfonylbenzylidene)indol-2-one (2-11);
E/Z 3-(5-Chloro-2-oxo-1,2-dihydro-indol-3-ylidenemethyl)-benzenesulfonamide (2-12);
(E) 3-(5-Chloro-2-oxo-1,2-dihydro-indol-3-ylidenemethyl)-benzonitrile (2-13)
(E)-3-(5-Chloro-2-oxo-1,2-dihydro-indol-3-ylidenemethyl)-N-methyl-benzenesulphonamide (2-14);
(E)-3-Benzylidene-6-fluoroindol-2-one (3-1);
(E)-6-Fluoro-3-(2-fluorobenzylidene)indol-2-one (3-2);
(E)-6-Fluoro-3-(3-fluorobenzylidene)indol-2-one (3-3);
(E)-6-Fluoro-3-(4-fluorobenzylidene)indol-2-one (3-4);
(E)-6-Fluoro-3-(2-trifluoromethyl-benzylidene)indol-2-one (3-5);
(E)-6-Fluoro-3-(4-trifluoromethyl-benzylidene)indol-2-one (3-7);
(E)-6-Fluoro-3-(3-trifluoromethoxyl-benzylidene)indol-2-one (3-8)
(E)-6-Fluoro-3-(3-methanesulfonylbenzylidene)indol-2-one (3-9);
(E)-3-(6-Fluoro-2-oxo-1,2-dihydro-indol-3-ylidenemethyl)-N-methyl-benzenesulphonamide (3-10);
(E)-3-(6-Fluoro-2-oxo-1,2-dihydro-indol-3-ylidenemethyl)-N-ethyl-benzenesulfonamide (3-11)
E/Z-3-(6-Fluoro-2-oxo-1,2-dihydro-indol-3-ylidenemethyl)-N-propyl-benzenesulfonamide (3-12)
(E)-3-(6-Fluoro-2-oxo-1,2-dihydro-indol-3-ylidenemethyl)-N-isopropyl-benzenesulfonamide (3-13)
(E)-3-Benzylidene-5-fluoro-1,3-dihydro-indol-2-one (4-1);
(E)-5-Fluoro-3-(2-fluorobenzylidene)-1,3-dihydro-indol-2-one (4-2);
(E)-5-Fluoro-3-(3-fluorobenzylidene)-1,3-dihydro-indol-2-one (4-3);
(E)-5-Fluoro-3-(4-fluorobenzylidene)-1,3-dihydro-indol-2-one (4-4);
(E)-5-Fluoro-3-(2-methylbenzylidene)-1,3-dihydro-indol-2-one (4-5);
(E)-5-Fluoro-3-(3-methylbenzylidene)-1,3-dihydro-indol-2-one(4-6);
(E)-5-Fluoro-3-(4-methylbenzylidene)-1,3-dihydro-indol-2-one (4-7);
(E)-5-Fluoro-3-(3-methoxylbenzylidene)-1,3-dihydro-indol-2-one (4-8);
(E)-5-Fluoro-3-(2-trifluoromethyl)benzylidene)-1,3-dihydro-indol-2-one (4-9);
(E)-5-Fluoro-3-(4-trifluoromethylbenzylidene)-1,3-dihydro-indol-2-one (4-11);
(E)-5-Fluoro-3-(3,4-difluorobenzylidene)-1,3-dihydro-indol-2-one (4-12);
(E)-5-Fluoro-3-(3-trifluoromethoxyl-benzylidene)-1,3-dihydro-indol-2-one (4-13);
(E)-5-Fluoro-3-(3-methanesulfonylbenzylidene)-1,3-dihydro-indol-2-one (4-14);
(E) 3-(5-Fluoro-2-oxo-1,2-dihydro-indol-3-ylidenemethyl)-benzonitrile (4-15)
(E)-3-(5-Fluoro-2-oxo-1,2-dihydro-indol-3-ylidenemethyl)-N-methyl-benzenesulphonamide (4-16);

(E)-3-Benzylidene-6-methoxy-1,3-dihydro-indol-2-one (5-1);
(E)-3-(2-Fluoro-benzylidene)-6-methoxy-1,3-dihydro-indol-2-one (5-2);
(E)-3-(3-Fluoro-benzylidene)-6-methoxy-1,3-dihydro-indol-2-one (5-3);
(E)-3-(4-Fluoro-benzylidene)-6-methoxy-1,3-dihydro-indol-2-one (5-4);
(E)-6-Methoxy-3-(2-trifluoromethyl-benzylidene)-1,3-dihydro-indol-2-one (5-5);
(E)-6-Methoxy-3-(4-trifluoromethyl-benzylidene)-1,3-dihydro-indol-2-one (5-7);
(E)-3-(6-Methoxy-2-oxo-1,2-dihydro-indol-3-ylidenemethyl)-N-methyl-benzenesulphonamide (5-8);
(Z)-3-Benzylidene-4,5-difluoro-1,3-dihydro-indol-2-one (6-1);
(Z)-3-(2-Fluorobenzylidene)-4,5-difluoro-1,3-dihydro-indol-2-one (6-2);
(Z)-3-(3-Fluorobenzylidene)-4,5-difluoro-1,3-dihydro-indol-2-one (6-3);
(Z)-3-(4-Fluorobenzylidene)-4,5-difluoro-1,3-dihydro-indol-2-one (6-4);
E/Z-3-(2-Trifluoromethylbenzylidene)-4,5-difluoro-1,3-dihydro-indol-2-one (6-5);
(Z)-4,5-Difluoro-3-(3-trifluoromethyl-benzylidene)-1,3-dihydro-indol-2-one (6-6);
(Z)-4,5-Difluoro-3-(4-trifluoromethyl-benzylidene)-1,3-dihydro-indol-2-one (6-7);
(Z)-4,5-Difluoro-3-(3-trifluoromethoxyl-benzylidene)-1,3-dihydro-indol-2-one (6-8)
(E/Z)-4,5-Difluoro-3-(3-methanesulfonylbenzylidene)-1,3-dihydro-indol-2-one (6-9);
(Z)-3-(4,5-Difluoro-2-oxo-1,2-dihydro-indol-3-ylidenemethyl)-N-methyl-benzenesulphonamide (6-10);
(E)-3-Benzylidene-5,6-difluoro-1,3-dihydro-indol-2-one (7-1);
(E)-5,6-Difluoro-3-(2-fluorobenzylidene)-1,3-dihydro-indol-2-one (7-2);
(E)-5,6-Difluoro-3-(3-fluorobenzylidene)-1,3-dihydro-indol-2-one (7-3);
(E)-5,6-Difluoro-3-(4-fluorobenzylidene)-1,3-dihydro-indol-2-one (7-4);
(E)-5,6-Difluoro-3-(2-trifluoromethyl-benzylidene)-1,3-dihydro-indol-2-one (7-5);
(E)-5,6-Difluoro-3-(3-trifluoromethyl-benzylidene)-1,3-dihydro-indol-2-one (7-6)
(E)-5,6-Difluoro-3-(4-trifluoromethyl-benzylidene)-1,3-dihydro-indol-2-one (7-7);
(E)-5,6-Difluoro-3-(3-trifluoromethoxyl-benzylidene)-1,3-dihydro-indol-2-one (7-8)
(E)-5,6-Difluoro-3-(3-methanesulfonylbenzylidene)-1,3-dihydro-indol-2-one (7-9);
(E)-3-(5,6-Difluoro-2-oxo-1,2-dihydro-indol-3-ylidenemethyl)-N-ethyl-benzenesulfonamide (7-10)
(E) 3-(3-Trifluoromethyl-benzylidene)-1,3-dihydro-indol-2-one (8-1);
(E/Z) 3-(3-Trifluoromethyl-phenylimino)-1,3-dihydro-indol-2-one (8-2);
(E) 1-Methyl-3-(3-trifluoromethyl-benzylidene)-1,3-dihydro-indol-2-one (8-3);
(E/Z)) 6-Chloro-3-(3-trifluoromethyl-phenylimino)-1,3-dihydro-indol-2-one (8-4);
(E)-6-Chloro-1-methyl-3-(3-trifluoromethyl-benzylidene)-1,3-dihydro-indol-2-one (8-5);
(E/Z) 5-Chloro-3-(3-trifluoromethyl-phenylimino)-1,3-dihydro-indol-2-one (8-6);
(E/Z) 5-Fluoro-3-(3-trifluoromethyl-phenylimino)-1,3-dihydro-indol-2-one (8-7); or a pharmaceutically acceptable salt thereof.

Compounds of general formula (I) in which X is CH may be prepared by reacting a compound of general formula (II):

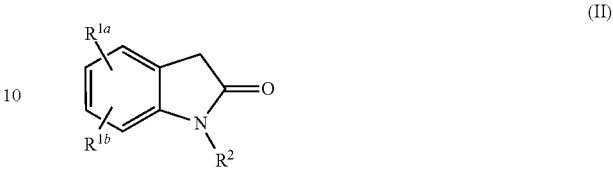

(II)

wherein $R^{1a}$, $R^{1b}$ and $R^2$ are as defined in general formula (I) with an aldehyde of general formula (III):

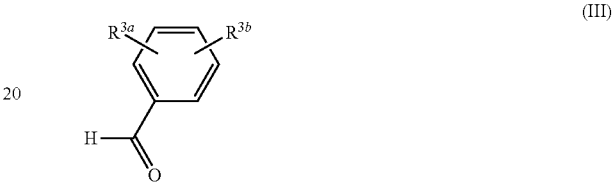

(III)

wherein $R^{3a}$ and $R^{3b}$ are as defined in general formula (I).

The reaction may be carried out in an alcoholic solvent such as ethanol and in the presence of a base, for example a cyclic amine such as piperidine or N-methylpiperidine. The reaction may be carried out in a sealed reaction vessel and at elevated temperature, for example about 100-160° C. This method forms a further aspect of the invention.

Many compounds of general formula (II) are readily available. Alternatively, compounds of general formula (II) can be prepared by methods well known to those of skill in the art. For example, a compound of general formula (II) may be prepared by reacting a compound of general formula (VI):

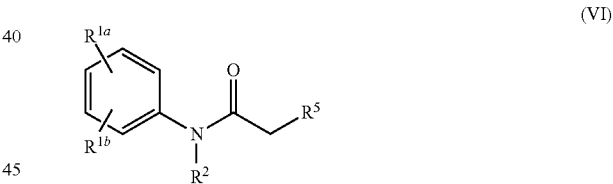

(VI)

wherein $R^{1a}$, $R^{1b}$ and $R^2$ are as defined in general formula (I) and $R^5$ is a leaving group, for example a halo atom such as chloro; with a Lewis acid such as aluminum chloride. The reaction may be conducted at elevated temperature, typically 180-230° C. This method represents a further aspect of the present invention.

A compound of general formula (VI) may be prepared by reacting a compound of general formula (VII):

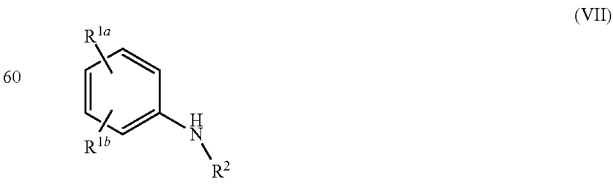

(VII)

wherein $R^{1a}R^{1b}$ and $R^2$ are as defined in general formula (I); with a compound of general formula (VIII):

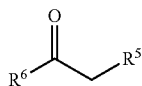
(VIII)

wherein each of R⁵ and R⁶ is a leaving group, for example a halo group such as chloro.

The reaction may be conducted in an organic solvent at a temperature of about 0-15° C.

Compounds of general formulae (VII) and (VIII) are readily available.

Compounds of general formula (II) in which $R^2$ is $C_{1-6}$ alkyl may also be prepared from compounds of general formula (II) in which $R^2$ is H by reacting with a base such as sodium hydride followed by reaction with a compound of formula (XIII):

(XIII)

wherein $R^2$ is $C_{1-6}$ alkyl.

The reaction may be conducted in a nonpolar organic solvent such as toluene, in an inert atmosphere, typically argon, and at elevated temperature, for example 80-120° C., more usually about 100° C.

Compounds of general formula (III) are also readily available in many cases. However, compounds of general formula (III) in which $R^{3a}$ is $SO_2NR^{4a}R^{4b}$ may be synthesised from compounds of general formula (IX):

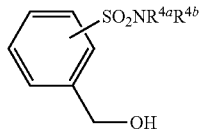
(IX)

wherein $R^{4a}$ and $R^{4b}$ are as defined above for general formula (I); by reaction with an oxidising agent. The oxidising agent should be chosen to be sufficiently mild to avoid oxidation to the benzoic acid derivative and an example of a suitable oxidising agent is a dichromate oxidising agent such as pyridinium dichromate. The reaction may be conducted in an anhydrous organic solvent such as tetrahydrofuran.

Compounds of general formula (IX) may be prepared from the corresponding benzoic acids of general formula (X):

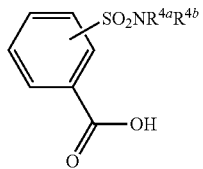
(X)

wherein $R^{4a}$ and $R^{4b}$ are as defined above for general formula (I); by reduction with a suitable reducing agent, for example a borane such as borane/tetrahydrofuran complex. The reaction may be carried out in an anhydrous organic solvent, typically tetrahydrofuran at a temperature of about 15 to 30° C., for example about 20-25° C.

Compounds of general formula (X) may be prepared from compounds of general formula (XI)

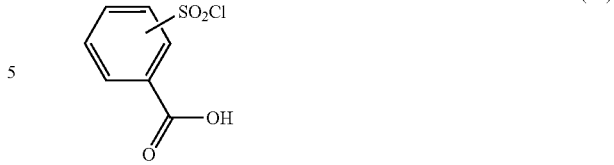
(XI)

by reaction with a compound of general formula (XII):

(XII)

wherein $R^{4a}$ and $R^{4b}$ are as defined above for general formula (I). A solution of the compound of general formula (XI) in an organic solvent such as ethyl acetate may be reaction may be stirred with an aqueous solution of the amine of general formula (XII) at a temperature of −5-5° C.

Compounds of general formula (I) in which $R^{3a}$ is $3\text{-}SO_2NR^{4a}R^{4b}$ are particularly suitable and in order to make these derivatives, the compound of general formula (XI) will be 3-chlorosulfonyl benzoic acid.

Compounds of general formula (I) in which X is N may be prepared by reacting a compound of general formula (IV):

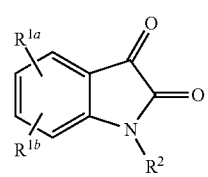
(IV)

wherein $R^{1a}$, $R^{1b}$ and $R^2$ are as defined in general formula (I); with an aniline derivative of general formula (V):

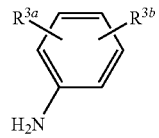
(V)

wherein $R^{3a}$ and $R^{3b}$ are as defined in general formula (I).

The reaction may be carried out by mixing the compounds of general formulae (IV) and (V) and heating in a sealed reaction vessel to a temperature of about 100-160° C.

Compounds of general formula (IV) and (V) are readily available or may be prepared by methods well known to those of skill in the art. For example methods for preparing compounds of general formula (IV) in which $R^2$ is $C_{1-6}$ alkyl are described by Azizian et al, *Synthetic Communications* 2003, 33, 789-793; Schmidt et al, *Molecules* 2008, 13, 831-840; Garden et al, *Synthetic Communications* 1998, 28, 1679-1689; Aboul-Fadl et al, *European Journal of Medicinal Chemistry* 2010, 45, 4578-4586; and Diaz et al, *Journal of Medicinal Chemistry* 2008, 51, 4932-4947.

Compounds of general formula (XII) are well known and are readily available.

Compounds of general formula (I) are tyrosine kinase inhibitors and are useful as medicaments and, in particular, medicaments for the treatment of diseases or conditions which are related to increased protein kinase activity, more particularly diseases and conditions which are related to increased tyrosine kinase activity. Such diseases and conditions include cell proliferative diseases such as cancer, atherosclerosis, arthritis and restenonsis and metabolic diseases such as diabetes. In a further aspect of the invention therefore, there is provided a method for the treatment or prevention of a disease or condition related to increased protein kinase activity, the method comprising administering to a patient in need of such treatment an effective amount of a compound of general formula (I) as defined above.

The patient may be any mammal but is more suitably a primate and in particular a human.

The invention also comprises a compound of general formula (I) for use in medicine, particularly in the treatment or prevention of a disease or condition related to increased protein kinase activity, for example cancer, atherosclerosis, arthritis, restenonsis or a metabolic disease such as diabetes.

Furthermore, the invention also comprises the use of a compound of general formula (I) in the preparation of an agent for the treatment or prevention of a disease or condition related to increased protein kinase activity, for example cancer, atherosclerosis, arthritis, restenonsis or a metabolic disease such as diabetes.

In particular, the invention relates to a method for the treatment or prevention of a disease or condition which is related to increased tyrosine kinase activity.

Examples diseases and disorders which may be treated in the method of the present invention are aberrant cell proliferative diseases, such as cancers, fibrotic and mesangial disorders, abnormal angiogenesis and vasculogenesis, wound healing, psoriasis, diabetes mellitus, and inflammation; aberrant differentiation conditions which include but are not limited to neurodegenerative disorders, slow wound healing rates and tissue grafting techniques; and aberrant cell survival conditions. Aberrant cell survival conditions relate to conditions in which programmed cell death (apoptosis) pathways are activated or abrogated. A number of protein kinases are associated with the apoptosis pathways. Aberrations in the function of any one of the protein kinases could lead to cell immortality or premature cell death. In some embodiments, the protein tyrosine kinase related disorders may include RTK-related disorders, for example an IGF-1R related disorder, an EphA2 related disorder or a Tyro3 related disorder. These disorders may be hepatocellular carcinoma, breast cancer, colon cancer and lung cancer.

The compounds of the present invention bind with high specificity and selectivity to protein tyrosine kinases, especially receptor tyrosine kinases (RTKs). Exemplary RTKs that may be bound by the compounds of the present invention are, without limitation, EGFR, HER2, HER3, HER4, IR, IGF-1R, IRR, PDGFR CSFIR, C-Kit, C-fms, Flk-1R, Flk4, KDR/Flk1, Flt-I, FGFR-1R, FGFR-2R, FGFR-3R, FGFR-4R, EphA1, EphA2, EphA3, EphA4, EphA5, EphA6, EphA7, EphA8, EphA10 and Tyro3. Upon binding, the compounds of the present invention reduce or abrogate protein tyrosine kinase-mediated cellular signaling. Without being bound to any particular theory, it is believed that the compounds of the invention will minimize and obliterate solid tumors by specifically inhibiting the activity of the tyrosine kinases, or will at least modulate or inhibit tumor growth and/or metastases. A precise understanding of the mechanism by which the compounds of the invention inhibit protein tyrosine kinase signalling is not required in order to practice the present invention. However, while not hereby bound to any particular mechanism or theory, it is believed that the compounds interact with amino acids of the protein tyrosine kinase in the ATP binding region or in close proximity thereto, through non-covalent interactions such as hydrogen bonding, Van de Waals interactions and ionic bonding. Therefore, this blocks the binding of ATP and thus the phosphorylation of other proteins. In this context, the specificity of the compounds of the present invention for a particular protein tyrosine kinase may be conferred by interactions between the constituents around the oxindole core of the compounds of the invention with the amino acid domains specific to individual protein tyrosine kinases. Thus, different indolinone substituents may contribute to preferential binding to particular protein tyrosine kinases.

The compound of general formula (I) will generally be administered to the patient in a pharmaceutical composition and therefore in a further aspect of the invention there is provided a pharmaceutical composition comprising a compound of general formula (I) as defined above and a pharmaceutically acceptable excipient.

The nature of the excipient will depend upon the chosen route of administration. The composition may be formulated for administration by any suitable route, for example oral, transdermal, buccal, nasal, sublingual or anal, or by a parenteral route such as intravenous or intramuscular injection.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatine, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used. Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatine, as well as soft, sealed capsules made of gelatine and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, or liquid polyethylene glycols. Stabilizers may be added in these formulations, also.

For transmucosal administration, penetrants appropriate to the barrier to be permeated are used in the formulation. Such penetrants are generally known in the art.

The compounds may also be formulated for parenteral administration, e.g., by bolus injection or continuous infusion. For injection, the compounds of the invention may be formulated in aqueous solutions, preferably in physiologically compatible buffers such as Hanks' solution, Ringer's solution, or physiological saline buffer. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound.

Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the formulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

A non-limiting example of a pharmaceutical carrier for the hydrophobic compounds of the invention is a cosolvent system comprising benzyl alcohol, a nonpolar surfactant, a water-miscible organic polymer and an aqueous phase such as the VPD co-solvent system. VPD is a solution of 3% w/v benzyl alcohol, 8% w/v of the nonpolar surfactant Polysorbate 80, and 65% w/v polyethylene glycol 300, made up to volume in absolute ethanol. The VPD co-solvent system (VPD: D5W) consists of VPD diluted 1:1 with a 5% dextrose in water solution. This cosolvent system dissolves hydrophobic compounds well, and itself produces low toxicity upon systemic administration.

Naturally, the proportions of such a co-solvent system may be varied considerably without destroying its solubility and toxicity characteristics. Furthermore, the identity of the co-solvent components may be varied: for example, other low toxicity nonpolar surfactants may be used instead of Polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. In addition, certain organic solvents such as dimethylsulfoxide also may be employed, although often at the cost of greater toxicity.

Additionally, the compounds may be delivered using a sustained-release system, such as semi permeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for stabilization may be employed.

The pharmaceutical compositions herein also may comprise suitable solid or gel phase carriers or excipients. Examples of such carriers or excipients include, but are not limited to, calcium carbonate, calcium phosphate, various sugars, starch, cellulose derivatives, gelatine, and polymers such as polyethylene glycols.

For any compound used in the methods of the invention, the therapeutically effective amount or dose can be estimated initially from cell culture assays. Then, the dosage can be formulated for use in animal models so as to achieve a circulating concentration range that includes the $IC_{50}$ as determined in cell culture (i.e., the concentration of the test compound which achieves a half-maximal inhibition of the protein tyrosine kinase activity). Such information can then be used to more accurately determine useful doses in humans.

Toxicity and therapeutic efficacy of the compounds described herein can be determined by standard pharmaceutical procedures in cell cultures or experimental animals, e.g., by determining the $IC_{50}$ and the $LD_{50}$ for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition.

Dosage amount and interval may be adjusted individually to provide plasma levels of the active species which are sufficient to maintain the protein tyrosine kinase inhibiting effects. These plasma levels are referred to as minimal effective concentrations (MECs). The MEC will vary for each compound but can be estimated from in vitro data, e.g., the concentration necessary to achieve 50-90% inhibition of a certain protein tyrosine kinase.

Dosages necessary to achieve the MEC will depend on individual characteristics and route of administration. HPLC assays or bioassays can be used to determine plasma concentrations.

Dosage intervals can also be determined using MEC value. In this context, compounds should be administered using a regimen that maintains plasma levels above the MEC for 10-90% of the time, preferably between 30-90% and most preferably between 50-90%.

In cases of local administration or selective uptake, the effective local concentration of the drug may not be related to plasma concentration and other procedures known in the art may be employed to determine the correct dosage amount and interval. The amount of a composition administered will, of course, be dependent on the subject being treated, the severity of the affliction, the manner of administration, the judgment of the prescribing physician, etc.

The compositions may, if desired, be presented in a pack or dispenser device, such as a kit approved by a regulatory authority, such as EMEA or FDA, which may contain one or more unit dosage forms containing the active ingredient. The pack may for example comprise metal or plastic foil, such as a blister pack. The pack or dispenser device may be accompanied by instructions for administration.

The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Compositions comprising a compound of the invention formulated in a compatible pharmaceutical carrier may also be prepared, placed in an appropriate container, and labeled for treatment of an indicated condition.

It is also an aspect of this invention that a compound described herein, or its salt or prodrug thereof, might be combined with one or more other agents for the treatment of the diseases and disorders discussed above. The one or more other agents may be combined with the compound of general formula (I) in a pharmaceutical composition of the invention or alternatively may be administered separately, simultaneously or sequentially with the compound of general formula (I).

Examples of other active ingredients that may be included in a pharmaceutical composition of the invention or may be co-administered with the compound of general formula (I) include, but are not limited to, a nucleic acid alkylator, a nucleoside analogue, an anthracycline, an antibiotic, an aromatase inhibitor, a folate antagonist, an estrogen receptor modulator, an inorganic aresenate, a microtubule inhibitor, a nitrosourea, an osteoclast inhibitor, a platinum containing compound, a retinoid, a topoisomerase 1 inhibitor, a topoisomerase 2 inhibitor, a thymidylate synthase inhibitor, an aromatase inhibitor, a cyclo-oxygenase inhibitor, an isoflavone, a tyrosine kinase inhibitor, a growth factor, a bisphosphonate, and a monoclonal antibody.

Alkylators that may be included in the pharmaceutical composition of the present invention include but are not limited to busulfan (Myleran®, Busilvex®), chlorambucil (Leukeran®), ifosfamide (Mitoxana®, with or without MESNA), cyclophosphamide (Cytoxan®, Neosar®), glufosfamide, melphalan/L-PAM (Alkeran®), dacarbazine (DTIC-Dome®), and temozolamide (Temodar®). As an illustrative example, the compound 2-bis[(2-chloroethyl)amino]tetrahydro-2H-1,3,2-oxazaphosphorine, 2-oxide, also commonly known as cyclophosphamide, is an alkylator used in the treatment of stages III and IV malignant lymphomas, multiple myeloma, leukemia, mycosis fungoides, neuroblastoma, ovarian adenocarcinoma, retinoblastoma, and carcinoma of the breast.

Nucleoside analogues that may be included in the pharmaceutical composition of the present invention include, but are not limited to, cytarabine (Cytosar®) and gemcitabine (Gemzar®), two fluorinated deoxycytidine analogues, fludarabine (Fludara®), a purine analog, 6-mercaptopurine (Puri-Nethol®) and its prodrug azathioprine (Imuran®).

Anthracyclines that may be included in the pharmaceutical composition of the present invention include, but are not limited to, doxorubicin (Adriamycin®, Doxil®, Rubex®), mitoxantrone (Novantrone®), idarubicin (Idamycin®), valrubicin (Valstar®), and epirubicin (Ellence®). As one example, the compound (8S,10S)-10-(4-amino-5-hydroxy-6-methyl-tetrahydro-2H-pyran-2-yloxy)-6,8,11-trihydroxy-8-(2-hydroxyacetyl)-1-methoxy-7,8,9,10-tetrahydrotetracene-5,12-dione, more commonly known as doxorubicin, is a cytotoxic anthracycline antibiotic isolated from cultures of *Streptomyces peucetius* var. *caesius*. Doxorubicin has been used successfully to produce regression in disseminated neoplastic conditions such as acute lymphoblastic leukemia, acute myeloblastic leukemia, Wilm's tumour, neuroblastoma, soft tissue and bone sarcomas, breast carcinoma, ovarian carcinoma, transitional cell bladder carcinoma, thyroid carcinoma, lymphomas of both Hodgkin and non-Hodgkin types, bronchogenic carcinoma, and gastric carcinoma.

Antibiotics that may be included in the pharmaceutical composition of the present invention include but are not limited to dactinomycin, actinomycin D (Cosmegen®), daunorubicin/daunomycin (Cerubidine®, DanuoXome®), bleomycin (Blenoxane®), epirubicin (Pharmorubicin®) and mitoxantrone (Novantrone®). Aromatase inhibitors useful in the practice of the present invention include but are not limited to anastrozole (Arimidex®) and Ietroazole (Femara®). Bisphosphonate inhibitors that may be included in the pharmaceutical composition of the present invention include but are not limited to zoledronate (Zometa®).

Cyclooxygenase inhibitors that may be included in the pharmaceutical composition of the present invention include but are not limited to acetylsalicylic acid (Aspirin®), celecoxib (Celebrex®) and rofecoxib (Vioxx®, Ceoxx®, Ceeoxx®). Estrogen receptor modulators that may be included in the composition of the present invention include but are not limited to tamoxifen (Nolvadex®) and fulvestrant (Faslodex®). Folate antagonists that may be included in the composition of the present invention include but are not limited to methotrexate (Trexall®, Rheumatrex®) and trimetrexate (Neutrexin®). As an illustrative example, the compound (S)-2-(4-(((2,4-diaminopteridin-6-yl)methyl)methylamino)benzamido)-pentanedioic acid, commonly known as methotrexate, is an antifolate drug that has been used in the treatment of gestational choriocarcinoma and in the treatment of patients with chorioadenoma destruens and hydatiform mole. It is also useful in the treatment of advanced stages of malignant lymphoma and in the treatment of advanced cases of mycosis fungoides.

Inorganic arsenates that may be included in the pharmaceutical composition of the present invention include but are not limited to arsenic trioxide (Trisenox®). Microtubule inhibitors (as used herein, a "microtubule inhibitor" is any agent that interferes with the assembly or disassembly of microtubules) that may be included in the composition of the present invention include but are not limited to vincristine (Oncovin®), vinblastine (Velban®), paclitaxel (Taxol®, Paxene®), vinorelbine (Navelbine®), docetaxel (Taxotere®), epothilone B or D or a derivative of either, and discodermolide or its derivatives.

Nitrosoureas that may be included in the pharmaceutical composition of the present invention include but are not limited to procarbazine (Matulane®), lomustine (CeeNU®), carmustine (BCNU®, BiCNU®, Gliadel Wafer®), and estramustine (Emcyt®). Nucleoside analogs that may be included in the pharmaceutical composition of the present invention include but are not limited to 6-mercaptopurine (Purinethol®), 5-fluorouracil (Adrucil®), 6-thioguanine (Thioguanine®), hydroxyurea (Hydrea®), cytarabine (Cytosar-U®, DepoCyt®), floxuridine (FUDR®), fludarabine (Fludara®), pentostatin (Nipent®), cladribine (Leustatin®, 2-CdA®), gemcitabine (Gemzar®), and capecitabine (Xeloda®). As an illustrative example, the compound 5-fluoro-2,4(1H,3H)-pyrimidinedione, also commonly known as 5-fluorouracil, is an antimetabolite nucleoside analogue effective in the palliative management of carcinoma of the colon, rectum, breast, stomach, and pancreas in patients who are considered incurable by surgical or other means. Another example of a nucleoside analogue is Gemcitabine. Gemcitabine is 2'-deoxy-2',2'-difluoro-cytidine. It is commercially available as the monohydrochloride salt, and as the betaisomer. It is also known chemically as 1-(4-amino-2-oxo-1-H-pyrimidin-1-yl)-2-desoxy-2,2-difluororibose.

An illustrative example of an osteoclast inhibitor that may be included in the pharmaceutical composition of the present invention is pamidronate (Aredia®). Platinum compounds that may be included in the pharmaceutical composition of the present invention include, but are not limited to, cisplatin (Platinol®) and carboplatin (Paraplatin®). Retinoids that may be included in the pharmaceutical composition of the present invention include but are not limited to tretinoin, ATRA (Vesanoid®), alitretinoin (Panretin®), and bexarotene (Targretin®). Topoisomerase 1 inhibitors that may be included in the pharmaceutical composition of the present invention include, but are not limited to, topotecan (Hycamtin®) and irinotecan (Camptostar®, Camptothecan-11®). Topoisomerase 2 inhibitors that may be included in the pharmaceutical composition of the present invention include, but are not limited to, etoposide (Etopophos®, Vepesid®) and teniposide (Vumon®).

Examples of other suitable tyrosine kinase inhibitors that may be included in the pharmaceutical composition of the present invention include, but are not limited to, dasatinib (Sprycel®), erlotinib (Tarceva®), gefitinib (Iressa®), imatinib (Gleevec®), lapatinib (Tykerb®), sorafenib (Nexavar®) and vandetanib (Zactima®). Examples of a (recombinant) growth factor that may be included in the pharmaceutical composition of the present invention include, but are not limited to, interleukin-11, interferon-α-2b and interleukin-2. An illustrative example of a thymidylate synthase inhinitor that may be included in the pharmaceutical composition of the present invention is Raltitrexed®. Examples of a monoclonal antibody that may be included in the pharmaceutical composition of the present invention include, but are not limited to, rituximab (MabThera®) or cetuximab (Erbitux®).

The invention will now be described in greater detail with reference to the Examples.

Example 1

General Methods for Synthesis

The reacting oxindoles (except 5,6-difluoroxindole) and benzaldehydes (except 3-formyl- and 3-formyl-N-methylbenzenesulfonamides), isatins and 3-(trifluoromethyl)aniline were obtained from commercial suppliers (Aldrich, Alfa-Aeasar, and TCI) and used as received. Other reagents were of synthetic grade or better and were used without further purification.

Microwave reactions were carried out on the Biotage Initiator® Microwave Synthesizer (Power: 100-150 W at 2.45 GHz, Pressure: 15-20 bar). Merck silica 60 F254 sheets and Merck silica gel (0.040-0.063 mm) were used for thin layer chromatography (TLC) and flash chromatography respectively. $^1$H NMR spectra (300 MHz or 400 MHz) were determined on a Bruker DPX 300 spectrometer and Bruker ADVIII 400 spectrometer and peaks were referenced to residual d-chloroform (δ 7.260) or $d_6$-DMSO (δ 2.500) as internal standards. $^{13}$C NMR spectra (75 MHz or 100 MHz) were determined on the same instruments and reported in ppm (δ) relative to residual DMSO (δ 39.43). Coupling constants (J) were reported in hertz (Hz). Proton ($^1$H) NMR spectral information is tabulated in the following format: multiplicity, coupling constant, number of protons. Multiplicities are reported as follows: s=singlet, d=doublet, t=triplet, q=quartet, dd=doublet of doublets, td=doublet of triplet, m=multiplet. Mass spectrum was captured on a Sciex API 3000 Qtrap (Applied Biosystems) equipped with a chemical ionization (APCI) probe and m/z values for the molecular ion was reported. Purity of final compounds was verified by HPLC, using two different solvent systems and found to have ≥95% purity, unless indicated otherwise.

Chromatographic separations were carried out on a Hewlett Packard HPLC column (200×4.6 mm, 10 μm, C18 reversed phase). The optimized mobile phase was an isocratic solution of 40% of water and 60% of acetonitrile. The mobile phase flow rate was 1.0 mL/min.

Compounds 1-23, 1-24, and 3-12 existed as a mixture of E and Z isomers, which were confirmed by LC-MS using Shimadzu LC 20 2D series HPLC couple to AB Sciex Instruments 3200 Q TRAP LC/MS/MS with Electrospray ionization (ESI) probe. Chromatographic separations were carried out on an Poroshell 120 EC-C18 column (150×4.6 mm, 2.7 Å). The optimized mobiled phase was an isocratic solution of 25% of water and 75% of acetonitrile. The mobile phase flow rate was 0.3 ml/min. multiple reaction monitoring (MRM) were performed using negative ESI ionization mode. The optimized source and compound dependent MS parameter were show in Table 1-1 and 1-2.

TABLE 1-1

Optimized source dependent MS parameter

| Curtain gas (psi) | Temperature (deg C.) | Ion gas 1 (psi) | Ion gas 2 (psi) |
|---|---|---|---|
| 10 | 350 | 20 | 20 |

TABLE 1-2

Optimized compound dependent MS parameter

| Cpd | Precursor Ion Mass (amu) | Product Ion Mass (amu) | Dwell Time (msec) | De-clustering Potential (V) | Entrance Potential (V) | Collision Cell Entrance Potential (V) | Collision Energy (eV) | Collision Cell Exit Potential (V) |
|---|---|---|---|---|---|---|---|---|
| 1-23 | 375.3 | 253.0 | 200.00 | −71 | −8 | −38 | −40 | −2 |
| 1-24 | 375.1 | 253.0 | | −58 | −5 | −24 | −48 | −3 |
| 3-12 | 359.1 | 237.1 | | −58 | −5 | −37 | −44 | −2 |

General Procedure for the Synthesis of 3-benzylidene indolin-2-ones of Series 1 to 8

The method described by Zhang et al.[1] was followed. Briefly, oxindole (1 mmol) and benzaldehyde (1 mmol) were dissolved in ethanol (6 mL), a drop of piperidine (20 μL) was added and the reaction mixture was heated in a sealed 10 mL vial on the microwave synthesizer for 15 minutes at 140 deg C. The mixture was then cooled to room temperature on an ice bath. If precipitation was observed, the precipitate was removed by filtration under reduced pressure, washed with cold ethanol and recrystallized with acetonitrile to afford the desired product. If no precipitation was observed, the mixture was then concentrated under reduced pressure and the residue was purified by flash column chromatography with hexane-ethyl acetate. Composition of the eluting system was determined by carrying out TLC.

General Procedure for the Synthesis of 3-arylimino-2-indolones of Series 8

The method described by Konkel et al.[2] was followed with some modification. Briefly, a mixture of isatin (3 mmol) and 3-(trifluoromethyl)aniline (15 mmol) was heated in a sealed 10 mL vial on the microwave synthesizer for 15 minutes at 140 deg C. Upon cooling, the product was filtered and washed with cold methanol, giving the desired product as an orange or red solid.

Synthesis of 5,6-difluoro-oxindole

The method of Cervena et al.[3] was followed. To a stirred solution of 3,4-difluoroaniline (10 mmol) in toluene (5 mL) and pyridine (10 mmol) maintained at 5-10 deg C was added chloroacetyl chloride (10 mmol) in toluene (5 mL) dropwise. The mixture was allowed to stand overnight at room temperature. The organic layer was then separated and the residue was mixed with water (60 mL). The separated solid product was recrystallized from toluene to give N-(3,4-difluorophenyl)chloroacetamide (8.6 g, 84.3% yield). $^1$HNMR (300 MHz, CDCl$_3$) δ 8.24 (s, 1H, NH), 7.63 (td, J=8.1 Hz, 1H, Ar—H), 7.16-7.12 (m, 2H, Ar—H), 4.19 (s, 2H, COCH$_2$Cl).

A mixture of N-(3,4-difluorophenyl)chloroacetamide (14 mmol) and aluminum chloride (54 mmol) was stirred and heated to 200-210 deg C. in a silicon oil bath for 4.5 h. On cooling, 40 mL of ice cold hydrochloric acid was added to the reaction mixture. The solid residue was removed by vacuum filtration and purified by column chromatography with hexane-ethyl acetate (1:1) as eluting solvent. The yield for this step was 40.7%. $^1$HNMR (300 MHz, in DMSO-d$_6$) δ 10.46 (s, 1H, NH), 7.33 (t, J=8.7 Hz, 1H, Ar—H), 6.82 (q, J=6.9 Hz, 1H, Ar—H), 3.47 (s, 2H, ArCH$_2$CO).

Synthesis of 1-methyl-oxindole and 6-chloro-1-methyl-oxindole

The method of Liégault et al.[4] was followed. A suspension of sodium hydride (2 mmol, 60% dispersion in mineral oil) in toluene (4 mL) was heated to 100 deg C. in an atmosphere of argon. A solution of the oxindole (2 mmol) in toluene was added to the stirred mixture and stirring was continued for 1 h at 100 deg C. Neat dimethylsulphate (2 mmol) was added dropwise and the mixture was stirred for 2 h at 100 deg C. On cooling, the mixture was thoroughly washed with distilled water and the aqueous phase was extracted with ethyl acetate. The organic phase was dried with anhydrous Na$_2$SO$_4$, concentrated under reduced pressure and purified by column chromatography with hexane-ethyl acetate (3:1) as eluting solvent.

1-Methyl-oxindole, white solid, yield 45.2%, $^1$HNMR (300 MHz, in DMSO-d$_6$) δ 7.27 (t, J=7.8 Hz, J=7.5 Hz, 2H, Ar—H), 6.98 (q, J=15.8, 2H, Ar—H), 3.53 (s, 2H, ArCH$_2$CO), 3.11 (s, 3H, N-Me).

6-Chloro-1-methyl-oxindole, light pink solid, yield 76.7%, $^1$HNMR (300 MHz, in DMSO-d$_6$) δ 7.24 (d, J=7.8 Hz, 1H, Ar—H), 7.10 (s, 1H, Ar—H), 7.05 (d, J=7.8 Hz, 1H, Ar—H), 3.54 (s, 2H, ArCH$_2$CO), 3.11 (s, 3H, N-Me)

Synthesis of Sulfamoyl Benzoic Acids and Formyl Benzenesulfonamides

The method of Shen et al.[4] was followed with some modifications. To a saturated solution of 3-chloro sulfonyl benzoic acid (8 mmol) in ethyl acetate (4 mL) was added cold concentrated ammonia or methylamine aqueous solution. After stirring for 30 min at 0 deg C., the mixture was neutralized with a solution of HCl in dioxane (4M) and extracted with ethyl acetate. The organic phase was concentrated under reduced pressure to give a solid which was recrystallized from acetonitrile to give desired compound.

3-Sulfamoyl-benzoic Acid

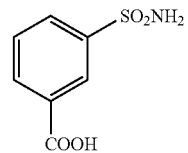 [SMILES: NS(=O)(=O)c1cccc(C(=O)O)c1]

White solid, yield 64.6%, $^1$HNMR (300 MHz, DMSO-d$_6$) δ 8.38 (s, 1H, Ar—H), 8.12 (d, J=8.1 Hz, 1H, Ar—H), 8.03 (d, J=7.8 Hz, 1H, Ar—H), 7.71 (t, J=7.5 Hz, J=7.8 Hz, 1H, Ar—H), 7.5 (s, 2H, SO$_2$NH$_2$)

3-Methylsulfamoyl-benzoic Acid

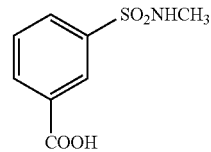

white solid, yield 54%, $^1$HNMR (300 MHz, DMSO-d$_6$) δ 8.30 (s, 1H, Ar—H), 8.17 (d, J=7.8 Hz, 1H, Ar—H), 7.99 (d, J=8.1 Hz, 1H, Ar—H), 7.75 (t, J=7.8 Hz, 1H, Ar—H), 7.62 (d, J=4.8 Hz, 1H, NH), 2.4 (s, 3H, Me).

4-Methylsulfamoyl-benzoic Acid

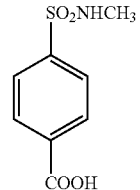

White solid, yield 59.0%, $^1$H NMR (400 MHz, DMSO-d$_6$), δ 8.17-8.08 (m, 2H, Ar—H), 7.92-7.84 (m, 2H, Ar—H), 7.64 (dd, J=9.9, 4.9 Hz, 1H, NH), 2.43 (d, J=5.0 Hz, 3H, Me).

3-Dimethylsulfamoyl-benzoic Acid

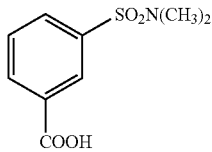

White solid, yield 90.6%, $^1$H NMR (400 MHz, DMSO-$d_6$) δ 8.22 (ddd, J=14.1, 1.4 Hz, 2H, Ar—H), 8.03-7.90 (m, 1H, Ar—H), 7.79 (t, J=7.8 Hz, 1H, Ar—H), 2.63 (s, 6H, Me).

3-Ethylsulfamoyl-benzoic Acid

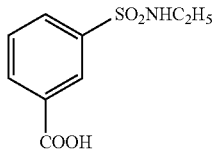

White solid, yield 68.1%, $^1$H NMR (400 MHz, DMSO-$d_6$), δ 8.32 (t, J=1.6 Hz, 1H, NH), 8.20-8.12 (m, 1H, Ar—H), 8.06-7.96 (m, 1H, Ar—H), 7.73 (dd, J=15.1, 6.9 Hz, 2H, Ar—H), 2.78 (dq, J=7.2, 5.8 Hz, 2H, CH$_2$), 0.96 (t, J=7.2 Hz, 3H, Me).

3-Propylsulfamoyl-benzoic Acid

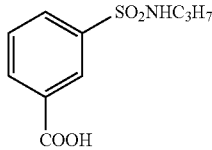

White solid, yield 53.1%, $^1$H NMR (400 MHz, DMSO-$d_6$), δ 8.31 (t, J=1.59 Hz, 1H, NH), 8.19-8.13 (m, 1H), 8.00 (ddd, J=7.83, 1.87, 1.16 Hz, 1H, Ar—H), 7.80-7.69 (m, 2H, Ar—H), 2.69 (dd, J=12.95, 6.99 Hz, 2H, N—CH$_2$), 1.42-1.28 (m, 2H, CH$_2$), 0.77 (t, J=7.39 Hz, 3H, Me).

3-Isopropylsulfamoyl-benzoic Acid

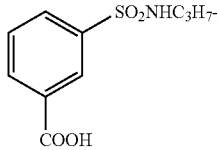

White solid, yield 38.5%, $^1$H NMR (400 MHz, DMSO-$d_6$), δ ppm 8.19-8.12 (m, 1H, N—H), 8.34 (t, J=1.6 Hz, 1H, Ar—H), 8.03 (ddd, J=7.8, 1.8, 1.2 Hz, 1H, Ar—H), 7.79-7.67 (m, 2H, Ar—H), 3.24 (ddd, J=25.0, 12.5, 6.1 Hz, 1H, N—CH), 0.94 (d, J=6.5 Hz, 6H, Me).

In the next step, to a solution of benzoic acid (2 mmol) in anhydrous tetrahydrofuran (6 mL) was added borane-tetrahydrofuran (6 mL) complex (1M). After stirring for 15 h at 25° C. the mixture was diluted with 10 mL brine and 5 mL water. The organic phase was separated, dried with anhydrous Na$_2$SO$_4$ and concentrated under reduced pressure to give the desired alcohol which was used without further purification in the next step of reaction.

The crude alcohol (2 mmoL) was suspended in anhydrous tetrahydrofuran (12 mL) and stirred. Activated 4 A molecular sieves (4 g) and 5 mmol of pyridinium dichromate was added and the mixture was stirred for 3 h at 25 deg C. A further amount of pyridinium dichromate (5 mmol) was added and the mixture was stirred for another 3 h. The mixture was filtered through silica gel and the filtrate was concentrated under reduced pressure to give the product which was purified by column chromatography with hexane-ethyl acetate (1:1) as eluting solvents.

3-Sulfamoyl-benzaldehyde

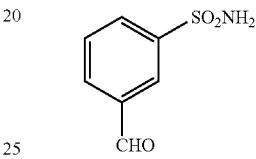

White solid, yield (after 2 steps) 43.4%. $^1$HNMR (300 MHz, in DMSO-$d_6$) δ 10.1 (s, 1H, CHO), 8.32 (s, 1H, Ar—H), 8.13 (t, J=6.9 Hz, J=6.0 Hz, 2H, Ar—H), 7.82 (t, J=7.8 Hz, 1H, Ar—H), 7.55 (s, 2H, NH$_2$)

3-Formyl-N-methyl-benzenesulfonamide

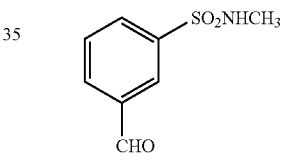

White solid, yield (after 2 steps) 42.5%, $^1$HNMR (300 MHz, in DMSO-$d_6$) δ 10.10 (s, 1H, CHO), 8.26 (s, 1H, Ar—H), 8.18 (d, J=7.6 Hz, 1H, Ar—H), 8.07 (d, J=7.7 Hz, 1H, Ar—H), 7.85 (t, J=7.7 Hz, 1H, Ar—H), 7.65 (s, 1H, N—H), 2.44 (s, 3H, Me)

4-Formyl-N-methyl-benzenesulfonamide

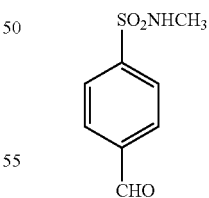

White solid, yield (after 2 steps) 38.9%, $^1$HNMR (300 MHz, in DMSO-$d_6$) δ 10.09 (s, 1H, CHO), 8.18-8.06 (m, 2H, Ar—H), 7.97 (d, J=8.3 Hz, 2H, Ar—H), 7.68 (s, 1H, NH), 2.44 (s, 3H, Me).

3-Formyl-N,N-dimethyl-benzenesulfonamide, N-ethyl-3-formyl-benzenesulfonamide, 3-formyl-N-propyl-benzenesulfonamide and 3-formyl-N-isopropyl-benzenesulfonamide were oils and were used without further purification in the next step of reaction.

REFERENCES

1. Zhang, W.; Go, M.-L., Functionalized 3-benzylidene-indolin-2-ones: Inducers of NAD(P)H-quinone oxidoreductase 1 (NQO1) with antiproliferative activity. *Bioorganic & Medicinal Chemistry* 2009, 17 (5), 2077-2090.
2. Konkel, M. J.; Lagu, B.; Boteju, L. W.; Jimenez, H.; Noble, S.; Walker, M. W.; Chandrasena, G.; Blackburn, T. P.; Nikam, S. S.; Wright, J. L.; Kornberg, B. E.; Gregory, T.; Pugsley, T. A.; Akunne, H.; Zoski, K.; Wise, L. D., 3-arylimino-2-indolones are potent and selective galanin GAL(3) receptor antagonists. *Journal of Medicinal Chemistry* 2006, 49 (13), 3757-3758.
3. Cervena, I.; Metysova, J.; Protiva, M., FLUORINATED ANALOGS OF THE TRICYCLIC NEUROLEPTICS—2,3-DIFLUORO DERIVATIVE OF CLOROTHEPIN. *European Journal of Medicinal Chemistry* 1980, 15 (4), 330-332.
4. Shen, W. B., Kenneth; Oslob, Jojan, D.; Zhong, Min Modulators of Cellular Adhesion. 2005.

Characterization of Synthesized Analogues

(E)-3-Benzylidene-6-chloro-1,3-dihydro-indol-2-one (1-1)

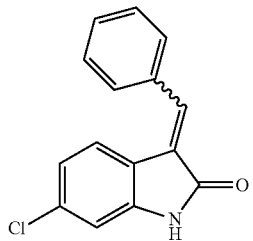 [SMILES: O=C1Nc2cc(Cl)ccc2C1=Cc1ccccc1]

Yield: 11.8%; $^1$H NMR (300 MHz, in DMSO-d$_6$): δ 10.8 (br s, 1H), 7.68-7.75 (m, 3H), 7.47-7.55 (m, 4H), 6.84-6.92 (m, 2H); $^{13}$C NMR (75 MHz, in DMSO-d$_6$): δ 168.5, 144.2, 136.7, 134.1, 131.9, 129.9, 129.3, 128.8, 126.5, 123.5, 120.9, 119.7, 110.1; MS (APCI): m/z 256.0 [M+H]$^+$.

(E)-6-Chloro-3-(2-fluoro-benzylidene)-1,3-dihydro-indol-2-one, (1-2)

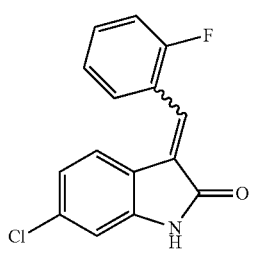 [SMILES: O=C1Nc2cc(Cl)ccc2C1=Cc1ccccc1F]

Yield: 50.2%; $^1$H NMR (300 MHz, in DMSO-d$_6$): δ 10.8 (br s, 1H, NH), 7.74 (t, J=8 Hz, 1H), 7.52-7.58 (m, 2H), 7.32-7.41 (m, 2H), 7.22 (d, J=7.80 Hz, 1H), 6.89-6.91 (m, 2H); $^{13}$C NMR (75 MHz, in DMSO-d$_6$): δ168.0, 159.6, 144.4, 134.5, 132.1, 130.4, 128.6, 128.2, 124.7, 123.9, 122, 121, 119.5, 116, 110.1; MS (APCI): m/z 274.2 [M+H]$^+$.

(E)-6-Chloro-3-(3-fluoro-benzylidene)-1,3-dihydro-indol-2-one (1-3)

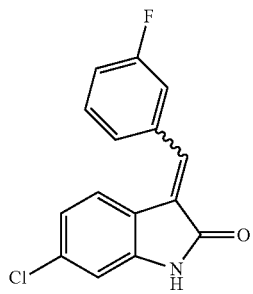 [SMILES: O=C1Nc2cc(Cl)ccc2C1=Cc1cccc(F)c1]

Yield: 36.6%, $^1$H NMR (300 MHz, in DMSO-d$_6$): δ 10.8 (br s, 1H, NH), 7.63 (s, 1H, olefinic H), 7.47-7.58 (m, 3H), 7.42 (d, J=8.7 Hz, 1H), 7.29-7.34 (m, 1H), 6.90-6.92 (m, 2H); $^{13}$C NMR (75 MHz, in DMSO-d$_6$): δ 168.3, 163.7, 160.4, 144.4, 136.5, 134.9, 134.4, 130.8, 127.5, 125.2, 123.6, 120.9, 119.4, 116.5, 115.9, 110.1; MS (APCI): m/z 274.2 [M+H]$^+$.

(E)-6-Chloro-3-(4-fluoro-benzylidene)-1,3-dihydro-indol-2-one (1-4)

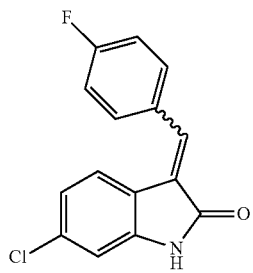 [SMILES: O=C1Nc2cc(Cl)ccc2C1=Cc1ccc(F)cc1]

Yield: 42.86%, $^1$H NMR (300 MHz, in DMSO-d$_6$): δ 10.8 (br s, 1H), 7.72-7.78 (m, 2H), 7.64 (s, 1H), 7.47 (d, 2H), 7.23 (d, J=8.1 Hz, 1H), 7.31-7.38 (m, 2H), 6.84-6.92 (m, 2H); $^{13}$C NMR (75 MHz, in DMSO-d$_6$): δ169.6, 145.3, 136.7, 135.2, 133, 132.8, 131.7, 131.6, 127.6, 124.6, 122, 120.7, 117.2, 116.9, 111.2; MS (APCI): m/z 274.2 [M+H]$^+$.

(E)-6-Chloro-3-(3-methyl-benzylidene)-1,3-dihydro-indol-2-one (1-5)

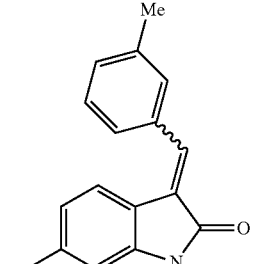

Yield: 3.70%, $^1$H NMR (300 MHz, in DMSO-d$_6$): δ 10.8 (br s, 1H), 7.63 (s, 1H), 7.48-7.51 (m, 3H), 7.41 (t, J=8.1 Hz, 1H), 7.29-7.33 (m, 1H), 6.89-6.91 (m, 2H), 2.36 (s, 3H); $^{13}$C NMR (75 MHz, in DMSO-d$_6$): δ 169.6, 145.3, 142.9, 139.2, 137.9, 135.1, 131.7, 130.9, 129.8, 127.4, 124.6, 122, 120.9, 111.1, 21.9; MS (APCI): m/z 270.0 [M+H]$^+$ (E)-6-Chloro-3-(2-methoxy-benzylidene)-1,3-dihydro-indol-2-one (1-6)

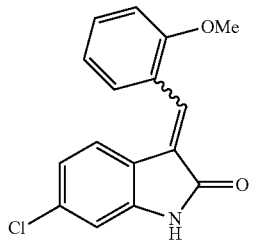 [SMILES: COc1ccccc1C=C1C(=O)Nc2cc(Cl)ccc21]

yield: 61.40%, $^1$H NMR (300 MHz, in DMSO-d$_6$): δ 10.7 (br s, 1H), 7.68 (s, 1H), 7.65 (d, J=7.5 Hz, 1H), 7.50 (t, J=7.5 Hz, 1H), 7.37 (d, J=8.1 Hz, 1H), 7.17 (d, J=8.4 Hz, 1H, H-4), 7.08 (t, J=7.2 Hz, 1H), 6.88-6.91 (m, 2H), 3.85 (s, 3H); $^{13}$C NMR (75 MHz, in DMSO-d$_6$): δ169.6, 158.7, 145.1, 134.9, 133.6, 133.1, 130.6, 127.3, 124.6, 123.6, 121.9, 121.4, 121.1, 112.7, 111.0, 56.7; MS (APCI): m/z 286.0 [M+H]$^+$.

(E)-6-Chloro-3-(3-methoxy-benzylidene)-1,3-dihydro-indol-2-one (1-7)

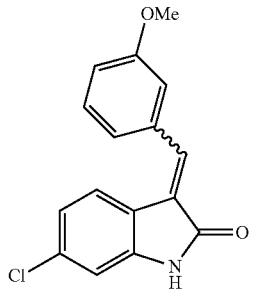 [SMILES: COc1cccc(C=C2C(=O)Nc3cc(Cl)ccc32)c1]

yield 29.8%, $^1$H NMR (300 MHz, in DMSO-d$_6$): δ10.8 (br s, 1H), 7.65 (s, 1H), 7.53 (d, J=8.4, 1H), 7.47 (d, J=8.1 Hz, 1H), 7.24-7.28 (m, 2H), 7.06 (d, J=8.4 Hz, 1H), 6.85-6.95 9 m), 3.80 (s, 3H); $^{13}$C NMR (75 MHz, in DMSO-d$_6$): δ169.6, 160.4, 145.4, 137.6, 136.5, 135.2, 131.1, 127.7, 124.8, 122.6, 122, 120.8, 117, 115.3, 111.2, 56.3; MS (APCI): m/z 286.0 [M+H]$^+$.

(E)-6-Chloro-3-(4-methoxy-benzylidene)-1,3-dihydro-indol-2-one (1-8)

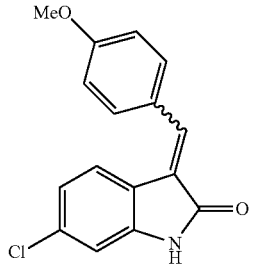 [SMILES: COc1ccc(C=C2C(=O)Nc3cc(Cl)ccc32)cc1]

yield 40.4%, $^1$H NMR (300 MHz, in DMSO-d$_6$): δ10.8 (br s, 1H), 7.62-7.72 (m, 4H), 7.09 (d, J=8.7 Hz, 2H), 6.89-6.95 (m, 2H), 3.85 (s, 3H); $^{13}$C NMR (75 MHz, in DMSO-d$_6$): δ168.8, 160.7, 143.9, 136.9, 133.5, 126.3, 124.3, 123.2, 120.1, 120, 114.3, 109.9, 55.3; MS (APCI): m/z 286.2 [M+H]$^+$.

(E)-6-Chloro-3-(2-trifluoromethyl-benzylidene)-1,3-dihydro-indol-2-one (1-9)

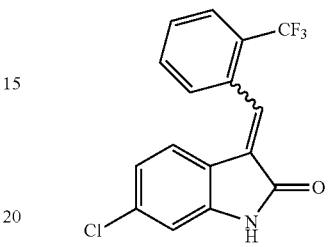

yield: 40.3%; $^1$H NMR (300 MHz, in DMSO-d$_6$): δ10.9 (br s, 1H), 7.91 (d, J=7.8 Hz, 1H), 7.68-7.81 (m, 4H), 6.88 (s, 1H), 6.75-6.84 (m, 2H); $^{13}$C NMR (75 MHz, in DMSO-d$_6$): δ 167.7, 144.5, 134.7, 132.9, 132.8, 131.6, 130.1, 129.8, 129.3, 127.1, 126.7, 126.43, 126.36, 123.8, 121.1, 119.2, 110.3; MS (APCI): m/z 323.9 [M+H].

(E) 6-Chloro-1-methyl-3-(3-trifluoromethyl-benzylidene)-1,3-dihydro-indol-2-one (1-10)

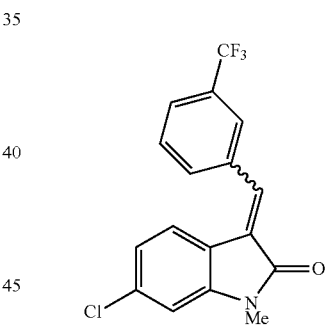

Yield 16.6%; Me $^1$HNMR (300 MHz DMSO-d6), δ 7.98 (d, J=7.8 Hz, 2H), 7.85-7.72 (m, 3H), 7.29 (d, J=8.1 Hz, 1H), 7.17 (s, 1H), 6.91 (d, J=8.1 Hz, 1H), 3.19 (s, 3H);

$^{13}$CNMR (75 MHz, DMSO-d6), δ 167.0, 145.7, 143.4, 135.2, 135.1, 134.9, 134.4, 133.9, 132.9, 130.0, 129.3, 127.1, 126.3, 125.9, 125.9, 123.0, 122.3, 121.5, 121.4, 121.2, 118.6, 109.5, 26.2, 26.0. More C atoms were detected in the 13C NMR data than the expected number. It is proposed that this may be due to isomerization during the scanning process which took place overnight, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.

MS (APCI): m/z 338.4 [M+1]$^+$.

(E)-6-Chloro-3-(4-trifluoromethyl-benzylidene)-1,3-dihydro-indol-2-one (1-11)

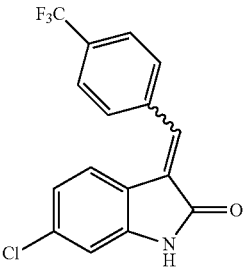 [SMILES: O=C1Nc2cc(Cl)ccc2C1=Cc1ccc(C(F)(F)F)cc1]

yield: 29.2%; $^1$H NMR (300 MHz, in DMSO-$d_6$): δ 10.8 (br s, 1H), 7.86-7.92 (m, 4H), 7.70 (s, 1H), 7.40 (d, J=8.7 Hz, 1H), 6.88-6.90 (m, 2H); $^{13}$C NMR (75 MHz, in DMSO-$d_6$): δ169.3, 145.7, 139.5, 135.7, 133.1, 131, 129.3, 126.8, 124.9, 124.3, 122.1, 120.4, 111.3; MS (APCI): m/z 324.0 [M+H]$^+$.

(E)-6-Chloro-3-(3,4-difluoro-benzylidene) 1,3-dihydro-indolin-2-one (1-12)

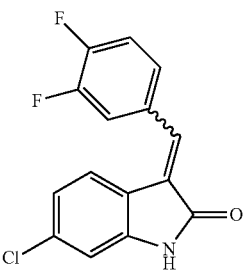 [SMILES: O=C1Nc2cc(Cl)ccc2C1=Cc1ccc(F)c(F)c1]

Yield: 41%; $^1$H NMR (300 MHz, in DMSO-$d_6$): δ 10.78 (s, 1H), 7.76 (t, J=8.7 Hz, 1H), 7.58 (s, 3H), 7.41 (d, J=8.1 Hz, 1H), 6.89 (d, J=8.4 Hz, 2H); $^{13}$C NMR (75 MHz, in DMSO-$d_6$): δ 168.2, 144.4, 134.4, 134.1, 131.7, 127.4, 126.5, 126.5, 126.4, 123.7, 121.0, 119.3, 118.6, 118.3, 118.2, 117.9, 110.1; MS (APCI): m/z 292.2 [M+H]$^+$.

(E)-6-Chloro-3-(2-trifluoromethoxyl-benzylidene)-1,3-dihydro-indolin-2-one (1-13)

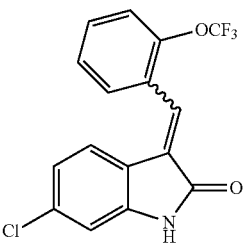 [SMILES: O=C1Nc2cc(Cl)ccc2C1=Cc1ccccc1OC(F)(F)F]

Yield 73.6%; $^1$H NMR (300 MHz DMSO-d6) δ 10.86 (s, 1H), 7.81 (d, J=7.0 Hz, 1H), 7.69-7.48 (m, 4H), 7.12 (d, J=8.0 Hz, 1H), 6.88 (d, J=7.9 Hz, 2H); $^{13}$NMR (75 MHz, DMSO-d6), δ 167.8, 166.3, 146.4, 146.1, 144.5, 142.6, 134.7, 134.0, 132.2, 131.8, 131.5, 130.5, 129.1, 129.0, 128.2, 127.9, 127.7, 126.8, 126.6, 125.1, 123.7, 122.5, 121.9, 121.7, 121.2, 121.1, 120.6, 119.3, 118.3, 114.8, 110.2, 109.5; MS (APCI): m/z 340.4 [M+H]$^+$.

* More C atoms were detected in the $^{13}$C NMR data than the expected number. It is proposed that this may be due to isomerization during the scanning process which took place overnight, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.

(E)-6-Chloro-3-(3-trifluoromethoxyl-benzylidene)-1,3-dihydro-indol-2-one (1-14)

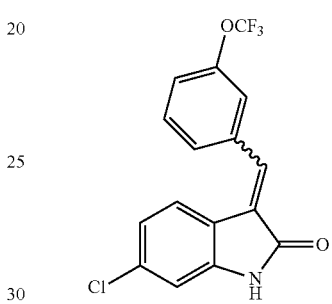

Yield 57.1%; $^1$HNMR (300 MHz, DMSO-d6), δ 10.8 (s, 1H), 7.72-7.62 (m, 4H), 7.48 (d=7.8 Hz, 1H), 7.33 (d, J=8.1 Hz, 1H), 6.89 (d, J=7.8 Hz, 2H);

$^{13}$CNMR (75 MHz, DMSO-d6), δ 168.2, 166.9, 148.5, 148.1, 144.5, 142.2, 136.5, 135.8, 135.6, 134.6, 134.5, 133.6, 131.2, 130.9, 130.1, 128.2, 127.9, 127.2, 123.5, 123.4, 123.3, 122.7, 122.1, 121.8, 121.7, 121.5, 121.0, 120.9, 119.4, 118.4, 118.3, 110.2, 109.5; More C atoms were detected in the 13C NMR data than the expected number. It is proposed that this may be due to isomerization during the scanning process which took place overnight, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.

MS (APCI): m/z 340.5 [M+1]$^+$.

(E)-6-Chloro-3-(4-trifluoromethoxyl-benzylidene)-1,3-dihydro-indol-20-one (1-15)

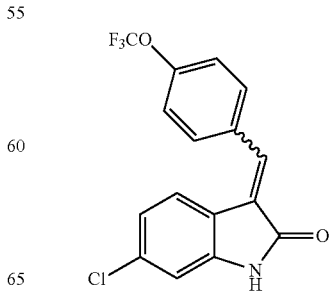

Yield 83.0%; ¹H NMR (300 MHz DMSO-d6), δ 10.80 (s, 1H), 7.80 (t, J=9.0 Hz, 2H), 7.65 (s, 1H), 7.50 (q, J=16.5 Hz, 3H), 6.90 (d, J=7.1 Hz, 2H); ¹³NMR (75 MHz, DMSO-d6), δ 168.4, 166.9, 149.3, 148.9, 144.4, 142.0, 135.8, 134.8, 134.4, 133.9, 133.3, 132.8, 131.4, 127.2, 126.4, 123.6, 123.5, 121.7, 121.4, 121.1, 121.0, 120.9, 120.3, 119.4, 118.3, 110.2, 109.4; MS (APCI): m/z 340.4 [M+H]⁺.

* More C atoms were detected in the ¹³C NMR data than the expected number. It is proposed that this may be due to isomerization during the scanning process which took place overnight, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.

(E)-6-Chloro-3-(3-methanesulfonyl-benzylidene)-1,3-dihydro-indol-2-one (1-16)

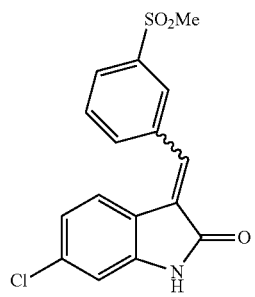 [SMILES: CS(=O)(=O)c1cccc(C=C2C(=O)Nc3cc(Cl)ccc32)c1]

Yield 45.5%; ¹HNMR (300 MHz DMSO-d₆), δ 10.83 (s, 1H), 8.22 (s, 1H), 8.02 (d, J=7.6 Hz, 2H), 7.80 (t, J=7.8 Hz, 1H), 7.72 (s, 1H), 7.35 (d, J=8.7 Hz, 1H), 6.89 (d, J=6.2 Hz, 2H), 3.29 (s, 1H); ¹³NMR (75 MHz, DMSO-d₆), δ 168.2, 144.6, 141.3, 135.4, 134.6, 134.3, 134.0, 130.1, 128.1, 127.7, 127.4, 123.6, 121.0, 119.3, 110.2, 43.3; MS (APCI): m/z 334.3 [M+H]⁺.

(E) 3-(6-Chloro-2-oxo-1,2-dihydro-indol-3-ylidenemethyl)-benzene-sulfonamide (1-17)

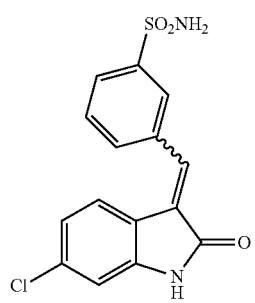 [SMILES: NS(=O)(=O)c1cccc(C=C2C(=O)Nc3cc(Cl)ccc32)c1]

Yield 47.8%;
¹HNMR (300 MHz DMSO-d6), δ 10.8 (s, 1H), 8.13 (s, 1H), 7.90 (t, J=7.8 Hz, J=6.6 Hz, 2H), 7.49 (s, 2H), 7.28 (d, J=8.1 Hz, 1H), 6.91 (d, J=8.1 Hz, 1H);
¹³CNMR (75 MHz, DMSO-d6), δ 168.2, 144.5, 144.5, 134.9, 134.7, 134.6, 132.5, 129.7, 127.8, 126.5, 125.8, 123.6, 121.0, 119.3, 110.2. MS (APCI): m/z 335.3 [M+1]⁺.

(E)-3-(6-Chloro-2-oxo-1,2-dihydro-indol-3-ylidenemethyl)-N-methyl-benzenesulfonamide (1-18)

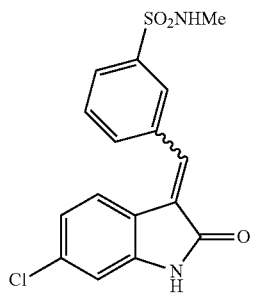

Yield 22.9%;
¹HNMR (400 MHz DMSO-d6, δ 10.84 (s, 1H), 8.04 (s, 1H), 7.92 (d, J=7.6 Hz, 1H), 7.85 (d, J=7.6 Hz, 1H), 7.75 (t, J=7.6 Hz, 1H), 7.71 (d, 1H), 7.58 (s, 1H), 7.32 (d, J=8 Hz, 1H), 6.92 (d, J=1.6 Hz, 1H), 6.90 (dd, J=8.4 Hz, 1H), 2.46 (s, 3H);
¹³CNMR (100 MHz, DMSO-d6), δ 168.3, 144.6, 140.0, 135.3, 134.8, 134.7, 133.1, 130.1, 128.0, 127.7, 126.9, 123.6, 121.1, 119.4, 110.4, 28.7;
MS (APCI): m/z 350.1 [M+1]⁺.

(E) 3-(6-Chloro-2-oxo-1,2-dihydro-indol-3-ylidenemethyl)-benzonitrile (1-19)

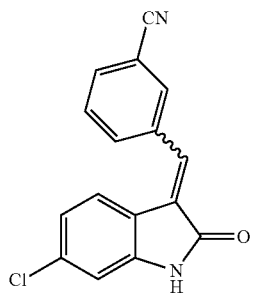 [SMILES: N#Cc1cccc(C=C2C(=O)Nc3cc(Cl)ccc32)c1]

Yield 57.0%; ¹HNMR (300 MHz DMSO-d6), δ 10.8 (s, 1H), 8.10 (s, 1H), 7.99 (d, J=7.8 Hz, 1H), 7.91 (d, J=7.8 Hz, 1H), 7.71 (t, J=7.8 Hz, 1H), 7.63 (s, 1H), 7.28 (d, J=8.7 Hz, 1H), 6.88 (d, J=7.2 Hz, 2H);
¹³CNMR (75 MHz, DMSO-d6), δ 168.3, 144.6, 135.6, 134.8, 134.1, 133.6, 133.1, 132.7, 130.1, 128.3, 123.8, 121.2, 119.4, 118.4, 112.1, 110.4; MS (APCI): m/z 281.5 [M+1]⁺.

(E)-3-(6-Chloro-2-oxo-1,2-dihydro-indol-3-ylidenemethyl)-N,N-dimethyl-benzenesulfonamide(1-20)

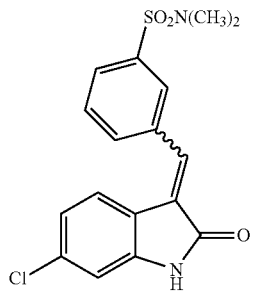

Yield 22.9%; ¹H NMR (400 MHz, DMSO-d6) 10.79 (s, 1H), 8.78 (s, 1H), 8.50 (d, J=7.7 Hz, 1H), 7.98 (s, 1H), 7.89-7.65 (m, 3H), 7.06 (d, J=8.1 Hz, 1H), 6.88 (d, J=16.9 Hz, 1H), 2.67 (s, 6H); ¹³C NMR (101 MHz, DMSO-d6), δ 166.8, 142.2, 135.6, 135.5, 134.9, 134.6, 133.6, 130.1, 129.2, 128.7, 127.4, 123.3, 121.7, 121.0, 109.5, 40.1, 38.8; MS (ACPI): m/z 361.5 [M−H]⁻.

(E)-4-(6-Chloro-2-oxo-1,2-dihydro-indol-3-ylidenemethyl)-N-methyl-benzenesulfonamide (1-21)

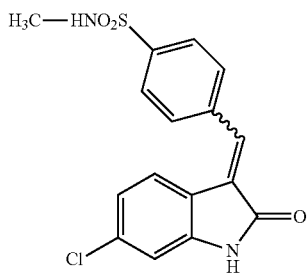

Yield 40.7%, ¹H NMR (400 MHz, DMSO-d6) δ11.10-10.52 (br, 1H), 7.88 (s, 4H), 7.68 (s, 1H), 7.44-7.38 (m, 1H), 6.91 (dd, J=6.9, 2.0 Hz, 2H), 2.46 (d, J=8.9 Hz, 3H)

13C NMR (100 MHz, DMSO-d6), δ168.4, 144.6, 140.0, 138.2, 134.8, 134.7, 132.1, 130.1, 128.3, 127.2, 126.4, 124.0, 121.3, 119.4, 110.4, 28.8; MS (ESI): m/z 347.1 [M−H]⁻.

(E)-3-(6-Chloro-2-oxo-1,2-dihydro-indol-3-ylidenemethyl)-N-ethyl-benzenesulfonamide (1-22)

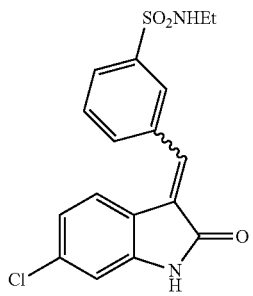

Yield 3.59% (after 3 steps), ¹H NMR (400 MHz, DMSO-d₆), δ 10.84 (s, 1H), 8.05 (s, 1H), 7.90 (dd, J=18.7, 7.8 Hz, 2H), 7.77-7.62 (m, 3H), 7.33 (d, J=8.2 Hz, 1H), 6.99-6.80 (m, 2H), 2.83 (dd, J=6.7, 3.9 Hz, 2H), 0.98 (t, J=7.2 Hz, 3H); 13C NMR (100 MHz, DMSO-d6), δ 168.2, 144.6, 141.2, 135.2, 134.8, 134.7, 132.9, 130.0, 128.0, 127.4, 126.7, 123.5, 121.0, 119.4, 110.3, 37.6, 14.8. MS (ESI): m/z 361.2 [M−H]⁻.

E/Z-3-(6-Chloro-2-oxo-1,2-dihydro-indol-3-ylidenemethyl)-N-propyl-benzenesulfonamide (1-23)

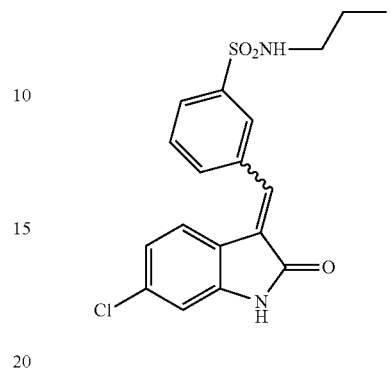

Yield 20.9% (after 3 steps), ¹H NMR (400 MHz, DMSO-d₆), δ10.84 (s, 1H), 8.05 (s, 1H), 7.95-7.80 (m, 2H), 7.81-7.62 (m, 3H), 7.33 (d, J=8.2 Hz, 1H), 6.96-6.80 (m, 2H), 2.75 (t, J=7.1 Hz, 2H), 1.47-1.28 (m, 2H), 0.79 (t, J=7.4 Hz, 3H); 13C NMR (100 MHz, DMSO-d6), δ ppm, 168.2, 144.5, 141.3, 135.2, 134.7, 134.6, 132.9, 129.9, 127.9, 127.3, 126.6, 123.5, 120.9, 119.3, 110.2, 44.3, 22.4, 11.0. MS (ESI): m/z 375.3 [M−H]⁻.

E/Z 3-(6-Chloro-2-oxo-1,2-dihydro-indol-3-ylidenemethyl)-N-isopropyl-benzenesulfonamide (1-24)

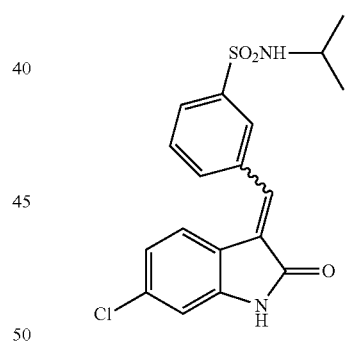

Yield 5.72 (after 3 steps), 1H NMR (400 MHz, DMSO-d₆), δ 10.81 (s, 1H), 8.02 (s, 1H), 7.88-7.82 (m, 2H), 7.74-7.63 (m, 3H), 7.28 (d, J=8.27 Hz, 1H), 6.90 (d, J=1.93 Hz, 1H), 6.86-6.80 (m, 1H), 3.29-3.22 (m, 1H), 0.92 (d, J=6.54 Hz, 6H); 13C NMR (100 MHz, DMSO-d6)*, 172.2, 168.4, 144.6, 142.5, 136.0, 135.2, 134.9, 134.8, 132.9, 130.1, 129.4, 129.2, 128.0, 127.4, 126.6, 123.6, 121.1, 119.5, 110.5, 45.5, 42.2, 23.3, 23.3, 21.1. MS (ESI): m/z 375.3 [M−H]⁻.

* More C atoms were detected in the ¹³C NMR data than the expected number. It is proposed that this may be due to isomerization during the scanning process which took place overnight, resulting in a mixture of isomers. The isomerization could be identified by comparing the proton spectrum which is done before carbon spectrum and the one which is done after the carbon spectrum.

(E)-3-Benzylidene-5-chloro-1,3-dihydro-indol-2-one (2-1)

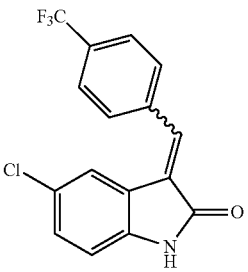 [SMILES: O=C1Nc2ccc(Cl)cc2C1=Cc1ccc(C(F)(F)F)cc1]

Yield: 62.8%; ¹H NMR (300 MHz, in DMSO-$d_6$): δ10.8 (br s, 1H), 7.73 (s, 1H, H), 7.70 (d, J=7 Hz, 2H), 7.54-7.59 (m, 3H), 7.51 (d, J=2.1 Hz, 1H, H-4), 7.29 (d, J=8.4 Hz, 1H), 6.90 (d, J=8.4 Hz, 1H); ¹³C NMR, (75 MHz, in DMSO-$d_6$): δ 168.3, 141.7, 137.7, 134, 130.1, 129.6, 129.2, 128.9, 126.9, 124.9, 122.5, 121.7, 111.5; MS (APCI): m/z 256.1 [M+H].

(E)-5-Chloro-3-(2-fluoro-benzylidene)-1,3-dihydro-indol-2-one (2-2)

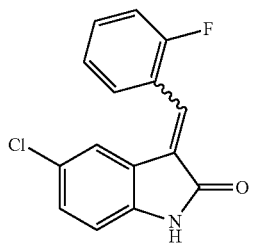 [SMILES: O=C1Nc2ccc(Cl)cc2C1=Cc1ccccc1F]

Yield 89.4%; ¹H NMR (300 MHZ DMSO-$d_6$) δ10.8 (br s, 1H, NH), 7.74 (t, J=7.5 Hz, 1H), 7.62 (s, 1H, olefinic H), 7.51-7.60 (m, 1H), 7.35-7.43 (m, 2H), 7.28 (d, J=8.1 Hz, 1H), 7.13 (d, J=2.1 Hz, 1H), 6.89 (d, J=8.4 Hz, 1H); ¹³C NMR, (75 MHz, in DMSO-$d_6$): δ168.8, 162.3, 159.0, 143.0, 141.0, 133.5, 133.4, 131.6, 131.1, 130, 126.2, 125.8, 123.3, 123.2, 123, 122.8, 117.4, 117.1, 112.6; MS (APCI): m/z 273.9 [M+H]⁺.

(E)-5-Chloro-3-(3-fluoro-benzylidene)-1,3-dihydro-indol-2-one (2-3)

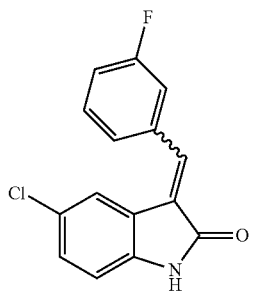 [SMILES: O=C1Nc2ccc(Cl)cc2C1=Cc1cccc(F)c1]

Yield 37.0%; ¹H NMR (300 MHZ, DMSO-$d_6$) δ 10.8 (br s, 1H), 7.69 (s, 1H), 7.53-7.60 (m, 3H), 7.37 (d, J=9 Hz, 1H), 7.33 (s, 1H), 7.30 (d, J=1.8 Hz), 6.90 (d, J=8.4 Hz, 1H); ¹³C NMR, (75 MHz, in DMSO-$d_6$): δ168.0, 162.1, 141.8, 136.4, 135.9, 130.9, 129.9, 127.8, 125.1, 124.9, 122.1, 121.9, 116.7, 115.8, 111.5; MS (APCI): m/z 273.9 [M+H]⁺.

(E)-5-Chloro-3-(4-fluoro-benzylidene)-1,3-dihydro-indol-2-one (2-4)

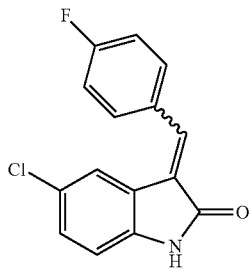 [SMILES: O=C1Nc2ccc(Cl)cc2C1=Cc1ccc(F)cc1]

Yield 63.0%; ¹H NMR (300 MHZ, DMSO-$d_6$) δ10.8 (br s, 1H), 7.74-7.79 (m, 2H), 7.69 (s, 1H), 7.36-7.42 (m, 2H), 7.26-7.32 (m, 2H), 6.88 (d, J=8.4 Hz, 1H); ¹³C NMR, (75 MHz, in DMSO-$d_6$): δ167.9, 142.0, 139.9, 138.5, 138.3, 135.5, 132.1, 130.1, 129.8, 128.4, 125.7, 125.0, 122.0, 111.6; MS (APCI): m/z 273.9 [M+H]⁺.

(E)-5-Chloro-3-(3-methoxybenzylidene)-dihydro-indol-2-one (2-5)

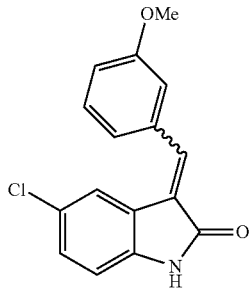 [SMILES: COc1cccc(C=C2C(=O)Nc3ccc(Cl)cc32)c1]

Yield 79.0%; ¹H NMR (300 MHZ, DMSO-$d_6$) δ 10.8 (br s, 1H), 7.69 (s, 1H), 7.44-7.50 (m, 2H), 7.25-7.30 (m, 3H), 7.08 (d, J=8.4 Hz, 1H), 6.89 (d, J=8.4 Hz, 1H), 3.81 (s, 3H), ¹³C NMR, (75 MHz, in DMSO-$d_6$): δ169.3, 160.4, 142.8, 138.6, 136.4, 131.1, 130.1, 128.1, 125.9, 123.5, 123.1, 122.5, 117.2, 115.2, 112.6, 56.3. MS (APCI): m/z 285.9 [M+H]⁺.

(E)-5-Chloro-3-(2-trifluoromethylbenzylidene)-1,3-dihydro-indol-2-one (2-6)

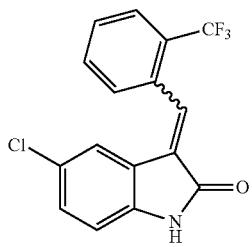 [SMILES: O=C1Nc2ccc(Cl)cc2C1=Cc1ccccc1C(F)(F)F]

Yield 50.8%; $^1$H NMR (300 MHZ DMSO-d$_6$) δ10.9 (br s, 1H), 7.94 (d, J=7.5 Hz, 1H), 7.74-7.84 (m, 4H), 7.28 (dd, J1=10 Hz, J2=1.8 Hz, 1H), 6.89 (d, J=8.1 Hz, 1H), 6.64 (d, J=2.1 Hz, 1H); $^{13}$C NMR, (75 MHz, in DMSO-d$_6$): δ 167.5, 142.0, 133.0, 132.8, 132.7, 130.2, 130.1, 129.6, 127.1, 126.7, 126.6, 126.5, 125.7, 125.1, 122.1, 122.0, 111.8; MS (APCI): m/z 323.8 [M+H]$^+$.

(E)-5-Chloro-3-(3-(trifluoromethyl)benzylidene)-1,3-dihydro-indol-2-one (2-7)

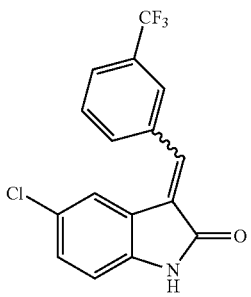 [SMILES: O=C1Nc2ccc(Cl)cc2C1=Cc1cccc(C(F)(F)F)c1]

Yield 38.5%; $^1$HNMR (300 MHZ, DMSO-d$_6$) δ 10.8 (s, 1H), 7.99-8.06 (m, 2H), 7.70-7.88 (m, 3H), 7.26-7.32 (m, 2H), 6.90 (d, J=8.4 Hz, 1H).

$^{13}$CNMR (75 MHz, DMSO-d$_6$), δ 167.9, 166.7, 141.9, 139.7, 135.6, 135.5, 135.1, 133.0, 130.0, 129.3, 128.3, 126.3, 125.7, 125.6, 124.9, 122.0, 111.6.

More C atoms were detected in the 13C NMR data than the expected number. It is proposed that this may be due to isomerization during the scanning process which took place overnight, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.

MS (APCI): m/z 323.9 [M+1]$^+$.

(E)-5-Chloro-3-(4-trifluoromethylbenzylidene)-1,3-dihydro-indol-2-one (2-8)

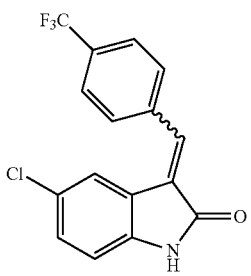 [SMILES: O=C1Nc2ccc(Cl)cc2C1=Cc1ccc(C(F)(F)F)cc1]

Yield 38.5%; $^1$H NMR (300 MHZ, DMSO-d$_6$) δ 10.8 (br s, 1H), 7.91 (t, J=9 Hz, 4H), 7.75 (s, 1H), 7.28-7.33 (m, 2H), 6.91 (d, J=8.4 Hz, 1H); $^{13}$C NMR, (75 MHz, in DMSO-d$_6$): δ167.7, 142.0, 139.9, 138.3, 135.3, 132.1, 130.1, 129.8, 129.4, 128.4, 125.7, 125.0, 122.1, 121.9, 111.6; MS (APCI): m/z 323.9 [M+H]$^+$.

(E)-5-Chloro-3-(3,4-difluoro-benzylidene)-1,3-dihydro-indol-2-one (2-9)

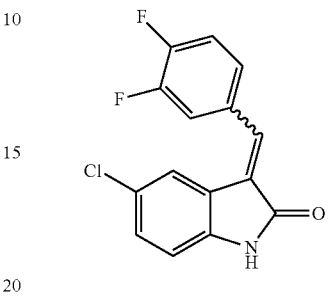

Yield: 51%; $^1$H NMR (300 MHz, DMSO-d$_6$): δ 10.82 (s, 1H), 8.86 (m, 1H), 8.01 (br, 1H), 7.89 (d, J=1.8 Hz, 1H), 7.55 (q, J=8.7 Hz, 1H), 7.23 (dd, J=1.8 Hz, 1H), 6.32 (d, J=8.4 Hz, 1H); $^{13}$C NMR, (75 MHz, in DMSO-d$_6$): δ 166.8, 152.3, 152.1, 148.9, 147.1, 147.0, 139.5, 136.2, 131.4, 131.3, 131.3, 131.3, 130.3, 128.6, 126.4, 126.3, 125.5, 120.2, 120.0, 119.9, 117.5, 117.2, 110.8; MS (APCI): m/z 292.2 [M+H]$^+$.

More C atoms were detected in the $^{13}$C NMR data than the expected number. It is proposed that this may be due to isomerization during the scanning process, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.

(E)-5-Chloro-3-(3-trifluoromethoxyl-benzylidene)-1,3-dihydro-indol-2-one (2-10)

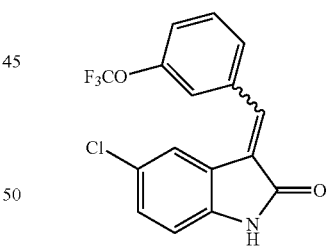

Yield 13.5%; $^1$H NMR (300 MHz DMSO-d6) δ 10.79 (s, 1H), 7.70 (s, 4H), 7.50 (s, 1H), 7.29 (d, J=7.2 Hz, 2H), 6.89 (d, J=8.4 Hz, 1H)

$^{13}$C NMR (75 MHz, DMSO-d6) δ 167.9, 166.7, 148.4, 148.1, 141.9, 139.7, 136.3, 135.7, 135.5, 131.3, 131.0, 130.1, 130.0, 128.9, 128.4, 128.2, 127.3, 126.3, 125.5, 125.0, 123.3, 122.9, 122.4, 122.1, 121.8, 121.3, 120.2, 118.3, 111.6, 110.9; *

More C atoms were detected in the $^{13}$C NMR data than the expected number. It is proposed that this may be due to isomerization during the scanning process which took place overnight, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.

MS (APCI): m/z 340.5 [M+H]+.

(E)-5-Chloro-3-(3-methanesulfonyl-benzylidene)-1,3-dihydro-indol-2-one (2-11)

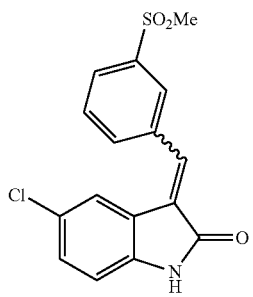 [SMILES: CS(=O)(=O)c1cccc(C=C2C(=O)Nc3ccc(Cl)cc32)c1]

Yield 49.1%; $^1$HNMR (300 MHz DMSO-d6) δ 10.8 (s, 1H), 8.25 (s, 1H), 8.02 (d, J=6.9 Hz, 2H), 7.77-7.85 (m, 2H), 7.31 (s, 2H), 6.91 (d, J=7.8 Hz, 1H), 3.29 (s, 3H); $^{13}$CNMR (75 MHz, DMSO-d6) δ 167.9, 142.0, 141.3, 135.4, 135.2, 134.2, 130.1, 128.4, 127.9, 127.3, 125.1, 122.0, 121.9, 111.7, 43.3;

MS (APCI): m/z 334.4 [M+1]+.

E/Z 3-(5-Chloro-2-oxo-1,2-dihydro-indol-3-ylidenemethyl)-benzenesulfonamide (2-12)

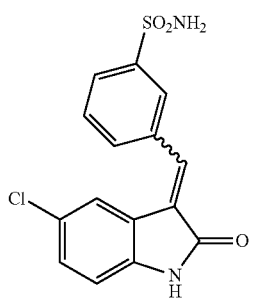 [SMILES: NS(=O)(=O)c1cccc(C=C2C(=O)Nc3ccc(Cl)cc32)c1]

Yield 17.9%;

$^1$HNMR (300 MHz DMSO-d6) δ 10.8 (s, 1H), 8.12 (s, 1H), 7.84 (t, J=9.0 Hz, J=9.6 Hz, 2H), 7.75 (t, J=7.5 Hz, J=7.8 Hz, 2H), 7.47 (br, 1H), 7.32-7.29 (m, 2H), 6.92 (d, J=8.1 Hz, 1H); $^{13}$CNMR (75 MHz, DMSO-d6), δ 168.0, 166.7, 144.7, 144.2, 141.9, 139.8, 136.9, 135.8, 134.8, 134.2, 132.5, 130.2, 129.7, 129.0, 128.8, 128.2, 127.5, 127.3, 126.7, 126.4, 125.9, 125.6, 125.3, 122.0, 120.4, 111.7.

MS (ESI): m/z 335.1[M+1]+.

More C atoms were detected in the $^{13}$C NMR data than the expected number. It is proposed that this may be due to isomerization during the scanning process which took place overnight, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.

(E) 3-(5-Chloro-2-oxo-1,2-dihydro-indol-3-ylidenemethyl)-benzonitrile (2-13)

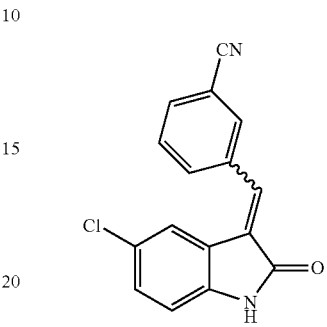

Yield, 67.7%; $^1$HNMR (300 MHz DMSO-d$_6$), δ 10.84 (s, 1H), 8.87 (s, 1H), 8.45 (d, J=7.8 Hz, 1H), 7.95-7.89 (m, 2H), 7.82 (s, 1H), 7.29 (d, J=8.1 Hz, 1H), 6.85 (d, J=8.1 Hz, 1H); $^{13}$NMR (75 MHz, DMSO-d$_6$), δ 166.6, 139.8, 136.2, 135.4, 134.7, 134.6, 133.4, 129.5, 129.1, 128.5, 127.8, 126.1, 125.6, 122.0, 120.3, 118.5, 112.0, 111.3, 111.0; MS (APCI): m/z 281.5 [M+H]+.

* More C atoms were detected in the 13C NMR data than the expected number. It is proposed that this may be due to isomerization during the scanning process which took place overnight, resulting in a mixture of isomers. The isomerization could be identified by comparing the proton spectrum which is done before carbon spectrum and the one which is done after the carbon spectrum.

(E)-3-(5-Chloro-2-oxo-1,2-dihydro-indol-3-ylidenemethyl)-N-methyl-benzenesulphonamide (2-14)

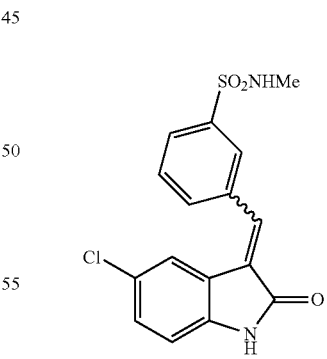

Yield 29.3%; $^1$H NMR (400 MHz, DMSO-d6) 10.81 (s, 1H), 8.07 (s, 1H), 7.91 (dd, J=17.4 Hz, 2H), 7.84-7.74 (m, 2H), 7.61 (q, J=4.5 Hz, 1H), 7.37-7.20 (m, 2H), 6.91 (d, J=8.3 Hz, 1H), 2.48 (d, J=4.8 Hz, 3H); $^{13}$C NMR (101 MHz, DMSO-d6), δ 166.6, 139.7, 139.5, 136.6, 135.1, 134.4, 129.8, 129.2, 128.9, 128.0, 127.4, 126.3, 125.5, 120.3, 110.9, 28.6; MS (ACPI): m/z 347.5 [M−H]−;

(E)-3-Benzylidene-6-fluoro-1,3-dihydro-indol-2-one (3-1)

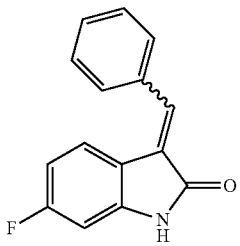 [SMILES: O=C1Nc2cc(F)ccc2C1=Cc1ccccc1]

Yield: 14.6%; ¹HNMR (300 MHz, in DMSO-$d_6$): δ 10.7 (br s, 1H), 7.61 (d, J=6.9 Hz, 1H), 7.57 (s, 1H), 7.41-7.50 (m, 4H), 6.58-6.73 (m, 2H); ¹³NMR (75 MHz, DMSO-$d_6$), δ 169.9, 144.9, 136.4, 134.5, 132.2, 130.5, 129.6, 128.8, 126.9, 124.5, 117.8, 108.3, 98.9. MS (APCI): m/z 240.2 [M+H]⁺.

(E)-6-Fluoro-3-(2-fluoro-benzylidene)-1,3-dihydro-indol-2-one (3-2)

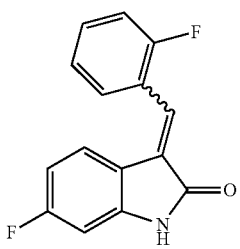 [SMILES: O=C1Nc2cc(F)ccc2C1=Cc1ccccc1F]

Yield: 54.7%; ¹HNMR (300 MHz, in DMSO-$d_6$), δ 10.8 (br s, 1H), 7.74 (t, J=7.5 Hz, 1H), 7.54-7.57 (m, 1H), 7.52 (s, 1H), 7.33-7.41 (m, 2H), 7.24 (d, J=6.3 Hz, 1H), 6.65-6.72 (m, 2H); ¹³NMR (75 MHz, DMSO-$d_6$), δ 168.5, 165.0, 161.5, 157.9, 145.0, 132.0, 130.4, 128.7, 127.1, 124.8, 122.1, 117.1, 116.1, 107.8, 98.3; MS (APCI): m/z 258.3 [M+H]⁺.

(E)-6-Fluoro-3-(3-fluoro-benzylidene)-1,3-dihydro-indol-2-one (3-3)

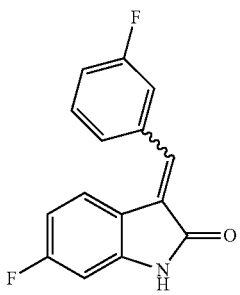 [SMILES: O=C1Nc2cc(F)ccc2C1=Cc1cccc(F)c1]

Yield 23.6%, ¹HNMR (300 MHZ DMSO-$d_6$) δ10.8 (br s, 1H, NH), 7.55 (s, 1H), 7.41-7.53 (m, 4H), 7.23-7.29 (m, 1H), 6.65-6.70 (m, 1H), 6.59-6.62 (m, 1H); ¹³CNMR (75 MHz, DMSO-$d_6$), δ168.6, 167.2, 163.7, 145, 144.9, 142.3, 136.6, 133.7, 130.8, 127.5, 125.1, 117.0, 115.9, 115.6, 107.8, 107.5, 98.4, 89.0; MS (APCI): m/z, 258.2 [M+1]⁺.

(E)-6-Fluoro-3-(4-fluoro-benzylidene)-1,3-dihydro-indol-2-one (3-4)

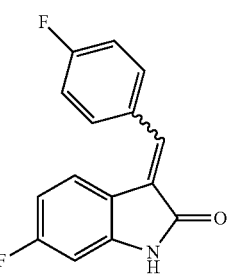

Yield: 27.5%, ¹HNMR (300 MHz, in DMSO-$d_6$), δ10.8 (br s, 1H), 7.76 (dd, J1=14 Hz, J2=6 Hz), 7.59 (s, 1H), 7.50 (t, J=6.3 Hz, 1H), 7.36 (t, J=8.7 Hz), 6.65-6.71 (m, 2H); ¹³NMR (75 MHz, DMSO-$d_6$), δ 168.8, 164.4, 161.1, 144.8, 134.3, 131.6, 130.6, 126.5, 123.8, 117.1, 115.8, 107.4, 98.1; MS (APCI): m/z 258.2 [M+H]⁺.

(E)-6-Fluoro-3-(2-trifluoromethyl-benzylidene)-1,3-dihydro-indol-2-one (3-5)

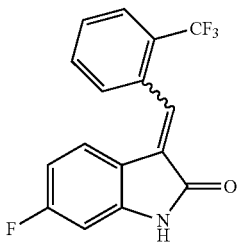 [SMILES: O=C1Nc2cc(F)ccc2C1=Cc1ccccc1C(F)(F)F]

Yield 45.8%; ¹H NMR (300 MHZ DMSO-$d_6$) δ 10.6 (br s, 1H), 7.91 (d, J=7.5 Hz), 7.76-7.84 (m, 2H), 7.66-7.73 (m, 2H), 6.78 (dd, J1=14 Hz, J2=5.7 Hz, 1H), 6.70 (dd, J1=12 Hz, J2=2.1 Hz, 1H), 6.56-6.63 (m, 1H); ¹³NMR (75 MHz, DMSO-d6) δ 168.1, 163.4, 145.0, 133.0, 130.2, 129.8, 126.8, 126.5, 126.4, 125.7, 124.3, 116.8, 107.8, 98.4; MS (APCI): m/z 308.0 [M+H]⁺.

(E)-6-Fluoro-3-(3-trifluoromethyl-benzylidene)-1,3-dihydro-indol-2-one (3-6)

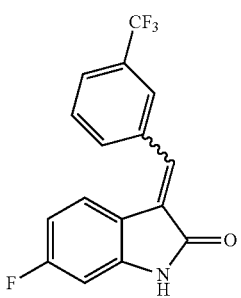 [SMILES: O=C1Nc2cc(F)ccc2C1=Cc1cccc(C(F)(F)F)c1]

Yield 24.0%, ¹HNMR (300 MHZ DMSO-d₆) δ 10.8 (s, 1H), 7.98 (d, J=6.9 Hz, 2H), 7.82 (d, J=7.5 Hz, 1H), 7.75 (t, J=7.8 Hz, 1H), 7.66 (s, 1H), 7.33 (dd, J1=14 Hz, J2=5.4 Hz, 1H), 6.66-6.71 (m, 2H);

¹³CNMR (75 MHz, DMSO-d₆), δ168.5, 164.9, 161.7, 145.2, 145, 135.4, 133.35, 133.31, 132.8, 129.9, 129.3, 128, 125.9, 125.7, 123.9, 123.7, 122.1, 116.9, 116.9, 107.7, 107.4, 98.5, 98.1;

More C atoms were detected in the 13C NMR data than the expected number. It is proposed that this may be due to isomerization during the scanning process which took place overnight, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.

(APCI): m/z, 307.9 [M+1]⁺.

(E)-6-Fluoro-3-(4-trifluoromethyl-benzylidene)-1,3-dihydro-indol-2-one (3-7)

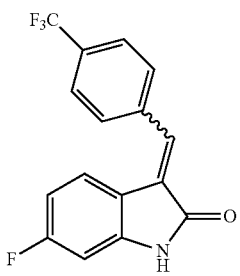 [SMILES: O=C1Nc2cc(F)ccc2C1=Cc1ccc(C(F)(F)F)cc1]

Yield 51.3%, ¹H NMR (300 MHZ DMSO-d₆) δ10.8 (br s, 1H), 7.87 (t, J=9 Hz, 4H), 7.63 (s, 1H), 7.41 (t, J=6.9 Hz, 1H), 6.63-6.70 (m, 2H); ¹³NMR (75 MHz, DMSO-d6) δ168.5, 165.0, 161.7, 145.2, 145.1, 138.5, 133.2, 129.8, 128.2, 125.6, 125.6, 124.3, 124.2, 116.8, 107.8, 107.5, 98.4, 98.1; MS (APCI): m/z 308.0 [M+H]⁺.

(E)-6-Fluoro-3-(3-trifluoromethoxyl-benzylidene)-1,3-dihydro-indol-2-one (3-8)

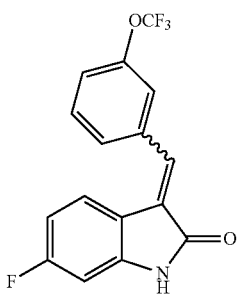 [SMILES: O=C1Nc2cc(F)ccc2C1=Cc1cccc(OC(F)(F)F)c1]

Yield 27.2%; ¹HNMR (300 MHz DMSO-d6) δ 10.8 (s, 1H), 7.74-7.64 (m, 3H), 7.61 (s, 1H), 7.50 (d, J=8.4 Hz, 1H), 7.39 (q, J=8.4 Hz, 1H), 6.73-6.64 (m, 2H);

¹³CNMR (75 MHz, DMSO-d6) δ 168.6, 165.0, 161.7, 148.5, 145.2, 145.0, 136.6, 133.2, 130.9, 128.0, 127.9, 124.0, 123.9, 121.9, 121.7, 121.4, 116.9, 107.7, 107.4, 98.5, 98.1;

More C atoms were detected in the 13C NMR data than the expected number. It is proposed that this may be due to isomerization during the scanning process which took place overnight, resulting in a mixture of isomers (The isomerization could be identified by comparing the proton spectrum which is done before carbon spectrum and the one which is done after the carbon spectrum). The presence of F atoms in the compound may have caused splitting of the peaks and contributed to the additional number of peaks in the spectrum.

MS (APCI): 324.5 m/z [M+1]⁺.

(E)-6-Fluoro-3-(3-methanesulfonyl-benzylidene)-1,3-dihydro-indol-2-one (3-9)

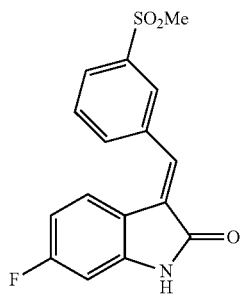 [SMILES: CS(=O)(=O)c1cccc(/C=C2/C(=O)Nc3cc(F)ccc32)c1]

Yield 44.1%; ¹H NMR (300 MHz DMSO-d6) δ 10.85 (s, 1H), 8.22 (s, 1H), 8.02 (t, J=6.3 Hz, 2H), 7.80 (t, J=7.8 Hz, 1H), 7.67 (s, 1H), 7.29 (t, J=8.4 Hz, 1H), 6.73-6.64 (m, 2H), 3.29 (s, 3H); ¹³NMR (75 MHz, DMSO-d6) 168.5, 145.2, 145.1, 141.3, 135.5, 133.9, 133.1, 130.0, 128.1, 127.5, 127.3, 124.1, 123.9, 116.9, 116.8, 107.8, 98.5, 98.1, 43.3; MS (APCI): m/z 318.4 [M+H]⁺.

* More C atoms were detected in the ¹³C NMR data than the expected number. It is proposed that this may be due to isomerization during the scanning process which took place overnight, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.

(E)-3-(6-Fluoro-2-oxo-1,2-dihydro-indol-3-ylidenemethyl)-N-methyl-benzenesulphonamide (3-10)

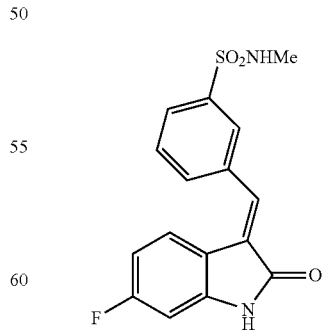

Yield 22.3%; ¹H NMR (400 MHz, DMSO-d6) δ 11.59 (s, 1H), 8.04-7.70 (m, 2H), 7.20-6.85 (m, 2H), 6.40 (d, J=74.8 Hz, 1H), 4.24 (s, 2H), 4.06 (q, J=7.0 Hz, 2H), 1.33 (dt, J=7.0 Hz, 3H); ¹³C NMR (101 MHz, DMSO-d6) δ 168.5, 164.6, 162.1, 145.2, 145.0, 139.9, 135.3, 134.8, 133.4, 133.4, 132.9, 129.9, 129.0, 127.9, 127.4, 126.7, 124.0, 123.9, 116.9, 107.8, 107.7, 107.5, 107.5, 98.4, 98.2, 28.6; MS (ACPI): m/z 331.3 [M−H]−.

(E)-3-(6-Fluoro-2-oxo-1,2-dihydro-indol-3-ylidenemethyl)-N-ethyl-benzenesulfonamide (3-11)

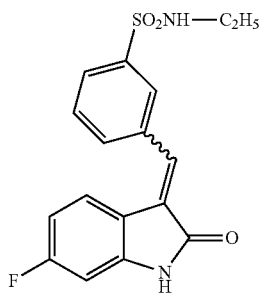

Yield 2.90% (after 3 steps), 1H NMR (400 MHz, DMSO-$d_6$), δ 10.85 (s, 1H), 8.04 (s, 1H), 7.88 (dd, J=17.31, 7.80 Hz, 2H), 7.74 (t, J=7.76 Hz, 1H), 7.70-7.66 (m, 1H), 7.64 (s, 1H), 7.35 (dd, J=8.53, 5.55 Hz, 1H), 6.73 (dd, J=9.12, 2.44 Hz, 1H), 6.65 (ddd, J=9.71, 8.64, 2.48 Hz, 1H), 2.82 (dd, J=6.62, 2.55 Hz, 2H), 0.98 (t, J=7.22 Hz, 3H); 13C NMR (100 MHz, DMSO-d6), δ 168.7, 164.7, 162.3, 145.2, 145.1, 141.2, 135.4, 133.6, 133.6, 133.0, 130.1, 128.1, 127.3, 126.6, 124.1, 124.0, 117.0, 117.0, 107.9, 107.6, 98.6, 98.4, 37.6, 14.8. MS (ESI): m/z 345.3 [M−H]−.

More C atoms were detected in the 13C NMR data than the expected number. It is proposed that this may be due to isomerization during the scanning process, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.

E/Z-3-(6-Fluoro-2-oxo-1,2-dihydro-indol-3-ylidenemethyl)-N-propyl-benzenesulfonamide (3-12)

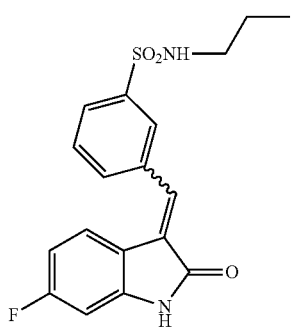

Yield 6.27%, 1H NMR (400 MHz, DMSO-$d_6$), δ 10.83 (s, 1H), 8.05 (s, 1H), 7.89 (dd, J=18.2, 7.5 Hz, 2H), 7.74 (t, J=7.8 Hz, 1H), 7.65 (s, 1H), 7.35 (dd, J=8.5, 5.6 Hz, 1H), 6.78-6.59 (m, 2H), 2.76 (td, J=14.1, 7.11 Hz, 2H), 1.50-1.29 (m, 2H), 0.79 (dt, J=7.4, 2.31 Hz, 3H); 13C NMR (100 MHz, DMSO-d6)*, δ 168.5, 167.1, 164.6, 162.1, 145.2, 145.1, 141.2, 140.7, 135.3, 134.7, 134.5, 133.5, 132.8, 129.9, 129.3, 129.1, 128.0, 127.5, 127.3, 127.2, 126.5, 124.0, 123.9, 116.9, 116.9, 107.8, 107.7, 107.5, 98.5, 98.2, 44.3, 22.4, 11.1. MS (ESI): m/z 359.3 [M−H]−.

More C atoms were detected in the 13C NMR data than the expected number. It is proposed that this may be due to isomerization during the scanning process, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.

(E)-3-(6-Fluoro-2-oxo-1,2-dihydro-indol-3-ylidenemethyl)-N-isopropyl-benzenesulfonamide (3-13)

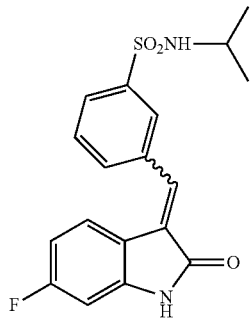

Yield 3.60%, 1H NMR (400 MHz, DMSO-$d_6$), δ 10.85 (s, 1H), 8.06 (s, 1H), 7.88 (dd, J=6.1, 1.6 Hz, 2H), 7.72 (dd, J=15.0, 7.3 Hz, 2H), 7.64 (s, 1H), 7.34 (dd, J=8.5, 5.6 Hz, 1H), 6.73 (dd, J=9.1, 2.3 Hz, 1H), 6.68-6.56 (m, 1H), 3.29 (dt, J=12.9, 6.3 Hz, 1H), 0.95 (d, J=6.5 Hz, 6H); 13C NMR (100 MHz, DMSO-d6)*, δ168.7, 164.696, 162.2, 145.2, 145.1, 142.5, 135.3, 133.7, 132.8, 130.0, 128.0, 127.2, 126.4, 124.0, 123.9, 117.0, 117.0, 107.8, 107.6, 98.6, 98.4, 45.4, 23.2. MS (ESI): m/z 359.3 [M−H]−.

* More C atoms were detected in the 13C NMR data than the expected number. It is proposed that this may be due to isomerization during the scanning process, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.

(E)-3-Benzylidene-5-fluoro-1,3-dihydro-indol-2-one (4-1)

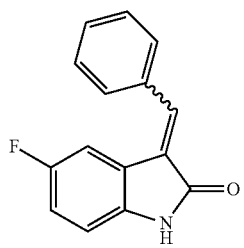 [SMILES: O=C1Nc2ccc(F)cc2C1=Cc1ccccc1]

Yield 87.4%, $^1$H NMR (300 MHZ DMSO-$d_6$) δ 10.64 (s, 1H), 7.79-7.61 (m, 3H), 7.52 (td, J=8.2, 4.7 Hz, 3H), 7.18 (dd, J=9.3, 2.1 Hz, 1H), 7.14-6.98 (m, 1H), 6.94-6.73 (m, 1H); $^{13}$C NMR (75 mHz, DMSO-d6) δ 168.9, 167.4, 159.0, 155.9, 139.6, 138.8, 137.9, 137.3, 134.3, 134.0, 132.4, 131.1, 130.4, 129.5, 129.2, 128.6, 127.8, 126.8, 122.2, 122.1, 116.9, 116.6, 111.3, 111.2, 109.8, 109.4; MS (APCI) m/z [M+H]$^+$ 240.3.

* More C atoms were detected in the $^{13}$C NMR data than the expected number. It is proposed that this may be due to isomerization during the scanning process, resulting in a mixture of isomers. The isomerization could be identified by comparing the proton spectrum which is done before carbon spectrum and the one which is done after the carbon spectrum.

(E)-5-Fluoro-3-(2-fluoro-benzylidene)-1,3-dihydro-indol-2-one (4-2)

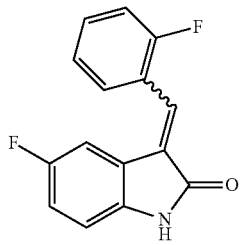 [SMILES: O=C1Nc2ccc(F)cc2C1=Cc1ccccc1F]

Yield 85.5%; $^1$H NMR (300 MHZ DMSO-$d_6$) δ 9.82 (s, 1H), 6.87 (t, J=7.5 Hz, 1H), 6.80-6.66 (m, 2H), 6.51 (dd, J=16.0, 8.3 Hz, 2H), 6.22 (dt, J=9.2, 2.4 Hz, 1H), 6.13-5.90 (m, 2H); $^{13}$C NMR (75 mHz, DMSO-d6) δ 167.7, 160.9, 158.5, 157.6, 155.3, 139.1, 132.1, 132.0, 130.1, 129.2, 128.8, 124.5, 121.6, 121.4, 121.3, 121.2, 116.7, 116.4, 116.0, 115.7, 110.7, 110.6, 109.5, 109.2; MS (APCI) m/z [M+H]$^+$ 258.3.

* More C atoms were detected in the $^{13}$C NMR data than the expected number. It is proposed that this may be due to isomerization during the scanning process, resulting in a mixture of isomers. The isomerization could be identified by comparing the proton spectrum which is done before carbon spectrum and the one which is done after the carbon spectrum.

(E)-5-Fluoro-3-(3-fluoro-benzylidene)-1,3-dihydro-indol-2-one (4-3)

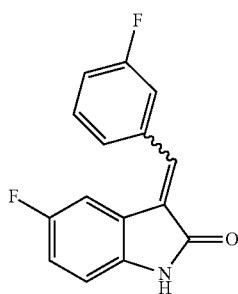 [SMILES: O=C1Nc2ccc(F)cc2C1=Cc1cccc(F)c1]

Yield 33.4%; $^1$H NMR (300 MHZ, DMSO-$d_6$) δ10.66 (s, 1H), 7.66 (s, 1H), 7.62-7.46 (m, 3H), 7.32 (s, 1H), 7.11 (d, J=8.3 Hz, 2H), 6.86 (s, 1H); $^{13}$C NMR (75 mHz, DMSO-d6) δ 168.9, 164.3, 161.1, 159.2, 156.1, 140.0, 137.0, 136.9, 136.3, 131.5, 131.4, 128.9, 125.6, 122.1, 122.0, 117.4, 117.3, 117.1, 117.1, 116.6, 116.3, 111.5, 111.4, 110.2, 109.8; MS (APCI) m/z [M+H]$^+$ 258.2.

* More C atoms were detected in the $^{13}$C NMR data than the expected number. It is proposed that this may be due to isomerization during the scanning process, resulting in a mixture of isomers. The isomerization could be identified by comparing the proton spectrum which is done before carbon spectrum and the one which is done after the carbon spectrum.

(E)-5-Fluoro-3-(4-fluoro-benzylidene)-1,3-dihydro-indol-2-one (4-4)

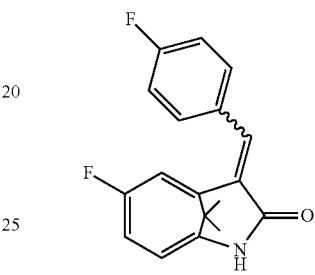

Yield 53.6%, $^1$H NMR (300 MHZ DMSO-$d_6$), δ10.64 (s, 1H), 7.76 (dd, J=8.1, 5.8 Hz, 2H), 7.67 (s, 1H), 7.37 (t, J=8.7 Hz, 2H), 7.18 (dd, J=9.2, 2.0 Hz, 1H), 7.13-7.03 (m, 1H), 6.86 (dd, J=8.5, 4.6 Hz, 1H); $^{13}$C NMR (75 mHz, DMSO-d6) δ 168.5, 164.3, 161.0, 158.6, 155.5, 139.2, 136.3, 131.8, 131.7, 130.4, 130.4, 127.3, 121.7, 121.6, 116.6, 116.3, 116.1, 115.8, 110.9, 110.8, 109.4, 109.1; MS (APCI) m/z [M+H]$^+$ 258.3.

* More C atoms were detected in the $^{13}$C NMR data than the expected number. It is proposed that this may be due to isomerization during the scanning process, resulting in a mixture of isomers. The isomerization could be identified by comparing the proton spectrum which is done before carbon spectrum and the one which is done after the carbon spectrum.

(E)-5-Fluoro-3-(2-methyl-benzylidene)-1,3-dihydro-indol-2-one (4-5)

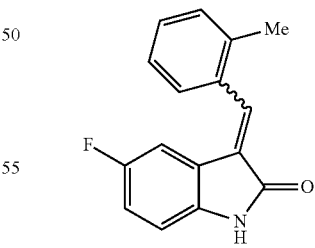

Yield 50.5%; $^1$H NMR (300 MHZ DMSO-$d_6$) δ 10.65 (s, 1H), 7.76 (s, 1H), 7.53 (d, J=7.2 Hz, 1H), 7.46-7.25 (m, 3H), 7.06 (dt, J=9.2, 2.3 Hz, 1H), 6.85 (dd, J=8.5, 4.6 Hz, 1H), 6.78-6.67 (m, 1H), 2.40-2.16 (m, 3H); $^{13}$C NMR (75 mHz, DMSO-d6) δ 168.3, 158.7, 155.6, 139.1, 136.9, 136.5, 133.4, 130.5, 129.8, 128.2, 128.1, 126.0, 122.1, 122.0, 116.5, 116.2, 110.9, 110.8, 109.4, 109.0, 19.4; MS (APCI) m/z [M+H]$^+$ 254.2.

* More C atoms were detected in the $^{13}$C NMR data than the expected number. It is proposed that this may be due to isomerization during the scanning process, resulting in a mixture of isomers. The isomerization could be identified by comparing the proton spectrum which is done before carbon spectrum and the one which is done after the carbon spectrum.

(E)-5-Fluoro-3-(3-methyl-benzylidene)-1,3-dihydro-indol-2-one (4-6)

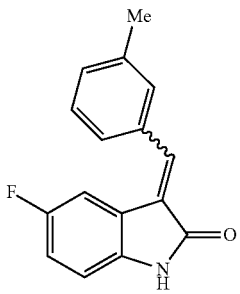 [SMILES: Cc1cccc(C=C2C(=O)Nc3ccc(F)cc32)c1]

Yield 38.7%, $^1$H NMR (300 MHZ DMSO-d$_6$) δ 10.63 (s, 1H), 7.67 (s, 1H), 7.54-7.39 (m, 3H), 7.32 (d, J=7.3 Hz, 1H), 7.19 (dd, J=9.4, 2.3 Hz, 1H), 7.09 (dt, J=9.2, 2.4 Hz, 1H), 6.86 (dd, J=8.5, 4.7 Hz, 1H), 2.37 (s, 3H); $^{13}$C NMR (75 mHz, DMSO-d6) δ 168.8, 158.9, 155.8, 139.5, 138.4, 137.8, 134.2, 130.9, 129.9, 129.0, 127.6, 126.4, 122.2, 122.1, 116.7, 116.4, 111.1, 111.0, 109.7, 109.3, 21.1; MS (APCI) m/z [M+H]$^+$ 254.1.

* More C atoms were detected in the $^{13}$C NMR data than the expected number. It is proposed that this may be due to isomerization during the scanning process, resulting in a mixture of isomers. The isomerization could be identified by comparing the proton spectrum which is done before carbon spectrum and the one which is done after the carbon spectrum.

(E)-5-Fluoro-3-(4-methyl-benzylidene)-1,3-dihydro-indol-2-one (4-7)

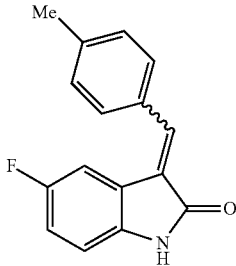 [SMILES: Cc1ccc(C=C2C(=O)Nc3ccc(F)cc32)cc1]

Yield 63.2%, $^1$H NMR (300 MHZ DMSO-d$_6$) δ 10.62 (s, 1H), 7.66 (s, 1H), 7.58 (d, J=7.8 Hz, 2H), 7.34 (d, J=7.8 Hz, 2H), 7.25 (dd, J=9.3, 2.0 Hz, 1H), 7.06 (dt, J=9.2, 2.3 Hz, 1H), 6.85 (dd, J=8.5, 4.7 Hz, 1H), 2.37 (s, 3H); $^{13}$C NMR (75 mHz, DMSO-d6) δ 168.7, 158.7, 155.6, 140.2, 139.1, 137.7, 131.1, 129.5, 129.4, 126.7, 122.0, 121.9, 116.4, 116.1, 110.8, 110.7, 109.4, 109.0, 21.1; MS (APCI) m/z [M+H]$^+$ 254.2.

* More C atoms were detected in the $^{13}$C NMR data than the expected number. It is proposed that this may be due to isomerization during the scanning process, resulting in a mixture of isomers. The isomerization could be identified by comparing the proton spectrum which is done before carbon spectrum and the one which is done after the carbon spectrum.

(E)-5-Fluoro-3-(3-methoxy-benzylidene)-1,3-dihydro-indol-2-one (4-8)

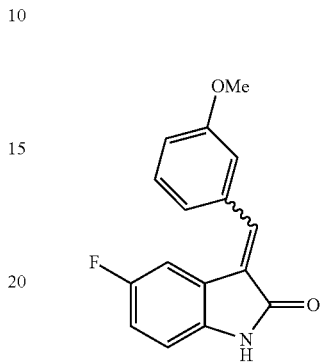

Yield 61.7%; $^1$H NMR (300 MHz DMSO-d$_6$), δ10.64 (s, 1H), 7.68 (s, 1H), 7.47 (t, J=7.85 Hz, 1H), 7.33-7.15 (m, 3H), 7.15-7.00 (m, 2H), 6.87 (dd, J=8.4, 4.6 Hz, 1H), 3.80 (s, 3H); $^{13}$C NMR (75 mHz, DMSO-d6) δ168.5, 159.4, 158.6, 155.5, 139.3, 137.3, 135.3, 130.0, 127.5, 121.3, 116.6, 116.3, 115.8, 114.3, 109.3, 55.2; MS (APCI) m/z [M+H]$^+$ 270.1.

* More C atoms were detected in the $^{13}$C NMR data than the expected number. It is proposed that this may be due to isomerization during the scanning process, resulting in a mixture of isomers. The isomerization could be identified by comparing the proton spectrum which is done before carbon spectrum and the one which is done after the carbon spectrum.

(E)-5-Fluoro-3-(2-trifluoromethyl-benzylidene)-1,3-dihydro-indol-2-one (4-9)

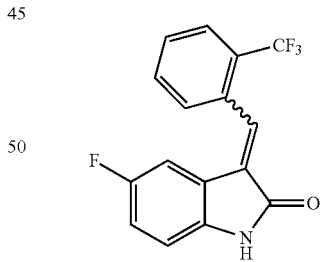

Yield 42.6%; $^1$H NMR (300 MHZ DMSO-d$_6$) δ 10.74 (s, 1H), 7.92 (d, J=7.3 Hz, 1H), 7.87-7.63 (m, 4H), 7.07 (t, J=8.1 Hz, 1H), 6.94-6.75 (m, 1H), 6.43 (d, J=7.9 Hz, 1H); $^{13}$C NMR (75 mHz, DMSO-d6) δ 167.7, 158.6, 155.5, 139.5, 133.0, 132.6, 130.1, 130.0, 127.2, 126.5, 126.5, 122.0, 121.4, 121.3, 117.2, 116.8, 111.2, 111.1, 109.7, 109.3; MS (APCI) m/z [M+H]$^+$ 308.2.

* More C atoms were detected in the $^{13}$C NMR data than the expected number. It is proposed that this may be due to isomerization during the scanning process, resulting in a mixture of isomers. The isomerization could be identified by comparing the proton spectrum which is done before carbon spectrum and the one which is done after the carbon spectrum.

(E)-5-Fluoro-3-(3-trifluoromethyl-benzylidene)-1,3-dihydro-indol-2-one (4-10)

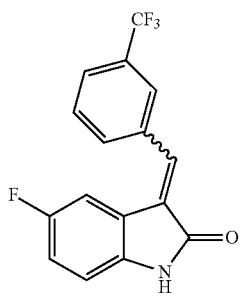 [SMILES: O=C1Nc2ccc(F)cc2C1=Cc1cccc(C(F)(F)F)c1]

Yield 7.1%, $^1$HNMR (300 MHZ DMSO-d$_6$) δ 10.7 (s, 1H), 8.00 (d, J=9.6 Hz, 1H), 7.84-7.73 (m, 2H), 7.11-6.99 (m, 2H), 6.87 (q, J=4.5 Hz, 1H);

$^{13}$CNMR (75 mHz, DMSO-d6) δ168.3, 158.7, 155.5, 139.6, 135.4, 135.2, 132.9, 130.0, 129.8, 129.4, 128.9, 126.2, 125.8, 125.7, 122.1, 121.4, 121.3, 117.1, 116.8, 111.1, 111.0, 109.4, 109.1;

MS (APCI) m/z [m+1]$^+$ 308.1.

(E)-5-Fluoro-3-(2-trifluoromethyl-benzylidene)-1,3-dihydro-indol-2-one (4-11)

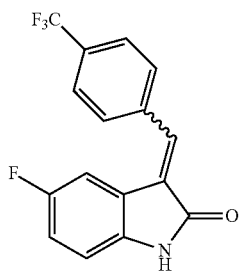 [SMILES: O=C1Nc2ccc(F)cc2C1=Cc1ccc(C(F)(F)F)cc1]

Yield 3.3%, $^1$H NMR (300 MHZ DMSO-d$_6$) δ 10.70 (s, 1H), 7.88 (s, 4H), 7.72 (s, 1H), 7.09 (t, J=9.0 Hz, 2H), 6.87 (dd, J=8.0, 4.6 Hz, 1H); $^{13}$C NMR (75 mHz, DMSO-d6) δ 168.2, 158.7, 155.6, 139.6, 138.3, 135.3, 129.9, 129.4, 129.0, 125.7, 125.7, 121.4, 121.2, 117.2, 116.9, 111.1, 111.0, 109.8, 109.5; MS (APCI) m/z [M+H]$^+$ 308.1.

* More C atoms were detected in the $^{13}$C NMR data than the expected number. It is proposed that this may be due to isomerization during the scanning process, resulting in a mixture of isomers. The isomerization could be identified by comparing the proton spectrum which is done before carbon spectrum and the one which is done after the carbon spectrum.

(E)-3-(3,4-Difluoro-benzylidene)-5-fluoro-1,3-dihydro-indol-2-one (4-12)

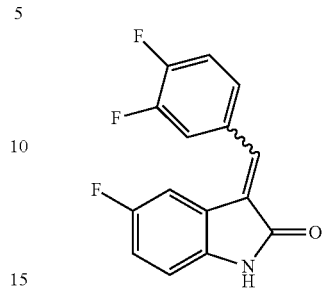

Yield: 36%; $^1$H NMR (300 MHz, in DMSO-d$_6$): δ 10.72 (s, 1H), 8.83 (q, J=8.7 Hz, 1H), 8.00 (s, 1H), 7.84 (s, 1H), 7.61-7.49 (m, 2H), 7.05 (td, J=9.0 Hz, 1H); $^{13}$C NMR (75 MHz, in DMSO-d$_6$): δ 167.0, 159.4, 156.3, 137.1, 135.9, 131.4, 131.3, 131.3, 130.4, 127.1, 126.0, 125.9, 120.2, 119.9, 117.4, 117.2, 115.6, 115.3, 110.3, 110.2, 107.5, 107.2; MS (APCI): m/z 276.2 [M+H].

* More C atoms were detected in the $^{13}$C NMR data than the expected number. It is proposed that this may be due to isomerization during the scanning process, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.

(E)-5-Fluoro-3-(3-trifluoromethoxy-benzylidene)-1,3-dihydro-indol-2-one (4-13)

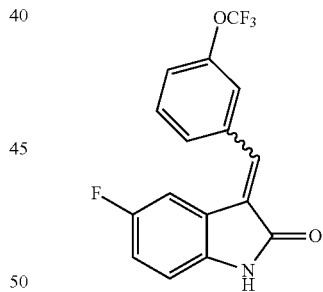

Yield 68.7%; $^1$HNMR (300 MHz DMSO-d6) δ 10.7 (s, 1H), 7.75-7.66 (m, 4H), 7.52 (d, J=7.8 Hz, 1H), 7.15-7.07 (m, 2H), 6.88 (t, J=8.4, 1H);

$^{13}$CNMR (75 MHz, DMSO-d6) δ 168.2, 167.0, 158.6, 155.5, 148.4, 148.1, 139.5, 137.3, 136.3, 136.3, 135.7, 135.3, 131.2, 131.0, 130.1, 128.7, 128.2, 128.0, 126.0, 125.9, 123.3, 122.8, 122.3, 121.7, 121.4, 121.3, 117.0, 116.7, 115.8, 115.5, 111.0, 110.9, 110.3, 110.2, 109.5, 109.2, 107.7; More C atoms were detected in the 13C NMR data than the expected number. It is proposed that this may be due to isomerization during the scanning process which took place overnight, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.

(E)-5-Fluoro-3-(3-methanesulfonyl-benzylidene)-1,3-dihydro-indol-2-one (4-14)

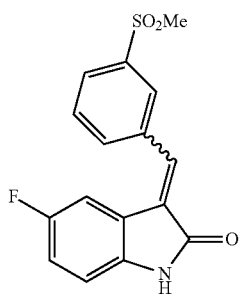 [SMILES: CS(=O)(=O)c1cccc(C=C2C(=O)Nc3ccc(F)cc32)c1]

Yield 30.0%, $^1$H NMR (300 MHz DMSO-d6) δ 10.71 (s, 1H), 8.25 (s, 1H), 8.08-8.00 (m, 1H), 7.83 (t, J=7.8 Hz, 1H), 7.76 (s, 1H), 7.13 (t, J=8.7 Hz, 2H), 6.93-6.84 (m, 1H), 3.29 (s, 3H); 13NMR (75 MHz, DMSO-d6) δ 168.2, 158.7, 155.6, 141.4, 139.6, 135.2, 134.1, 130.1, 129.0, 127.8, 127.4, 121.3, 121.2, 117.2, 116.9, 111.1, 111.0, 109.7, 109.3, 43.2; MS (APCI): m/z 318.2 [M+H]$^+$.

* More C atoms were detected in the $^{13}$C NMR data than the expected number. It is proposed that this may be due to isomerization during the scanning process which took place overnight, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.

(E) 3-(5-Fluoro-2-oxo-1,2-dihydro-indol-3-ylidenemethyl)-benzonitrile (4-15)

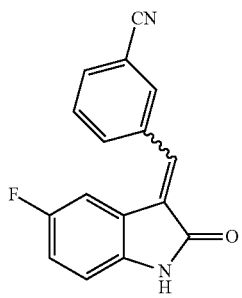 [SMILES: N#Cc1cccc(C=C2C(=O)Nc3ccc(F)cc32)c1]

Yield 56.8%; $^1$HNMR (300 MHz DMSO-d6) δ 10.7 (s, 1H), 8.85 (d, 1H), 8.43 (d, J=8.1 Hz, 1H), 7.87 (d, J=7.2 Hz, 2H), 7.69-7.58 (m, 2H), 7.07 (td, J=9.3 Hz, 1H), 6.81 (q, J=4.5 Hz, 1H);
$^{13}$CNMR (75 MHz, DMSO-d6) δ 168.2, 166.9, 159.5, 156.4, 139.5, 137.4, 136.2, 135.5, 135.4, 134.8, 134.7, 134.6, 133.4, 133.2, 132.7, 130.1, 129.5, 129.1, 129.0, 128.5, 125.8, 125.6, 121.3, 121.2, 118.6, 118.3, 117.2, 116.8, 116.1, 115.8, 112.1, 111.3, 111.1, 111.0, 110.5, 110.4, 109.7, 109.3, 107.8, 107.5; More C atoms were detected in the 13C NMR data than the expected number. It is proposed that this may be due to isomerization during the scanning process which took place overnight, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.

MS (APCI): m/z 265.3 [M+1]$^+$.

(E)-3-(5-Fluoro-2-oxo-1,2-dihydro-indol-3-ylidenemethyl)-N-methyl-benzenesulphonamide (4-16)

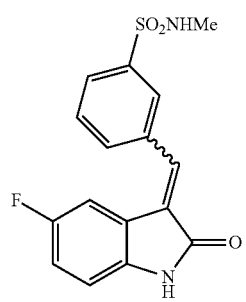

Yield 15.6%; $^1$H NMR (400 MHz, DMSO-d6) δ 10.70 (s, 1H), 8.07 (s, 1H), 7.94 (d, J=7.6 Hz, 1H), 7.88 (dd, J=6.7 Hz, 1H), 7.79 (d, J=7.7 Hz, 1H), 7.76 (d, J=2.1 Hz, 1H), 7.61 (s, 1H), 7.16-7.03 (m, 2H), 6.88 (dd, J=8.5 Hz, 1H), 2.48 (d, J=9.5 Hz, 3H); $^{13}$C NMR (101 MHz, DMSO-d6) δ 168.2, 166.9, 158.3, 155.9, 139.9, 139.5, 139.5, 137.3, 136.4, 135.5, 135.0, 134.3, 133.1, 130.0, 129.7, 129.2, 128.8, 128.8, 128.1, 128.1, 127.9, 127.6, 126.7, 121.3, 121.3, 117.0, 116.8, 115.8, 115.6, 111.0, 111.0, 110.3, 110.2, 109.6, 109.3, 107.8, 107.6, 30.6, 28.6, 28.5; MS (ACPI): m/z 333.3 [M+H]$^+$;

* More C atoms were detected in $^{13}$C NMR spectrum than expected. The presence of F atoms in the compound may have caused splitting of the peaks and contribute to an additional number of peaks.

(E)-3-Benzylidene-6-methoxy-1,3-dihydro-indol-2-one (5-1)

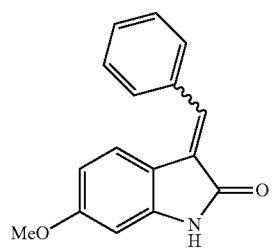 [SMILES: COc1ccc2c(c1)NC(=O)C2=Cc1ccccc1]

Yield 9.1%, $^1$HNMR (300 MHZ DMSO-d$_6$) δ 10.6 (br s, 1H), 7.67 (d, J=7.2 Hz, 2H), 7.52 (d, J=6.9 Hz, 2H), 7.46-7.48 (m, 2H), 7.45 (s, 1H), 6.42 (d, J=6 Hz, 2H), 3.75 (s, 3H);
$^{13}$CNMR (75 MHz, DMSO-d$_6$) δ 169.2, 161.1, 144.6, 134.7, 132.4, 129.2, 129.1, 128.6, 127.2, 123.5, 113.6, 106.5, 96.4, 55.2; MS (APCI): m/z, 270.0 [M+1]$^+$.

(E)-3-(2-Fluoro-benzylidene)-6-methoxy-1,3-dihydro-indol-2-one (5-2)

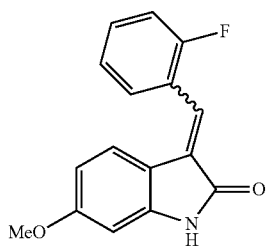 [SMILES: COc1ccc2c(c1)NC(=O)C2=Cc1ccccc1F]

Yield 27.8%, ¹HNMR (300 MHZ DMSO-d$_6$) δ 10.6 (s, 1H), 7.74 (t, J=7.5 Hz, 1H), 7.47-7.54 (m, 1H), 7.32-7.36 (m, 2H), 7.34 (s, 1H), 7.19 (d, J=9 Hz, 1H), 6.42 (m, 2H), 3.76 (s, 3H); ¹³CNMR (75 MHz, DMSO-d$_6$) δ168.7, 161.4, 161.2, 144.8, 131.5, 130.3, 129.3, 124.6, 123.9, 122.5, 115.9, 113.4, 106.7, 96.4, 55.3; MS (APCI): m/z, 270.0 [M+1]⁺.

(E)-3-(3-Fluoro-benzylidene)-6-methoxy-1,3-dihydro-indol-2-one (5-3)

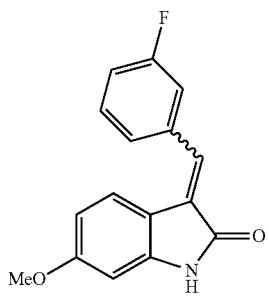 [SMILES: COc1ccc2c(c1)NC(=O)C2=Cc1cccc(F)c1]

Yield 25.2%, ¹HNMR (300 MHZ DMSO-d$_6$) δ 10.6 (s, 1H, NH), 7.46-7.56 (m, 3H), 7.41 (s, 1H), 7.40 (d, J=6 Hz, 1H), 7.26-7.28 (m, 1H), 6.44 (m, 2H), 3.76 (s, 3H); 13CNMR (75 MHz, DMSO-d6) δ 137.2, 137.1, 130.7, 130.7, 128.1, 125.1, 123.7, 116.1, 115.8, 115.5, 113.3, 106.6, 96.5, 55.3; MS (APCI): m/z, 270.0 [M+1]⁺.

(E)-3-(4-Fluorobenzylidene)-6-methoxy-1,3-dihydro-indol-2-one (5-4)

(5-4)

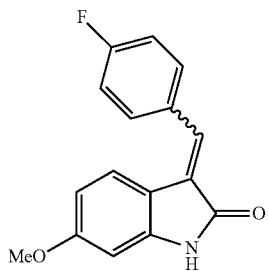 [SMILES: COc1ccc2c(c1)NC(=O)C2=Cc1ccc(F)cc1]

Yield: 19.26%, ¹H NMR (300 MHz, in DMSO-d$_6$): 10.6 (br s, 1H), 7.73 (dd, J$_1$=14 Hz, J$_2$=5.7 Hz, 2H), 7.43 (d, J=8.7 Hz, 1H), 7.42 (s, 1H), 7.33 (t, J=8.7 Hz, 2H), 6.41-6.44 (m, 2H), 3.75 (s, 3H); ¹³NMR (75 MHz, DMSO-d6) δ169.2, 161.1, 144.7, 131.5, 131.4, 131.3, 131.1, 127.1, 123.5, 115.7, 113.5, 106.5, 96.4, 55.2; MS (APCI): m/z 270.0 [M+H]⁺.

(E) 6-Methoxy-3-(2-trifluoromethyl-benzylidene)-1,3-dihydro-indol-2-one (5-5)

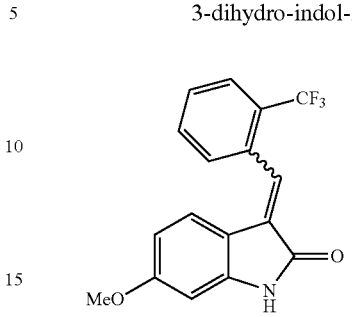

Yield 20.6%; ¹HNMR (300 MHZ DMSO-d$_6$), δ 10.6 (br s, 1H), 7.85 (d, J=7.8 Hz, 1H), 7.70-7.75 (m, 2H), 7.64 (t, J=7.2 Hz, 1H), 7.48 (s, 1H), 6.73 (d, J=8.7 Hz, 1H), 6.45 (s, 1H), 6.30 (dd, J1=8.4 Hz, J2=1.5 Hz, 1H), 3.69 (s, 3H); ¹³NMR (75 MHz, DMSO-d$_6$), δ169.2, 161.9, 145.1, 133.7, 133.2, 130.6, 130.2, 129.9, 128.1, 127.6, 127.2, 126.7, 124.2, 122.5, 113.5, 107.2, 97.2, 55.7; MS (APCI): m/z 320.0 [M+H]⁺.

(E)-6-Methoxy-3-(3-trifluoromethyl-benzylidene)-1,3-dihydro-indol-2-one (5-6)

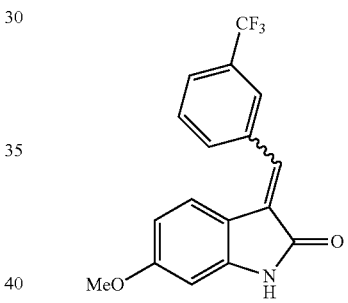

Yield 20.3%, ¹H NMR (300 MHZ DMSO-d$_6$) δ 10.6 (br s, 1H), 7.97 (d, J=7.2 Hz, 2H), 7.71-7.81 (m, 2H), 7.49 (s, 1H), 7.29 (d, J=8.1 Hz), 6.39-6.43 (m, 2H), 3.75 (s, 3H); ¹³C NMR (75 MHz, DMSO-d$_6$), δ168.9, 161.4, 145, 135.9, 132.8, 130.3, 129.8, 129.6, 129.2, 128.6, 125.7, 125.6, 123.4, 113.2, 106.5, 96.6, 55.3; MS (APCI): m/z, 320.0 [M+H]⁺.

(E)-6-Methoxy-3-(4-trifluoromethyl-benzylidene)-1,3-dihydro-indol-2-one (5-7)

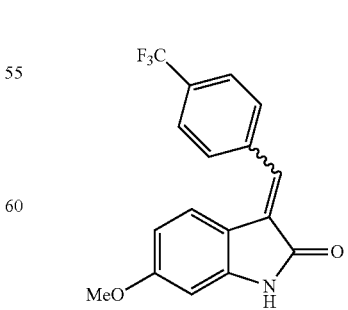

Yield 18.1%, ¹H NMR (300 MHZ DMSO-d$_6$) δ 10.6 (br s, 1H), 7.86 (t, J=9 Hz, 4H), 7.46 (s, 1H), 7.37 (d, J=9 Hz, 1H), 6.41-6.44 (m, 2H), 3.75 (s, 3H); $^{13}$NMR (75 MHz, DMSO-d6) δ168.5, 165.0, 161.7, 145.2, 145.1, 138.5, 133.2, 129.8, 128.2, 125.6, 125.6, 124.3, 124.2, 116.8, 107.8, 107.5, 98.4, 98.1; MS (APCI): m/z 320.0 [M+H]$^+$.

(E)-3-(6-Methoxy-2-oxo-1,2-dihydro-indol-3-ylidenemethyl)-N-methyl-benzenesulphonamide (5-8)

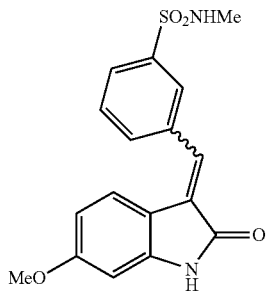

Yield 55.2%; $^1$H NMR (400 MHz, DMSO-d6) δ 10.62 (s, J=9.8 Hz, 1H), 8.05 (s, 1H), 7.91 (d, J=7.6 Hz, 1H), 7.83 (dd, J=6.7 Hz, 1H), 7.73 (m, J=9.8 Hz, 1H), 7.56 (d, J=4.7 Hz, 1H), 7.48 (s, J=11.6 Hz, 1H), 7.34 (t, J=6.6 Hz, 1H), 6.46-6.38 (m, 2H), 3.78 (s, 3H), 2.46 (d, J=4.4 Hz, 1H); $^{13}$C NMR (101 MHz, DMSO-d6), δ 168.9, 161.5, 145.0, 139.8, 135.8, 132.9, 130.3, 129.8, 128.6, 127.0, 126.6, 123.6, 113.2, 106.5, 96.7, 55.3, 28.6; MS (ACPI): m/z 343.3 [M−H]

(Z)-3-Benzylidene-4,5-difluoro-1,3-dihydro-indol-2-one (6-1)

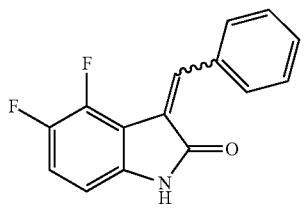 [SMILES: O=C1Nc2ccc(F)c(F)c2C1=Cc1ccccc1]

Yield 74.6%; $^1$H NMR (300 MHZ DMSO-d$_6$) δ 10.84 (s, 1H), 8.41-8.10 (m, 2H), 7.80 (s, 1H), 7.46 (d, J=4.2 Hz, 3H), 7.25 (dd, J=19.4, 8.5 Hz, 1H), 6.62 (dd, J=8.1, 2.5 Hz, 1H); $^{13}$NMR (75 MHz, DMSO-d$_6$) δ 168.4, 166.2, 147.4, 147.2, 147.0, 146.8, 144.1, 143.8, 143.7, 142.4, 142.2, 140.2, 140.1, 138.9, 137.9, 137.9, 134.9, 133.5, 132.1, 131.1, 130.1, 130.0, 129.8, 128.2, 127.9, 125.0, 124.3, 118.2, 117.9, 117.2, 117.0, 113.0, 112.8, 110.1, 109.9, 105.6, 105.2. MS (APCI): m/z 258.2 [M+H]$^+$.

* More C atoms were detected in the $^{13}$C NMR data than the expected number. It is proposed that this may be due to isomerization during the scanning process, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.

(Z)-4,5-Difluoro-3-(2-fluoro-benzylidene)-1,3-dihydro-indol-2-one (6-2)

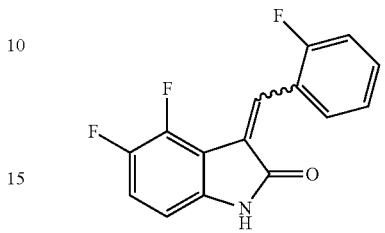

Yield 36.3%; $^1$H NMR (300 MHZ DMSO-d$_6$) δ 10.85 (s, 1H), 8.46 (t, J=7.8 Hz, 1H), 7.91-7.74 (m, 1H), 7.51 (dd, J=13.4, 6.3 Hz, 1H), 7.40-7.12 (m, 3H), 6.61 (dd, J=8.4, 3.2 Hz, 1H); $^{13}$NMR (75 MHz, DMSO-d$_6$) δ165.7, 162.0, 158.7, 147.2, 146.8, 144.1, 143.9, 143.6, 143.5, 138.2, 132.9, 132.7, 132.0, 126.7, 123.8, 123.8, 121.3, 121.1, 117.8, 117.5, 115.3, 115.0, 112.1, 105.3. MS (APCI): m/z 276.0 [M+H]$^+$.

* More C atoms were detected in the $^{13}$C NMR data than the expected number. It is proposed that this may be due to isomerization during the scanning process, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.

(Z)-4,5-Difluoro-3-(3-fluoro-benzylidene)-1,3-dihydro-indol-2-one (6-3)

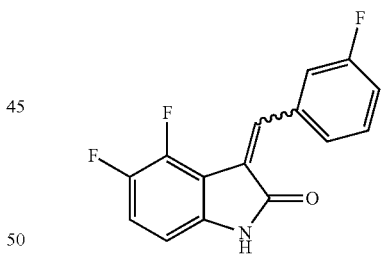

Yield 52.3%; $^1$H NMR (300 MHZ DMSO-d$_6$) δ 10.90 (s, 1H), 8.38 (d, J=11.13 Hz, 1H), 7.99-7.68 (m, 2H), 7.49 (dd, J=14.60, 8.07 Hz, 1H), 7.39-7.19 (m, 2H), 6.79-6.48 (m, 1H); $^{13}$NMR (75 MHz, DMSO-d$_6$) δ 168.0, 166.0, 163.1, 159.9, 147.2, 143.8, 140.4, 138.1, 137.2, 135.5, 129.9, 129.7, 128.7, 126.1, 125.4, 118.5, 118.2, 117.9, 117.5, 117.3, 116.5, 116.1, 112.6, 109.7, 109.5, 105.6, 105.2; MS (APCI): m/z 276.0 [M+H]$^+$.

* More C atoms were detected in the $^{13}$C NMR data than the expected number. It is proposed that this may be due to isomerization during the scanning process, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.

(Z)-4,5-Difluoro-3-(4-fluoro-benzylidene)-1,3-dihydro-indol-2-one (6-4)

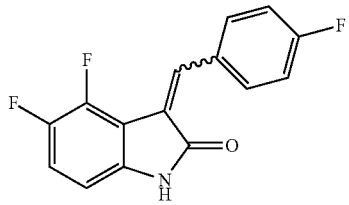 [SMILES: O=C1Nc2ccc(F)c(F)c2C1=Cc1ccc(F)cc1]

Yield 88.6%; $^1$H NMR (300 MHZ DMSO-d$_6$) δ 10.84 (s, 1H), 8.44-8.26 (m, 2H), 7.75 (s, 1H), 7.33-7.13 (m, 3H), 6.59 (d, J=6.08 Hz, 1H); $^{13}$NMR (75 MHz, DMSO-d$_6$) δ 168.231, 166.211, 165.036, 161.710, 146.905, 143.762, 140.955, 140.806, 137.816, 137.732, 134.922, 134.806, 132.577, 132.510, 132.466, 132.400, 131.351, 130.129, 130.092, 124.583, 117.077, 116.821, 115.322, 115.035, 114.746, 112.902, 112.748, 105.144; MS (APCI): m/z 276.0 [M+H]$^+$.

* More C atoms were detected in the $^{13}$C NMR data than the expected number. It is proposed that this may be due to isomerization during the scanning process, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.

(E/Z)-4,5-Difluoro-3-(2-trifluoromethyl-benzylidene)-1,3-dihydro-indol-2-one (6-5)

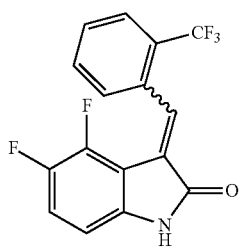 [SMILES: O=C1Nc2ccc(F)c(F)c2C1=Cc1ccccc1C(F)(F)F]

Yield 54.1%, $^1$H NMR (300 MHZ DMSO-d$_6$) δ 10.90 (d, J=53.9 Hz, 1H), 8.00-7.46 (m, 5H), 7.40-7.22 (m, 1H), 6.76-6.58 (m, 1H); $^{13}$NMR (75 MHz, DMSO-d$_6$) δ167.4, 165.5, 147.1, 144.1, 140.3, 140.2, 138.7, 138.6, 136.0, 135.9, 134.0, 133.9, 132.0, 131.9, 131.8, 130.9, 130.8, 129.6, 129.4, 127.9, 127.3, 127.1, 126.8, 126.7, 126.4, 126.0, 125.9, 125.6, 125.5, 125.4, 125.4, 122.3, 119.1, 118.8, 118.4, 118.2, 111.6, 111.4, 109.2, 109.0, 106.0, 105.9, 105.7. MS (APCI): m/z 326.1 [M+H]$^+$.

* More C atoms were detected in the $^{13}$C NMR data than the expected number. The presence of F atoms in the compound may have caused splitting of the peaks and contributed to the additional number of peaks in the spectrum.

(Z)-4,5-Difluoro-3-(3-trifluoromethyl-benzylidene)-1,3-dihydro-indol-2-one (6-6)

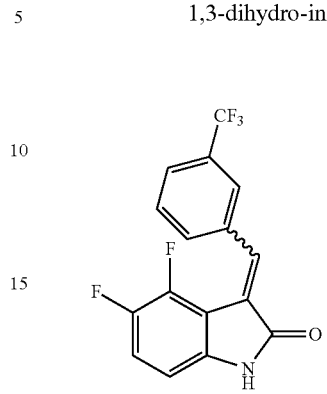

Yield 51.7%, $^1$HNMR (300 MHZ DMSO-d$_6$), δ 10.9 (s, 1H), 8.75 (s, 1H), 8.32 (d, J=7.2 Hz, 1H), 7.83 (s, 1H), 7.76 (d, J=7.2 Hz, 1H), 7.65 (s, J=7.2 Hz, 1H), 7.28 (q, J=8.4 Hz, 1H), 6.63 (d, J=6.3 Hz, 1H);
$^{13}$CNMR (75 MHz, DMSO-d$_6$) δ 168.0, 166.1, 147.6, 147.4, 147.3, 147.0, 146.9, 144.2, 144.0, 143.9, 143.7, 140.5, 140.4, 140.1, 139.9, 138.3, 138.2, 136.7, 136.1, 135.8, 134.2, 133.8, 129.6, 129.2, 129.0, 128.9, 128.8, 128.5, 128.3, 128.0, 128.0, 127.0, 126.9, 126.6, 126.3, 126.1, 126.0, 122.4, 118.8, 118.5, 117.8, 117.6, 112.6, 112.4, 109.7, 109.5, 105.9, 105.9, 105.8, 105.4;

More C atoms were detected in the 13C NMR data than the expected number. It is proposed that this may be due to isomerization during the scanning process which took place overnight, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.
MS (APCI): m/z 326.0 [M+1]$^+$

(Z)-4,5-Difluoro-3-(4-trifluoromethyl-benzylidene)-1,3-dihydro-indol-2-one (6-7)

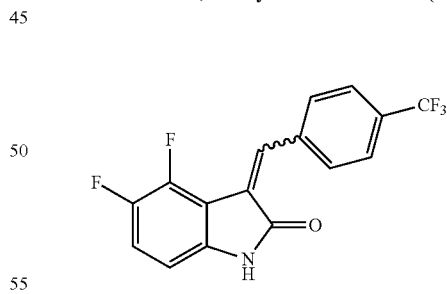

Yield 49.2%; $^1$H NMR (300 MHZ DMSO-d$_6$) δ 10.90 (s, 1H), 8.32 (d, J=7.93 Hz, 2H), 7.92-7.73 (m, 3H), 6.78-6.52 (m, 1H), 7.38-7.23 (m, 1H); $^{13}$NMR (75 MHz, DMSO-d$_6$) δ 168.0, 166.0, 147.4, 147.0, 146.8, 144.3, 143.8, 143.7, 140.4, 140.4, 139.9, 139.7, 139.3, 138.4, 138.3, 137.2, 136.7, 132.1, 130.5, 130.4, 130.1, 129.7, 129.5, 129.1, 127.1, 126.4, 126.0, 125.9, 124.8, 124.8, 124.6, 124.6, 122.3, 118.8, 118.6, 118.0, 117.8, 112.5, 112.3, 109.7, 109.5, 105.8, 105.5, 105.5; MS (APCI): m/z 326.1 [M+H]$^+$.

* More C atoms were detected in the $^{13}$C NMR data than the expected number. It is proposed that this may be due to isomerization during the scanning process, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.

(Z)-4,5-Difluoro-3-(3-trifluoromethoxyl-benzylidene)-1,3-dihydro-indol-2-one

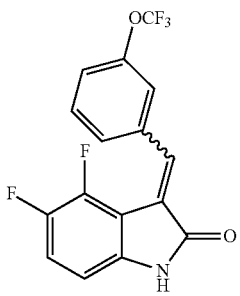 [SMILES: O=C1Nc2ccc(F)c(F)c2C1=Cc1cccc(OC(F)(F)F)c1]

Yield 46.9%; $^1$HNMR (300 MHz DMSO-d6) δ 10.9 (s, 1H), 8.57 (s, 1H), 8.55 (d, J=7.5 Hz, 1H), 8.06 (d, J=7.5 Hz, 1H), 7.57 (t, J=7.8 Hz, J=8.1 Hz, 1H), 7.46 (d, J=7.8 Hz, 1H), 7.29-7.22 (m, 1H), 6.63-6.60 (m, 1H);
$^{13}$CNMR (75 MHz, DMSO-d6) δ 167.8, 166.0, 147.9, 147.7, 147.4, 146.8, 144.1, 143.8, 143.7, 143.5, 140.3, 140.2, 139.9, 139.7, 138.1, 138.0, 137.2, 136.4, 135.3, 131.2, 129.9, 129.7, 128.8, 128.8, 126.4, 125.8, 123.4, 122.9, 122.0, 122.0, 121.8, 118.5, 118.3, 118.3, 117.6, 117.4, 112.5, 112.3, 109.4, 105.6, 105.2;

* More C atoms were detected in the 13C NMR data than the expected number. It is proposed that this may be due to isomerization during the scanning process which took place overnight, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.
MS (APCI): m/z 342.5 [M+1]$^+$.

(E/Z)-4,5-Difluoro-3-(3-methanesulfonylbenzylidene)-1,3-dihydro-indol-2-one (6-9)

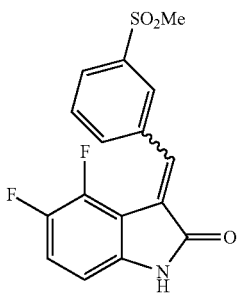 [SMILES: CS(=O)(=O)c1cccc(C=C2C(=O)Nc3ccc(F)c(F)c32)c1]

Yield 63.2%; $^1$H NMR (300 MHz DMSO-d6) δ10.92 (d, J=14.6 Hz, 1H), 8.78 (s, 1H), 8.47 (d, J=7.8 Hz, 1H), 7.98 (d, J=8.4 Hz, 1H), 7.93-7.80 (m, 1H), 7.72 (t, J=7.8 Hz, 1H), 7.42-7.22 (m, 1H), 6.76-6.56 (m, 1H), 3.25 (d, J=3.7 Hz, 3H); $^{13}$NMR (75 MHz, DMSO-d6) δ 167.8, 165.9, 147.2, 146.8, 146.7, 144.1, 143.7, 143.5, 140.6, 140.3, 139.6, 139.5, 138.2, 138.2, 136.3, 136.2, 134.6, 134.6, 134.2, 129.8, 129.1, 128.9, 128.3, 127.5, 126.6, 117.8, 117.6, 112.4, 112.2, 109.6, 109.4, 105.3, 43.4, 43.3; MS (APCI): m/z 336.4 [M+H]$^+$; Anal. Calcd. for $C_{16}H_{11}F_2NO_3S$: C, 57.31; H, 3.31. Found C, 57.32; H, 3.37.

* More C atoms were detected in the $^{13}$C NMR data than the expected number. The presence of F atoms in the compound may have caused splitting of the peaks and contributed to the additional number of peaks in the spectrum.

(Z)-3-(4,5-Difluoro-2-oxo-1,2-dihydro-indol-3-ylidenemethyl)-N-methyl-benzenesulphonamide (6-10)

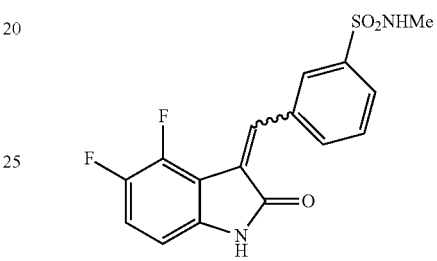

Yield 44.7%; $^1$H NMR (400 MHz, DMSO-d6) δ 10.89 (s, 1H), 8.62 (s, 1H), 8.35 (d, J=7.7 Hz, 1H), 7.86 (dd, J=22.8 Hz, 2H), 7.68 (t, J=7.8 Hz, 1H), 7.49 (s, 1H), 7.38-7.18 (m, 1H), 6.64 (dd, J=8.5 Hz, 1H), 2.45 (d, J=20.7 Hz, 3H); $^{13}$C NMR (101 MHz, DMSO-d6) δ 168.0, 166.0, 147.1, 146.9, 146.5, 146.4, 144.6, 144.4, 144.2, 144.1, 140.4, 140.3, 140.1, 140.0, 139.3, 139.0, 138.3, 138.2, 136.8, 136.1, 135.3, 134.1, 133.5, 133.5, 129.5, 129.1, 128.9, 128.2, 127.5, 127.5, 127.4, 126.5, 126.1, 118.7, 118.5, 117.8, 117.6, 112.5, 112.4, 109.6, 109.5, 105.8, 105.7, 105.5, 105.4, 28.7, 28.5; MS (ACPI): m/z 351.2 [M+H]$^+$;

(E)-3-Benzylidene-5,6-difluoro-1,3-dihydro-indol-2-one (7-1)

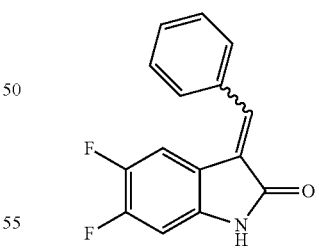

Yield 52.9%, $^1$H NMR (300 MHZ DMSO-d$_6$) δ 10.75 (s, 1H), 7.66 (d, J=4.42 Hz, 3H), 7.60-7.41 (m, 3H), 7.37-7.28 (m, 1H), 6.94-6.83 (m, 1H); $^{13}$NMR (75 MHz, DMSO-d$_6$) δ 168.6, 167.0, 152.1, 151.9, 148.8, 148.6, 146.1, 145.9, 142.9, 142.7, 140.0, 139.9, 138.4, 137.3, 137.0, 133.8, 133.6, 132.0, 130.7, 130.1, 129.2, 128.9, 128.2, 126.4, 125.4, 121.2, 121.1, 121.1, 116.8, 116.7, 116.7, 111.4, 111.1, 109.5, 109.2, 99.9, 99.6, 99.2, 98.9; MS (APCI): m/z 258.2 [M+H]$^+$.

* More C atoms were detected in the $^{13}$C NMR data than the expected number. It is proposed that this may be due to isomerization during the scanning process, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.

(E)-5,6-Difluoro-3-(2-fluoro-benzylidene)-1,3-dihydro-indol-2-one (7-2)

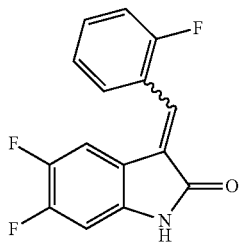 [SMILES: O=C1Nc2cc(F)c(F)cc2C1=Cc1ccccc1F]

Yield 50.2%, $^1$H NMR (300 MHZ DMSO-d$_6$) 10.90 (br, 1H), 7.75 (t, J=6.9 Hz, 1H), 7.59 (s, 2H), 7.43-7.38 (m, 2H), 7.10 (t, J=8.7 Hz, 1H), 6.92 (t, J=6.9 Hz, 1H); $^{13}$NMR (75 MHz, DMSO-d$_6$) δ168.1, 166.5, 161.2, 157.9, 152.4, 152.2, 149.1, 148.9, 146.3, 146.1, 143.1, 142.9, 140.2, 140.1, 137.9, 137.8, 132.4, 132.3, 132.0, 130.4, 128.6, 128.4, 127.6, 124.9, 124.9, 123.7, 123.7, 121.7, 121.5, 121.4, 121.2, 116.5, 116.5, 116.4, 116.4, 116.3, 116.0, 115.3, 115.0, 111.7, 111.5, 110.2, 109.9, 100.0, 99.7, 99.3, 99.0; MS (APCI): m/z 276.0 [M+H]$^+$.

* More C atoms were detected in the $^{13}$C NMR data than the expected number. It is proposed that this may be due to isomerization during the scanning process, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.

(E)-5,6-Difluoro-3-(3-fluorobenzylidene)-1,3-dihydro-indol-2-one (7-3)

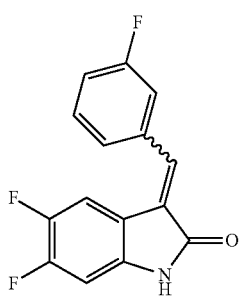 [SMILES: O=C1Nc2cc(F)c(F)cc2C1=Cc1cccc(F)c1]

Yield 21.8%; $^1$H NMR (300 MHZ DMSO-d$_6$) δ 10.78 (s, 1H), 7.77-7.41 (m, 4H), 7.42-7.16 (m, 1H), 7.07-6.72 (m, 1H); $^{13}$NMR (75 MHz, DMSO-d$_6$) δ 168.4, 166.9, 163.8, 163.3, 160.6, 160.1, 152.3, 152.1, 149.0, 145.9, 143.0, 142.8, 140.3, 140.1, 137.5, 137.4, 136.6, 136.3, 136.2, 135.8, 135.7, 135.3, 131.1, 131.0, 130.2, 130.1, 128.7, 127.3, 126.6, 125.1, 120.8, 120.8, 120.7, 117.7, 117.6, 117.4, 116.9, 116.6, 116.5, 116.4, 116.4, 116.3, 116.1, 115.8, 111.6, 111.3, 109.7, 109.4, 100.0, 99.7, 99.3, 99.0; MS (APCI): m/z 276.0 [M+H]$^+$.

* More C atoms were detected in the $^{13}$C NMR data than the expected number. It is proposed that this may be due to isomerization during the scanning process, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.

(E)-5,6-Difluoro-3-(4-fluoro-benzylidene)-1,3-dihydro-indol-2-one (7-4)

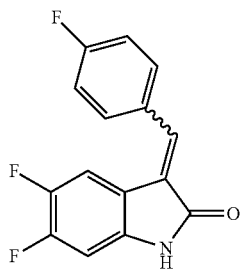 [SMILES: O=C1Nc2cc(F)c(F)cc2C1=Cc1ccc(F)cc1]

Yield 23.3%; $^1$H NMR (300 MHZ DMSO-d$_6$) δ 10.76 (s, 1H), 7.80-7.69 (m, 2H), 7.64 (s, 1H), 7.38 (d, J=6.8 Hz, 3H), 6.99-6.78 (m, 1H); $^{13}$NMR (75 MHz, DMSO-d$_6$) δ144.0, 142.7, 140.6, 137.9, 130.6, 130.5, 128.0, 127.8, 125.8, 125.6, 123.2, 123.1, 120.9, 120.7, 118.4, 117.6, 116.6, 116.5, 114.2, 114.1, 113.0, 113.0, 112.9, 109.7, 102.0, 101.9, 101.9, 101.8, 101.6, 101.3, 101.0, 100.7, 97.7, 97.5, 88.4, 88.2; MS (APCI): m/z 276.0 [M+H]$^+$.

* More C atoms were detected in the $^{13}$C NMR data than the expected number. It is proposed that this may be due to isomerization during the scanning process, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.

(E)-5,6-Difluoro-3-(2-trifluoromethyl-benzylidene)-1,3-dihydro-indol-2-one (7-5)

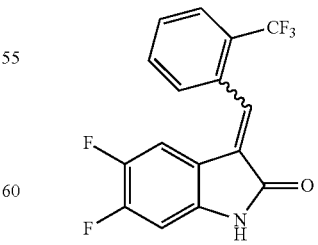

Yield 55.4%; $^1$H NMR (300 MHZ DMSO-d$_6$) δ 10.87 (d, J=1.0 Hz, 1H), 7.92 (d, J=7.1 Hz, 1H), 7.86-7.59 (m, 4H), 7.07-6.76 (m, 1H), 6.62 (t, J=8.9 Hz, 1H); $^{13}$NMR (75 MHz, DMSO-d$_6$) 167.8, 152.5, 152.3, 149.2, 149.0, 146.2, 143.0, 142.9, 140.4, 140.2, 133.1, 132.4, 132.1, 130.1, 130.0, 129.1, 127.2, 126.8, 126.6, 126.6, 126.5, 125.7, 122.0, 116.3, 116.2, 116.2, 116.1, 111.6, 111.3, 100.3, 100.0; MS (APCI): m/z 326.0 [M+H]+.

\* More C atoms were detected in the $^{13}$C NMR data than the expected number. It is proposed that this may be due to isomerization during the scanning process, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.

(E)-5,6-Difluoro-3-(3-trifluoromethyl-benzylidene)-1,3-dihydro-indol-2-one (7-6)

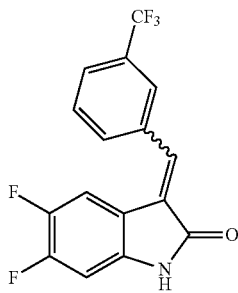 [SMILES: O=C1Nc2cc(F)c(F)cc2C1=Cc1cccc(C(F)(F)F)c1]

Yield 54.1%, $^1$HNMR (300 MHZ DMSO-d$_6$) δ 10.8 (s, 1H); 8.02 (d, J=9.3 Hz, 2H), 7.80 (d, J=7.2 Hz), 7.78 (d, J=7.2 Hz, 1H), 7.73 (s, 1H), 7.22 (t, J=9.0 Hz, 1H), 6.93 (q, J=7.2 Hz, 1H);

$^{13}$CNMR (75 MHz, DMSO-d$_6$) δ168.2, 140.4, 140.2, 134.9, 132.8, 130.1, 129.8, 129.4, 127.7, 126.3, 126.2, 125.9, 125.7, 116.4, 116.3, 116.3, 111.4, 111.1, 100.1, 99.8;

\* More C atoms were detected in the 13C NMR data than the expected number. It is proposed that this may be due to isomerization during the scanning process which took place overnight, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum. MS (APCI): m/z, 326.1 [M+1]+.

(E)-5,6-Difluoro-3-(4-(trifluoromethyl)benzylidene)-1,3-dihydro-indol-2-one (7-7)

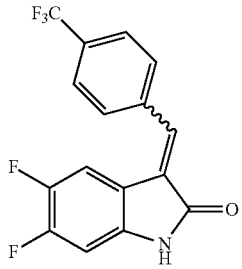 [SMILES: O=C1Nc2cc(F)c(F)cc2C1=Cc1ccc(C(F)(F)F)cc1]

Yield 66.4%, $^1$H NMR (300 MHZ DMSO-d$_6$), δ 10.81 (s, 1H), 7.85 (s, 4H), 7.66 (s, 1H), 7.39-7.14 (m, 1H), 7.02-6.73 (m, 1H); $^{13}$NMR (75 MHz, DMSO-d$_6$) δ, 168.3, 166.7, 152.5, 152.3, 149.2, 149.0, 146.2, 146.0, 143.0, 142.8, 140.4, 140.3, 138.0, 137.9, 137.7, 137.3, 135.9, 134.8, 132.1, 129.9, 129.5, 129.5, 128.0, 127.7, 125.8, 125.8, 124.9, 124.9, 122.2, 122.2, 120.6, 120.5, 120.5, 116.3, 116.2, 116.2, 111.8, 111.5, 110.0, 109.7, 100.1, 99.8, 99.4, 99.105; MS (APCI): m/z 326.0 [M+H]+.

\* More C atoms were detected in the $^{13}$C NMR data than the expected number. It is proposed that this may be due to isomerization during the scanning process, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.

(E)-5,6-Difluoro-3-(3-trifluoromethoxyl-benzylidene)-1,3-dihydro-indol-2-one (7-8)

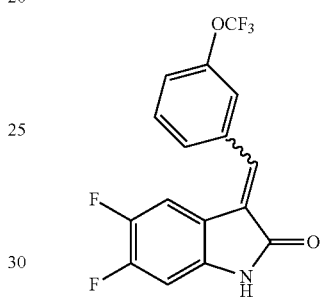

Yield 11.7%; $^1$HNMR (300 MHz DMSO-d6) δ 10.8 (s, 1H), 7.71-7.66 (m, 4H), 7.50 (d, J=7.5 Hz, 1H), 7.22 (q, J=11.4 Hz, J=10.5 Hz, 1H), 6.90 (q, J=10.5 Hz, 1H); $^{13}$CNMR (75 MHz, DMSO-d6) δ 168.2, 152.3, 152.1, 149.0, 148.8, 148.5, 146.0, 145.9, 142.9, 142.7, 140.3, 140.2, 136.1, 134.8, 131.1, 128.2, 127.7, 122.3, 121.7, 121.4, 118.3, 116.4, 116.3, 116.3, 116.2, 111.5, 111.2, 100.0, 99.7;

More C atoms were detected in the 13C NMR data than the expected number. It is proposed that this may be due to isomerization during the scanning process which took place overnight, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum. MS (APCI): m/z 342.2 [M+1]+.

(E)-5,6-Difluoro-3-(3-methanesulfonylbenzylidene)-1,3-dihydro-indol-2-one (7-9)

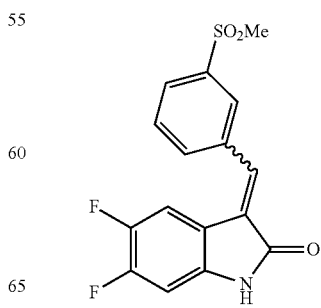

Yield 21.5%; ¹H NMR (300 MHz DMSO-d6) δ ppm, δ 10.83 (s, 1H), 8.24 (s, 1H), 7.90-7.77 (m, 1H), 7.73 (s, 1H), 7.34-7.25 (m, 1H), 6.93 (q, J=7.5 Hz, 1H), 3.29 (s, 3H) ¹³NMR (75 MHz, DMSO-d6) δ 168.2, 166.8, 152.4, 152.2, 149.1, 148.9, 146.1, 145.9, 143.9, 142.9, 142.8, 141.4, 140.8, 140.4, 140.3, 137.8, 137.6, 136.0, 135.8, 135.1, 135.0, 134.7, 134.5, 134.0, 130.1, 129.8, 129.3, 128.3, 127.9, 127.8, 127.3, 120.5, 120.5, 116.3, 116.2, 116.2, 116.1, 111.7, 111.4, 109.9, 109.6, 100.1, 99.8, 99.4, 99.1, 43.5, 43.2; MS (APCI): m/z 336.5 [M+H]⁺.

* More C atoms were detected in the ¹³C NMR data than the expected number. It is proposed that this may be due to isomerization during the scanning process which took place overnight, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.

(E)-3-(5,6-Difluoro-2-oxo-1,2-dihydro-indol-3-ylidenemethyl)-N-ethyl-benzenesulfonamide (7-10)

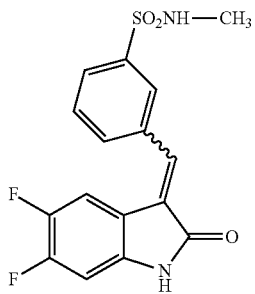

Yield 18.2%, ¹H NMR (400 MHz, DMSO-d₆), δ 8.06 (s, 1H), 10.84 (s, 1H), 7.98-7.86 (m, 3H), 7.85-7.67 (m, 2H), 7.26 (dd, J=10.82, 8.03 Hz, 1H), 6.93 (dd, J=10.47, 6.93 Hz, 1H), 2.47 (d, J=5.56 Hz, 2H); 13C NMR (100 MHz, DMSO-d6)*, δ 168.2, 166.8, 139.9, 139.5, 136.2, 135.0, 135.0, 135.0, 134.8, 134.3, 133.1, 130.1, 129.7, 129.2, 128.0, 127.7, 127.7, 127.1, 126.7, 109.9, 100.1, 99.8, 99.3, 99.1, 28.5. MS (ESI): m/z 349.3 [M−H]⁻.

* More C atoms were detected in the ¹³C NMR data than the expected number. It is proposed that this may be due to isomerization during the scanning process which took place overnight, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.

(E) 3-(3-Trifluoromethyl-benzylidene)-1,3-dihydro-indol-2-one (8-1)

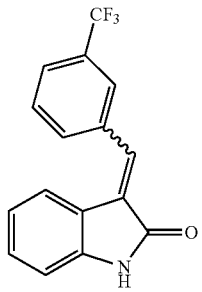 [SMILES: O=C1Nc2ccccc2C1=Cc1cccc(C(F)(F)F)c1]

Yield 45.5%; ¹HNMR (300 MHz DMSO-d6) δ 10.67 (s, 1H), 8.02 (d, J=8.4 Hz, 2H), 7.83 (d, J=7.8 Hz, 1H), 7.76 (t, J=7.5 Hz, 1H), 7.68 (s, 1H), 7.33 (d, J=7.5 Hz, 1H), 7.25 (t, J=7.2 Hz, J=7.8 Hz, 1H), 6.90-6.81 (m, 1H); 13CNMR (75 MHz, DMSO-d6) δ 168.2, 143.2, 135.6, 133.7, 132.9, 130.6, 129.9, 129.7, 129.3, 129.1, 125.8, 125.7, 122.1, 121.1, 120.4, 110.3;

MS (APCI): m/z 290.4 [M+1]⁺.

(E/Z) 3-(3-Trifluoromethyl-phenylimino)-1,3-dihydro-indol-2-one (8-2)

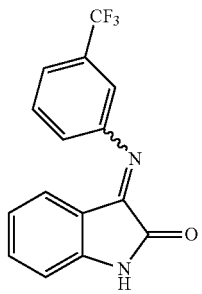 [SMILES: O=C1Nc2ccccc2C1=Nc1cccc(C(F)(F)F)c1]

Yield 82.3%; ¹H NMR (300 MHz DMSO-d6) δ 11.02 (d, J=39.0 Hz, 2H), 7.34-7.70 (m, 10H), 6.90 (t, J=8.4 Hz, 2H), 6.74 (t, J=7.8, 2H), 6.26 (d, J=7.8, 2H); ¹³NMR (75 MHz, DMSO-d6) δ 163.2, 158.5, 155.9, 154.1, 151.1, 149.9, 147.2, 146.1, 134.8, 134.6, 130.9, 130.6, 130.1, 129.4, 129.4, 125.7, 125.1, 123.1, 122.9, 122.3, 122.1, 121.8, 121.6, 121.3, 121.3, 121.0, 115.5, 115.5, 114.2, 114.2, 111.7, 110.9; MS (APCI): m/z 291.3 [M+H]⁺.

* More C atoms were detected in the ¹³C NMR data than the expected number. The presence of F atoms in the compound may have caused splitting of the peaks and contributed to the additional number of peaks in the spectrum.

(E)-1-Methyl-3-(3-trifluoromethyl-benzylidene)-1,3-dihydro-indol-2-one (8-3)

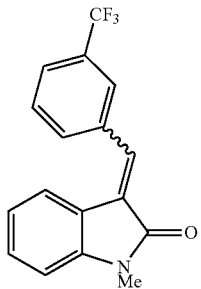 [SMILES: CN1C(=O)C(=Cc2cccc(C(F)(F)F)c2)c2ccccc21]

Yield 25.1%; ¹HNMR (300 MHz DMSO-d6) δ 8.01 (d, J=8.1 Hz, 2H), 7.85-7.76 (m, 3H), 7.34 (t, J=7.5 Hz, J=8.1 Hz, 2H), 7.07 (d, J=7.8 Hz, 1H), 6.90 (t, J=7.8 Hz, 1H), 3.21 (s, 3H);

¹³CNMR (75 MHz, DMSO-d6) δ 166.9, 144.3, 135.5, 134.3, 133.0, 130.6, 129.9, 129.7, 129.3, 128.1, 126.0, 126.0, 125.8, 125.8, 121.8, 121.7, 119.8, 109.1, 26.0;

More C atoms were detected in the 13C NMR data than the expected number. It is proposed that this may be due to isomerization during the scanning process which took place overnight, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum.

MS (APCI): m/z 304.2 [M+1]⁺.

(E/Z) 6-Chloro-3-(3-trifluoromethyl-phenylimino)-1,3-dihydro-indol-2-one (8-4)

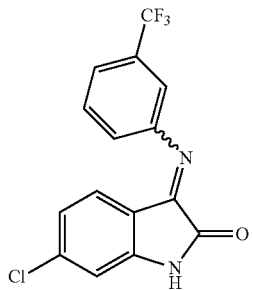 [SMILES: O=C1Nc2cc(Cl)ccc2C1=Nc1cccc(C(F)(F)F)c1]

Yield 34.2%; ¹H NMR (300 MHz DMSO-d6) δ 11.16 (br, 2H), 7.78-7.24 (m, 9H), 7.17-7.04 (m, 1H), 6.92 (dd, J=6.9, 1.4 Hz, 2H), 6.83 (dd, J=8.2, 1.6 Hz, 1H), 6.25 (d, J=8.3 Hz, 1H); ¹³NMR (75 MHz, DMSO-d6) δ182.9, 163.2, 159.3, 158.4, 154.8, 153.1, 151.7, 150.7, 149.6, 148.6, 147.2, 142.2, 138.8, 138.7, 131.0, 130.9, 130.6, 130.2, 129.8, 129.4, 129.4, 128.9, 126.4, 126.1, 125.7, 124.5, 123.0, 122.6, 122.3, 122.2, 122.1, 121.7, 121.6, 120.8, 120.7, 119.9, 118.4, 116.7, 115.6, 115.5, 114.4, 114.3, 114.2, 112.1, 111.6, 110.9; MS (APCI): m/z 325.2 [M+H]⁺.

* More C atoms were detected in the ¹³C NMR data than the expected number. The presence of F atoms in the compound may have caused splitting of the peaks and contributed to the additional number of peaks in the spectrum.

(E)-6-Chloro-1-methyl-3-(3-trifluoromethyl-benzylidene)-1,3-dihydro-indol-2-one (8-5)

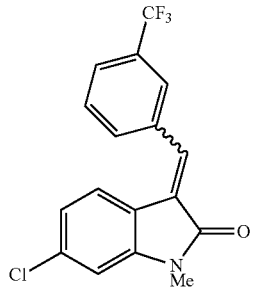 [SMILES: CN1C(=O)C(=Cc2cccc(C(F)(F)F)c2)c2ccc(Cl)cc21]

Yield 16.6%; ¹HNMR (300 MHz DMSO-d6), δ7.97 (d, J=7.6 Hz, 2H), 7.88-7.68 (m, 3H), 7.30 (d, J=8.2 Hz, 1H), 7.17 (s, 1H), 6.93 (d, J=8.1 Hz, 1H), 3.19 (s, 3H); ¹³CNMR (75 MHz, DMSO-d6), δ 167.0, 145.7, 143.4, 135.2, 135.1, 134.9, 134.4, 133.9, 132.9, 130.0, 129.3, 127.1, 126.3, 125.9, 125.9, 123.0, 122.3, 121.5, 121.4, 121.2, 118.6, 109.5, 26.2, 26.0.

More C atoms were detected in It is proposed that this may be due to isomerization during the scanning process which took place overnight, resulting in a mixture of isomers. The isomerization could be identified by comparing the proton spectrum which is done before carbon spectrum and the one which is done after the carbon spectrum. The presence of F atoms in the compound may have caused splitting of the peaks and contributed to the additional number of peaks in the spectrum. MS (APCI): m/z 338.4 [M+1]⁺.

(E/Z) 5-Chloro-3-(3-trifluoromethyl-phenylimino)-1,3-dihydro-indol-2-one (8-6)

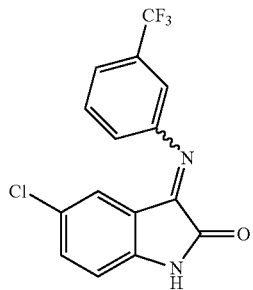 [SMILES: O=C1Nc2ccc(Cl)cc2C1=Nc1cccc(C(F)(F)F)c1]

Yield, 84.8%; ¹H NMR (300 MHz DMSO-d6) δ11.09 (d, J=43.1 Hz, 2H), 7.81-7.19 (m, 9H), 7.10-6.78 (m, 2H), 6.13 (d, J=2.0 Hz, 1H); ¹³NMR (75 MHz, DMSO-d6) δ 162.9, 158.3, 155.1, 153.4, 150.6, 149.4, 146.0, 144.7, 134.0, 133.9, 131.0, 130.6, 130.2, 129.5, 129.3, 128.9, 126.4, 125.6, 125.3, 124.5, 123.0, 122.6, 122.6, 122.0, 121.7, 120.9, 120.9, 116.7, 115.6, 115.5, 114.3, 114.2, 113.3, 112.5; MS (APCI): m/z 325.3 [M+H]⁺.

* More C atoms were detected in the ¹³C NMR data than the expected number. The presence of F atoms in the compound may have caused splitting of the peaks and contributed to the additional number of peaks in the spectrum.

(E/Z)-5-Fluoro-3-(3-trifluoromethyl-phenylimino)-1,3-dihydro-indol-2-one (8-7)

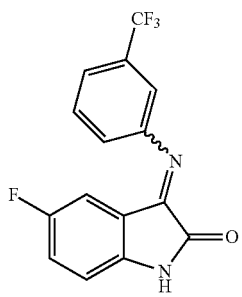 [SMILES: O=C1Nc2ccc(F)cc2C1=Nc1cccc(C(F)(F)F)c1]

Yield, 52.5%; $^1$H NMR (300 MHz DMSO-d6) δ10.98 (d, J=38.2 Hz, 2H), 7.73 (t, J=7.8 Hz, 1H), 7.64 (d, J=7.7 Hz, 1H), 7.54 (t, J=7.7 Hz, 1H), 7.47-7.24 (m, 8H), 6.95-6.90 (m, 2H), 5.89 (dd, J=8.3, 2.2 Hz, 1H); $^{13}$NMR (75 MHz, DMSO-d6) δ 163.2, 159.7, 159.4, 158.6, 158.3, 156.5, 155.5, 155.1, 153.9, 150.5, 149.4, 146.9, 143.6, 142.3, 131.1, 131.0, 130.6, 130.2, 129.8, 129.5, 129.4, 129.0, 125.9, 125.6, 124.6, 124.3, 122.9, 122.3, 122.2, 122.1, 121.6, 121.4, 121.1, 121.0, 120.9, 120.8, 120.7, 118.5, 118.4, 118.4, 115.9, 115.8, 115.5, 115.5, 114.3, 114.2, 113.5, 113.4, 112.9, 112.8, 112.1, 112.0, 111.8, 111.5, 111.1, 110.1, 109.8; MS (APCI): m/z [M+H]$^+$.

* More C atoms were detected in the $^{13}$C NMR data than the expected number. The presence of F atoms in the compound may have caused splitting of the peaks and contributed to the additional number of peaks in the spectrum.

Example 2

Determination of Antiproliferative Activity

MTT was purchased from DUCHEFA Biochemie (Denmark). Sunitinib, and sodium dodecyl sulfate, bovine serum albuminwere obtained from Sigma Aldrich (Singapore). Sorafenib was purchase from Ontario Chem. Fetal bovine serum (FBS) was obtained from Invitrogen. Human hepatocellular carcinoma cells (HuH-7 and Hep G2), and human diploid fibroblast strain (IMR 90). HuH7 was obtained as gifts from Dr Ho Han Kiat, Department of Pharmacy, NUS. IMR90 and Hep G2 were purchased from American Type Culture Collection (ATCC). HuH-7 cells were cultured in DMEM (Dulbecco's Modified Eagle Medium, high glucose) with 10% v/v fetal bovine serum (FBS), 100 mg/L penicillin G and 100 mg/L streptomycin. IMR 90 cell were cultured in EMEM (Eagle's Minimum Essential Medium), with 10% v/v FBS and 100 mg/L penicillin G and 100 mg/L streptomycin. The cells were sub-cultured when HuH7 or Hep G2 reached a density of 70-80×10$^5$ cell/T75 flask, and IMR 90 reached 20×10$^5$ cell/T75 flask. Cells were used within 2-10 passages for viability experiments.

The anti-proliferative activity of the test compounds were determined by the MTT assay. An aliquot (200 μL, 3×10$^4$ cells/mL for HuH7, 3.75×10$^4$ cells/mL for Hep G2, and 2×10$^4$ cells/mL for IMR 90) of medium was added to each well of the microtitre plate. After 24 h incubation at 37 deg C., 5% CO$_2$, the cells were observed to have attached onto the floor of the well. The existing medium was removed from each well and replaced by fresh medium (200 μL) containing a known concentration of test compound. The final concentration of DMSO in each well was maintained at 0.5% v/v. (1% v/v was also utilized if the compounds were not soluble) The test compounds were incubated with the cells for another 72 h at 37 deg C., 5% CO$_2$. The medium was then removed from the well and replaced with FBS free medium (200 μL) and MTT (50 μL of 2 mg/mL solution in phosphate buffer saline, pH 7.4). The phosphate buffer saline comprises 10 mM of potassium phosphate and 137 mM sodium chloride. After incubation (3 h) at 37 deg C., 5% CO$_2$, the supernatant was removed and a solution of 200 μL DMSO and 25 μL Sorenson buffer (0.1 M glycine, 0.1 M sodium chloride, adjusted to pH 10.5 with 0.1 M sodium hydroxide) was added to dissolve the formazan crystals in each well. Vehicle control were cells grown in 1% v/v DMSO/Medium for 72 h, 37 deg C., 5% CO$_2$ while blank controls were wells that contained only 200 μL DMSO and 25 μL Sorenson buffer. Absorbances were measured at 570 nm on a microplate reader (Tecan, Infinite 200). The viability of cells at a given concentration of test compound was determined from the expression:

$$\text{Percentage Cell Viability} = \frac{\langle \text{abs\_compound} \rangle - \langle \text{abs\_blank} \rangle}{\langle \text{abs\_vehcontrol} \rangle - \langle \text{abs\_blank} \rangle} \times 100\%$$

where abs_compound=absorbance of wells containing cells and test compound, abs_vehicle (Not the same as above. Change to abs_vehicle)=absorbance of vehicle control and abs_blank=absorbance of blank control.

Each concentration of test compound was evaluated at least 3 times on separate occasions, and two different stock solution were used. The IC$_{50}$ value (concentration that inhibited 50% of cell growth) was determined from the sigmoidal curve obtained by plotting percentage viability versus logarithmic concentration of test compound using GraphPad Prism 5 (San Diego, USA).

Results

The results of the growth inhibition assays on HuH7 cells are presented in Tables 1-8 below.

Tables 1-8: IC$_{50}$ of Targeted Compounds on HuH7 cells (94 Compounds).

IC$_{50}$=mean and SD of 3 or more independent determinations. N.B. Compound 1-10 is a known compound used for comparison. Compounds 2-7, 3-6, 4-10 and 5-6 are also comparative compounds.

TABLE 1

Series 1

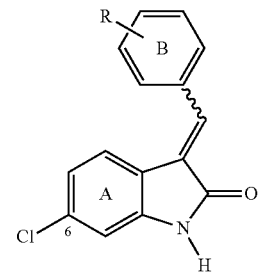

| No | R | IC 50 (μM) |
|---|---|---|
| 1-1 | H | 17.54 ± 3.54 |
| 1-2 | 2'F | N.A.$^a$ |
| 1-3 | 3'F | 10.03 ± 0.87 |
| 1-4 | 4'F | 12.87 ± 0.95 |

TABLE 1-continued

Series 1

[Structure: indolin-2-one with 6-Cl on ring A, benzylidene at C3 with R on ring B]

| No | R | IC 50 (μM) |
|---|---|---|
| 1-5 | 3'Me | 11.01 ± 0.28 |
| 1-6 | 2'OMe | >30 |
| 1-7 | 3'OMe | 12.21 ± 0.64 |
| 1-8 | 4'OMe | >30 |
| 1-9 | 2'CF$_3$ | 24.11 ± 5.29 |
| 1-10 | 3'CF$_3$ | 0.46 ± 0.06 |
| 1-21 | 4'SO$_2$NHMe | 15.29 ± 0.60 |
| 1-22 | 3'SO$_2$NHEt | 0.84 ± 0.09 |
| 1-11 | 4'CF$_3$ | 10.97 ± 1.78 |
| 1-12 | 3'4'F | 16.69 ± 3.40 |
| 1-13 | 2'OCF$_3$ | N.A.$^a$ |
| 1-14 | 3'OCF$_3$ | 5.06 ± 0.74 |
| 1-15 | 4'OCF$_3$ | 10.09 ± 1.73 |
| 1-17 | 3'SO$_2$NH$_2$ | 3.41 ± 0.38 |
| 1-16 | 3'SO$_2$Me | 10.78 ± 3.72 |
| 1-18 | 3'SO$_2$NHMe | 0.54 ± 0.06 |
| 1-19 | 3'CN | 7.36 ± 0.30 |
| 1-20 | 3'SO$_2$N(Me)$_2$ | 4.87 ± 0.36 |
| 1-23 | 3'SO$_2$NHPr | 0.36 ± 0.04 |
| 1-24 | 3'SO$_2$NHiPr | 1.93 ± 0.34 |

TABLE 2

Series 2

[Structure: indolin-2-one with 5-Cl on ring A, benzylidene at C3 with R on ring B]

| No | R | IC 50 (μM) |
|---|---|---|
| 2-1 | H | 21.26 ± 2.22 |
| 2-2 | 2'F | >30 |
| 2-3 | 3'F | 15.11 ± 2.91 |
| 2-4 | 4'F | 12.74 ± 2.82 |
| 2-5 | 3'OMe | >30 |
| 2-6 | 2'CF$_3$ | >30 |
| 2-7 | 3'CF$_3$ | 0.81 ± 0.11 |
| 2-8 | 4'CF$_3$ | 7.92 ± 1.45 |
| 2-9 | 3'4'F | 11.43 ± 1.45 |
| 2-10 | 3'OCF$_3$ | 3.83 ± 0.25 |
| 2-11 | 3'SO2Me | 6.53 ± 0.51 |
| 2-12 | 3'SO$_2$NH$_2$ | 9.66 ± 1.59 |
| 2-13 | 3'CN | 10.41 ± 1.99 |
| 2-14 | 3'SO$_2$NHMe | 3.13 ± 0.07 |

TABLE 3

Series 3

[Structure: indolin-2-one with 6-F on ring A, benzylidene at C3 with R on ring B]

| No | R | IC 50 (μM) |
|---|---|---|
| 3-1 | H | N.A.$^a$ |
| 3-2 | 2'F | 0.91 ± 0.15 |
| 3-3 | 3'F | 2.41 ± 1.07 |
| 3-4 | 4'F | N.A.$^a$ |
| 3-5 | 2'CF$_3$ | >30 |
| 3-11 | 3'SO$_2$HEt | 0.39 ± 0.07 |
| 3-12 | 3'SO$_2$NHPr | 0.12 ± 0.01 |
| 3-6 | 3'CF$_3$ | 1.41 ± 0.13 |
| 3-7 | 4'CF$_3$ | 8.42 ± 0.27 |
| 3-8 | 3'OCF$_3$ | 7.48 ± 0.20 |
| 3-9 | 3'SO$_2$Me | 12.69 ± 1.54 |
| 3-10 | 3'SO$_2$NHMe | 0.48 ± 0.01 |
| 3-13 | 3'SO$_2$NHiPr | 2.29 ± 0.06 |

TABLE 4

Series 4

[Structure: indolin-2-one with 5-F on ring A, benzylidene at C3 with R on ring B]

| No | R | IC 50 (μM) |
|---|---|---|
| 4-1 | H | 21.35 ± 1.73 |
| 4-2 | 2'F | >30 |
| 4-3 | 3'F | 13.29 ± 2.31 |
| 4-4 | 4'F | 13.24 ± 0.42 |
| 4-5 | 2'Me | 11.69 ± 1.10 |
| 4-6 | 3'Me | >30 |
| 4-7 | 4'Me | 20.80 ± 4.02 |
| 4-8 | 3'OMe | 16.42 ± 4.15 |
| 4-9 | 2'CF$_3$ | >30 |
| 4-10 | 3'CF$_3$ | 4.04 ± 0.54 |
| 4-11 | 4'CF$_3$ | 9.31 ± 1.04 |
| 4-12 | 3'4'F | 15.31 ± 0.18 |
| 4-13 | 3'OCF$_3$ | 23.13 ± 4.75 |
| 4-14 | 3'SO$_2$Me | 5.19 ± 0.63 |
| 4-15 | 3'CN | 7.36 ± 1.08 |
| 4-16 | 3'SO$_2$NHMe | 1.18 ± 0.02 |

TABLE 5

Series 5#

| No | R | IC 50 (μM) |
|---|---|---|
| 5-1 | H | 0.94 ± 0.19 |
| 5-2 | 2'F | 0.49 ± 0.05 |
| 5-3 | 3'F | 0.71 ± 0.07 |
| 5-4 | 4'F | 5.36 ± 0.14 |
| 5-5 | 2'CF$_3$ | 7.04 ± 0.80 |
| 5-6 | 3'CF$_3$ | 1.20 ± 0.05 |
| 5-7 | 4'CF$_3$ | >30 |
| 5-8 | 3'SO$_2$NHMe | 0.17 ± 0.02 |

TABLE 6

Series 6

| No | R | IC 50 (μM) |
|---|---|---|
| 6-1 | H | 31.07 ± 2.12 |
| 6-2 | 2'F | 16.89 ± 1.67 |
| 6-3 | 3'F | 15.91 ± 1.14 |
| 6-4 | 4'F | 13.98 ± 0.73 |
| 6-5 | 2'CF$_3$ | >30 |
| 6-6 | 3'CF$_3$ | 0.54 ± 0.07 |
| 6-7 | 4'CF$_3$ | >30 |
| 6-8 | 3'OCF$_3$ | 2.94 ± 0.26 |
| 6-9 | 3'SO$_2$Me | 13.91 ± 2.03 |
| 6-10 | 3'SO$_2$NHMe | 15.81 ± 3.37 |

TABLE 7

Series 7

| No | R | IC 50 (μM) |
|---|---|---|
| 7-1 | H | >30 |
| 7-2 | 2'F | >30 |
| 7-3 | 3'F | 19.21 ± 3.25 |
| 7-4 | 4'F | N.A.$^a$ |
| 7-5 | 2'CF$_3$ | >30 |
| 7-6 | 3'CF$_3$ | 0.82 ± 0.20 |
| 7-7 | 4'CF$_3$ | 10.57 ± 0.68 |
| 7-8 | 3'OCF$_3$ | 5.61 ± 0.26 |
| 7-9 | 3'SO$_2$Me | 13.91 ± 2.03 |
| 7-10 | 3'SO$_2$NHMe | 2.76 ± 0.16 |

TABLE 8

Series 8

| No | R$_1$ | R$_2$ | R$_3$ | IC 50 (μM) |
|---|---|---|---|---|
| 8-1 | H | H | CH | 5.56 ± 0.06 |
| 8-2 | H | H | N | >30 |
| 8-3 | H | CH$_3$ | CH | 6.74 ± 1.23 |
| 8-4 | 6Cl | H | N | 20.07 ± 1.72 |
| 8-5 | 6Cl | CH$_3$ | CH | 1.14 ± 0.19 |
| 8-6 | 5Cl | H | N | 20.29 ± 3.53 |
| 8-7 | 5F | H | N | 23.13 ± 0.21 |

$^a$IC$_{50}$ could not be determined due to poor solubility of test compound

Table 9 lists the compounds that have IC$_{50}$≤1 μM on HuH7 cells. They were examined on another human liver carcinoma cell line HepG2 and on a non-malignant human cell line (lung fibroblast) IMR90. Compounds 1-10, 2-7, sorafenib and sunitinib are included for comparison.

TABLE 9

Growth inhibitory IC$_{50}$ values of selected compounds

| Compound | R$^{1a}$, R$^{1b}$ | R$^{3a}$ | IC$_{50}$ (μM) HuH7 | IC$_{50}$ (μM) Hep G2 | IC$_{50}$ (μM) IMR 90 |
|---|---|---|---|---|---|
| 1-10 | 6Cl, H | 3'CF3 | 0.46 ± 0.06 | 0.94 ± 0.18 | 9.23 ± 0.88 |
| 1-18 | 6Cl, H | 3'SO$_2$NHMe | 0.54 ± 0.06 | 3.99 ± 0.43 | 2.10 ± 0.35 |

TABLE 9-continued

Growth inhibitory IC$_{50}$ values of selected compounds

| Compound | R$^{1a}$, R$^{1b}$ | R$^{3a}$ | IC$_{50}$ (µM) HuH7 | IC$_{50}$ (µM) Hep G2 | IC$_{50}$ (µM) IMR 90 |
|---|---|---|---|---|---|
| 1-21 | 6Cl, H | 4'SO$_2$NHMe | 15.29 ± 0.60 | >30 | Not done |
| 1-22 | 6Cl, H | 3'SO$_2$NHEt | 0.84 ± 0.09 | 3.96 ± 0.55 | Not done |
| 1-23 | 6Cl, H | 3'SO$_2$NHPr | 0.36 ± 0.04 | 1.51 ± 0.11 | Not done |
| 1-24 | 6Cl, H | 3'SO$_2$NHiPr | 1.93 ± 0.34 | 5.46 ± 0.95 | Not done |
| 2-7 | 5Cl, H | 3'CF$_3$ | 0.81 ± 0.11 | 1.50 ± 0.06 | 9.13 ± 1.12 |
| 3-2 | 6F, H | 2'F | 0.91 ± 0.15 | 1.82 ± 0.63 | 2.06 ± 0.33 |
| 3-10 | 6F, H | 3'SO$_2$NHMe | 0.48 ± 0.01 | 4.40 ± 0.43 | 10.40 ± 0.23 |
| 3-11 | 6F, H | 3'SO$_2$NHEt | 0.39 ± 0.07 | 1.61 ± 0.16 | Not done |
| 3-12 | 6F, H | 3'SO$_2$NHPr | 0.12 ± 0.01 | 0.72 ± 0.12 | Not done |
| 3-13 | 6F, H | 3'SO$_2$NHiPr | 2.29 ± 0.06 | 4.22 ± 0.48 | Not done |
| 4-16 | 5F, H | 3'SO$_2$NHMe | 1.18 ± 0.02 | 9.11 ± 0.32 | 9.92 ± 0.57 |
| 6-6 | 4F, 5F | 3'CF$_3$ | 0.54 ± 0.07 | 0.96 ± 0.11 | 8.10 ± 0.73 |
| 7-6 | 5F, 6F | 3'CF$_3$ | 0.82 ± 0.20 | 0.69 ± 0.02 | 8.53 ± 0.60 |
| Sorafenib | — | — | 5.35 ± 0.49 | 5.60 ± 0.21 | 11.00 ± 1.72 |
| sunitinib | — | — | 5.60 ± 0.12 | 5.07 ± 0.07 | 6.32 ± 1.24 |

It can be seen that the compounds were generally more potent on HuH7 than HepG2 cells and the difference in activity is particularly evident in those compounds in which R$^{3a}$ is SO$_2$NHCH$_3$ (1-18, 3-10, 4-16). The difference in IC$_{50}$ values is less marked among compounds in which R$^{3a}$ is 3'CF$_3$ (1-10, 2-7, 6-6, 7-6).

Among the N-alkylsulphonamides, the N-propyl analogs (1-23, 3-12) are outstanding for their potent antiproliferative activities on both HuH7 and HepG2 cells. Compound 3-12 is 4× more potent than 1-10 (original lead) on HuH7 and just as potent as 1-10 on HepG2 cells.

Most of the compounds were more potent on the malignant cells as compared to the non-malignant IMR90 cells, which is a desirable finding. 1-18 is an exception: it has a lower IC$_{50}$ on IMR90 (2.1 µM, <IC$_{50}$ for HepG2, but >IC$_{50}$ for HuH7).

In terms of selective antiproliferative activity, the best results were obtained with the 3'CF$_3$ analogs 6-6, 7-6, 2-7 and 1-10.

Example 3

Determination of AFP mRNA Levels

The primers of alpha fetoprotein (AFP) and glyceraldehyde-3-phosphate dehydrogenase (GAPDH) were obtained from Sigma Aldrich (Singapore). The primer sequences were: AGC TTG GTG GTG GAT GAA AC (AFP forward); TCT TGC TTC ATC GTT TGC AG (AFP reverse); ACT TTG GTA TCG TGG AAG GAC (Human GADPH forward); GTA GAG GCA GGG ATG ATG TTC (Human GADPH reverse).

HuH7 cells were plated at a density of 200,000 cells per well in a 6-well plate and cultured for 24 h. A stock solution of test compound was prepared in DMSO and serially diluted with medium to give the desired concentration in the well. The final concentration of DMSO was 1% v/v. The cells were incubated with test compound for 24 h after which they were lysed, total RNA were extracted from the lysed cells and purified with RNeasy minikit (Qiagen, Valencia, Calif.). Five µg RNA was used for cDNA synthesis using SuperScript 111 (Invitrogen), performed according to manufacturer's instruction. Quantitative real-time-PCR was performed using BioRad CFX96 (Hercules, Calif.) for AFP with glyceraldehyde-3-phosphate dehydrogenase (GAPDH) as control. The BioRad CFX96 was used with a protocol that consists of initial denaturation step at 95 deg C. for 10 min, followed by 40 cycles at 95 deg C. for and 60 deg C. for 60 s. Samples were prepared in triplicates with 2 µL of predluted cDNA each.

Data were obtained as average of triplicate C$_T$ values, and normalized against control as ΔC$_T$. Expression changes in AFP transcripts between normal vs. tumor tissue were expressed as fold change using $2^{\Delta\Delta CT}$ (difference between the ΔC$_T$ of the matched pairs).

Results

Alpha-fetoprotein (AFP) levels are routinely used as a biomarker to monitor the response of HCC patients to drug treatment. Patients with hepatocellular carcinoma have elevated levels of AFP and a reduction in AFP levels is normally seen as a positive prognosis. For patients who are on treatment regimens, a fall in AFP levels indicates that they are responding to drug treatment. Compound 1-10 has been shown to reduce AFP mRNA levels in HuH7 cells and it is of interest to determine if the compounds of the present invention have similar effects. Therefore compounds 1-18 and 6-6 were investigated. As seen in FIG. 1, the effect of 1-10 on AFP levels was reproducible in our hands. 1-10 reduced AFP mRNA by almost half at 10 µM. Its effects were significantly greater than that of sunitinib and sorafenib (personal communication from Ho HK). When tested at 10 µM, 1-18 caused no significant change in AFP mRNA levels but 6-6 reduced levels to almost the same extent as 1-10.

Example 4

EROD Assay

7-Ethoxyresorufin and β-napthoflavone were obtained from Sigma Aldrich (Singapore)

The induction of CYP1A1 activity was monitored by the 7-ethoxyresorufin O-deethylase (EROD) assay. EROD is a CYP1A1 enzyme and induction of its activity would result in the formation of more resorufin, a fluorescent compound. By monitoring resorufin levels in cells that are exposed to test compound and comparing the levels with those in untreated cells, it is possible to identify compounds that induce EROD activity.

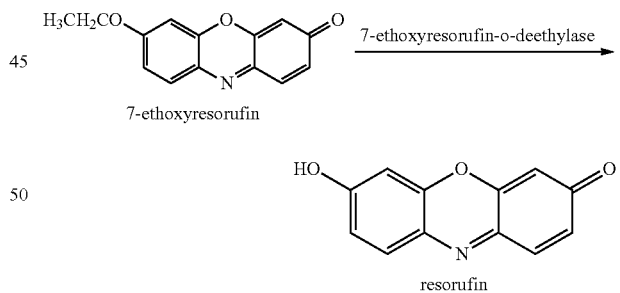

The method of Marchand was followed with modifications.[35] Briefly, HuH7 cells were plated at a density of 10$^4$ cells per well in a 96-well plate and cultured for 24 h. A stock solution of test compound was prepared in DMSO and serially diluted with medium to give the desired concentration in the well. The final concentration of DMSO was 1% v/v (0.5% v/v for 3-10). The cells were incubated with test compound for 48 h at 37 deg C., 5% CO$_2$, after which the medium was removed, the wells washed with 200 µL of 1× phosphate-buffered saline solution (PBS) and then incubated with 5 µM 7-ethoxyresorufin and 2 mM salicylamide in 200 μL of medium at 37 deg C., 40 min. Readings were taken at $\lambda_{excitation}$ of 530 nm and $\lambda_{emission}$ of 590 nm on a fluorometer (Name the plate reader). Background fluorescence of the test compound was determined at the same wavelengths to take into account its contribution to the observed readings. Readings of "blank" wells that contained only media and "control" wells with only HuH7 cells in media (with 1% DMSO) were also determined. β-napthoflavone (BNF), a known inducer of CYP1A1 activity (give ref) was used as a positive control. The extent to which EROD activity was induced is given by the expression:

Degree of induction=$(F_{Cells+Test\ Compound}-F_{Blank})/(F_{Control}-F_{Blank})$ Where $F_{cells+test\ compound}$=fluorescence of wells containing treated cells; $F_{Blank}$=fluorescence of well containing media only; $F_{Control}$=fluorescence readings of wells containing untreated cells. The test compounds were not fluorescent at the excitation and emission wavelengths used in this assay. Two separate determinations were made for each concentration of test compound.

Results

Figure 2:
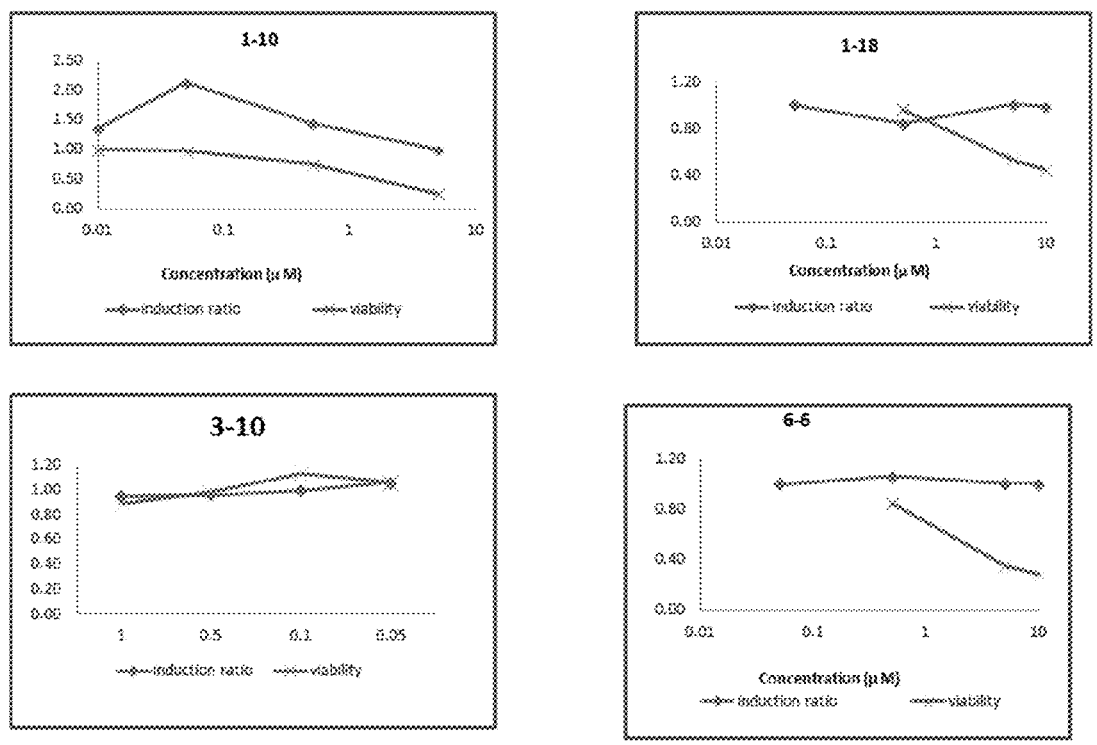
FIG. 2 is a series of plots showing the effect of target compounds on EROD activity and viability of HuH7 cells after 24 h of incubation at 37 deg C. The Y-axis represents induction ratio or viability ratio which is the fold change in induction or viability, compared to untreated cells.

Compounds 1-10, 1-18, 3-10 and 6-6 were tested for CYP1A1 induction in HuH7 cells over a concentration range that spanned their growth inhibitory concentrations. In view of the possibility that some of these concentrations could adversely affect the viability of HuH7 cells, the effect on cell viability was concurrently monitored at each concentration. The results are depicted in FIG. 2. From these results it can be seen the test compounds did not induce CYP450 activity over a broad range of concentrations. 1-10 however showed an unusual (but reproducible) induction at 0.05 μM which declined at higher concentrations.

Example 5

Detection of Phosphorylated STAT3 and STATt

Rabbit polyclonal antibodies to STAT3 was obtained from Santa Cruz Biotechnology (Santa Cruz, Calif.), and rabbit monoclonal antibodies against phospho-STAT3 (Tyr 705) were purchased from Cell Signaling Technology (Beverly, Mass.).

STAT3, a component of the JAK/STAT signaling pathway regulates several gene products involved in cell survival (eg. Bcl-xl, Bcl-2, surviving), proliferation (e.g. cyclin D1) and angiogenesis (eg. VEGF). Among the different STATs, STAT3 is constitutively activated in many human cancers including HCC. Phosphorylated STAT1, STAT3 and STAT5 are significantly elevated in HCC. In those HCC with poor prognosis, higher levels of phosphorylated STAT3 (pSTAT3) are found. In addition, the levels of JAK/STAT target proteins such as Bcl-xl, Mcl-1, cyclin D1 and c-Myc are increased in most HCCs. Therefore targeting the JAK/STAT pathway may be an attractive strategy in HCC therapy.

For detection of phopho-STAT 3 and STAT 3, treated whole-cell extracts were lysed in lysis buffer (20 mM Tris (pH 7.4), 250 mM NaCl, 2 mM EDTA (pH 8.0), 0.1% Triton X-100, 0.01 mg/ml aprotinin, 0.005 mg/ml leupeptin, 0.4 mM PMSF, and 4 mM NaVO4). Lysates were then spun at 14,000 rpm for 10 min to remove insoluble material and resolved on a 7.5% SDS gel. After electrophoresis, the proteins were electrotransferred to a nitrocellulose membrane, blocked with 5% nonfat milk, and probed with anti-phospho-STAT 3 and anti-STAT 3 antibodies (1:1,000) overnight at 4° C. The blot was washed, exposed to HRP-conjugated secondary antibodies for 1 hr, and finally examined by chemiluminescence (ECL; GE Healthcare, Little Chalfont, Buckinghamshire, UK).

Results

Figure 3:
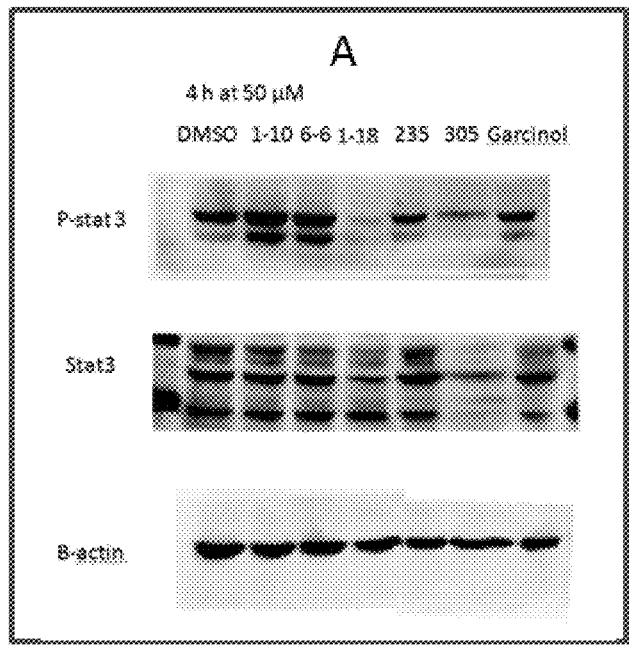
FIG. 3 is a set of gels showing:
(A) Effects of Compounds 1-10, 6-6 and 1-18 (235, 305 are other compounds that were concurrently investigated, garcinol is the positive control) on phosphorylated STAT levels; and
(B) Effect of Compound 1-18 at different concentrations and incubation times on phosphorylated STAT 3 levels in Hep G2 cells.
Figure 3:
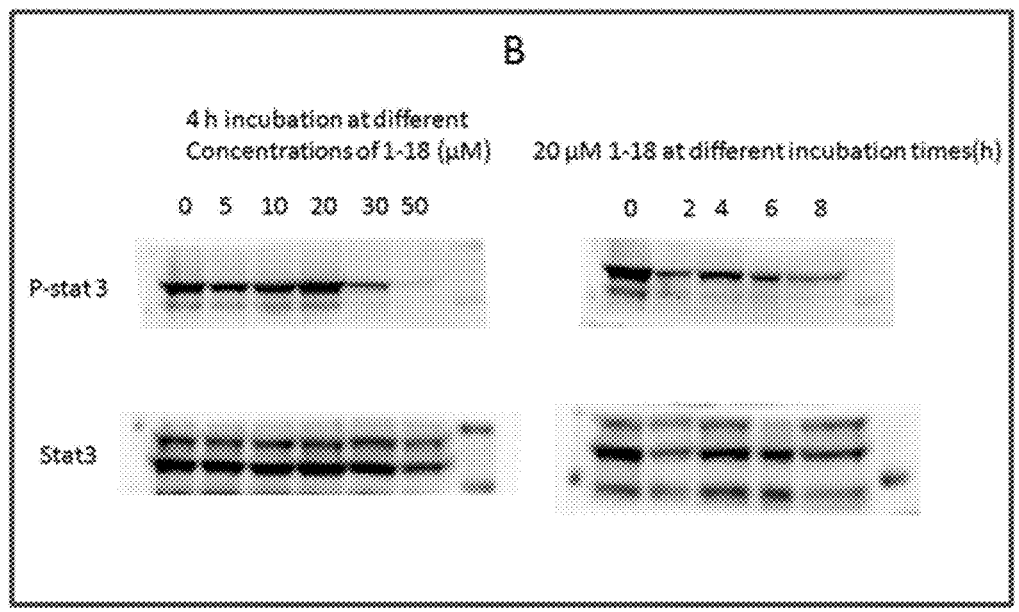

Compounds 1-10, 1-18 and 6-6 were screened for their abilities to modulate constitutive STAT3 activation in HepG2. Several immunoblots were run and the results of one representative attempt is given in FIG. 3. Interestingly, only 1-18 reduced p-STAT3 levels while 1-10 and 6-6 did not. 1-10 and 6-6 are structurally more alike (with regards to ring B substitution, both have $R_3=CF_3$) and their inability to reduce p-STAT levels, in contrast to the N-methylaminosulfonyl containing 1-18, may imply specific structural requirements for interaction with the signaling molecule.

Example 6

Solubility and PAMPA Permeability

Solubility and PAMPA permeability (Pe) are important physicochemical indicators of drug-like character. Determination of aqueous solubility was carried out on Multiscreen® Solubility filter plates (Millipore-MSSLBPC10) from Millipore Corporation (MA, USA). The protocol (PC2445EN00, Millipore Corporation) was followed. Pe determinations were carried out on MultiScreen-IP PAMPA assay (donor) plates (MAIPNTR10) and MultiScreen Receiver Plates (MATRNPS50) from Millipore Corporation (USA) with 1% lecithin (L-α-phosphatidylcholine from lyophilized powder of egg yolk, Sigma Aldrich, USA) in dodecane (ReagentPlus®, Sigma Aldrich, USA) as lipid barrier. Results are given in Table 10.

TABLE 10

Solubilities and Pe of 1-18 and 3-10 at different agitation times. Determinations were carried out at pH 7.4, mean (SD) of 3 independent determinations.

| | | Solubility (μM) | | Pe ($\times 10^{-6}$ cm/s) |
|---|---|---|---|---|
| 1-18 | 3 h | 8.85 (1.01) | 6 h | 18.3 (1.3) |
| | 24 h | 2.28 (0.18) | 16 h | 12.3 (0.7) |
| 3-10 | 3 h | 37.6 (7.6) | 6 h | 12.9 (0.4) |
| | 24 h | 6.32 (0.41) | 16 h | 5.95 (0.90) |

Both compounds do not have good solubilities. The decrease in solubility with agitation time is puzzling and may be due to E/Z interconversion. 1-18 has good permeability, with a Pe value that is close to that of the reference compound quinidine (represents a compound with moderate permeability). Its Pe showed a decline with time but still fall within the range of moderate permeability. 3-10 is more worrisome as its Pe declined by ½ with time. Solubilities and Pe of 1-10 and 6-6 are ongoing but they are not anticipated to have better solubilities in view of the presence of the lipophilic CF3 substituent on ring B.

What is claimed is:

1. A compound of general formula (I)

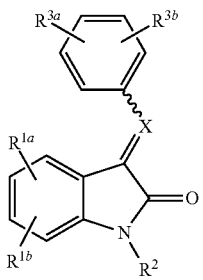

or a pharmaceutically acceptable salt thereof, wherein
$R^{1a}$ is hydrogen, halo or —O($C_{1-6}$ alkyl);
$R^{1b}$ is hydrogen or, when $R^{1a}$ is halo, $R^{1b}$ is halo or hydrogen;
$R^2$ is hydrogen or $C_{1-6}$ alkyl;
$R^{3a}$ is at the 3-position and is —O($C_{1-4}$ haloalkyl), —$SO_2$($C_{1-4}$ alkyl) or —$SO_2NR^{4a}R^{4b}$;
where each $R^{4a}$ and $R^{4b}$ is independently H or $C_{1-4}$ alkyl; and
$R^{3b}$ is hydrogen;
X is CH.

2. The compound of claim 1 wherein $R^{1a}$ is hydrogen, fluoro, chloro or —O($C_{1-4}$ alkyl).

3. The compound of claim 2 wherein:
$R^{1a}$ and $R^{1b}$ are both hydrogen; or
$R^{1a}$ is chloro, fluoro or methoxy and $R^{1b}$ is hydrogen; or
$R^{1a}$ and $R^{1b}$ are both chloro; or
$R^{1a}$ and $R^{1b}$ are both fluoro.

4. The compound of claim 1 wherein $R^{1b}$ is hydrogen and $R^{1a}$ is at the 5- or 6-position.

5. The compound of claim 4 wherein $R^{1a}$ is selected from the group consisting of chloro, fluoro or methoxy.

6. The compound of claim 1 wherein $R^{1a}$ and $R^{1b}$ are both halo and are at the 4- and 5-positions or at the 5- and 6-positions.

7. The compound of claim 6 wherein $R^{1a}$ and $R^{1b}$ are selected from the group consisting of 4,5-dichloro, 5,6-dichloro, 4,5-difluoro and 5,6-difluoro.

8. The compound of claim 1, wherein $R^2$ is hydrogen or methyl.

9. The compound of claim 1 wherein $R^{3a}$ is selected from the group consisting of —O($C_{1-2}$ haloalkyl), —$SO_2$—($C_{1-4}$ alkyl), —$SO_2NH_2$, —$SO_2NH$($C_{1-4}$ alkyl) and —$SO_2N(C_{1-2}$ alkyl$)_2$; and $R^{3b}$ is hydrogen.

10. The compound of claim 9 wherein $R^{3a}$ is selected from the group consisting of trifluoromethoxy, —$SO_2NH_2$, —$SO_2NHCH_3$, —$SO_2NH$(ethyl), —$SO_2NH$(n-propyl), —$SO_2NH$(isopropyl) and —$SO_2N(CH_3)_2$; and $R^{3b}$ is hydrogen.

11. The compound of claim 1 wherein $R^{1a}$ is 6-chloro or 6-fluoro; $R^{1b}$ is H; $R^{3b}$ is H; and $R^{3a}$ is selected from the group consisting of trifluoromethoxy, —$SO_2(C_{1-4}$ alkyl) and —$SO_2NR^{4a}R^{4b}$; where each $R^{4a}$ and $R^{4b}$ is independently H, methyl, ethyl, isopropyl or n-propyl.

12. The compound of claim 1 wherein $R^{1a}$ is 5-chloro or 5-fluoro; $R^{1b}$ is H; $R^{3b}$ is H; and $R^{3a}$ is selected from the group consisting of trifluoromethoxy, —$SO_2(C_{1-4}$ alkyl) and —$SO_2NR^{4a}R^{4b}$; where each $R^{4a}$ and $R^{4b}$ is independently H, methyl, ethyl, isopropyl or n-propyl.

13. The compound of claim 1 wherein $R^{1a}$ is 6-methoxy; $R^{1b}$ is H; $R^{3b}$ is H; and $R^{3a}$ is selected from the group consisting of trifluoromethoxy, —$SO_2(C_{1-4}$ alkyl) and —$SO_2NR^{4a}R^{4b}$; where each $R^{4a}$ and $R^{4b}$ is independently H, methyl, ethyl, isopropyl or n-propyl.

14. The compound of claim 1 wherein $R^{1a}$ and $R^{1b}$ are 4,5-difluoro, $R^{3b}$ is hydrogen and $R^{3a}$ is trifluoromethoxy —$SO_2(C_{1-4}$ alkyl) or —$SO_2NR^{4a}R^{4b}$; where each $R^{4a}$ and $R^{4b}$ is independently H, methyl, ethyl, isopropyl or n-propyl.

15. The compound of claim 1 wherein $R^{1a}$ and $R^{1b}$ are 5,6-difluoro, $R^{3b}$ is hydrogen and $R^{3a}$ is trifluoromethoxy —$SO_2(C_{1-4}$ alkyl) or —$SO_2NR^{4a}R^{4b}$; where each $R^{4a}$ and $R^{4b}$ is independently H, methyl, ethyl, isopropyl or n-propyl.

16. A compound of claim 1 selected from the group consisting of:
(E)-6-Chloro-3-(3-trifluoromethoxyl-benzylidene)indol-2-one (1-14);
(E)-6-Chloro-3-(3-methylsulfonyl-benzylidene)indol-2-one (1-16);
(E) 3-(6-Chloro-2-oxo-1,2-dihydro-indol-3-ylidenem-ethyl)-benzene-sulfonamide (1-17);
(E)-3-(6-Chloro-2-oxo-1,2-dihydro-indol-3-ylidenem-ethyl)-N-methyl-benzenesulfonamide (1-18);
(E) 3-(6-Chloro-2-oxo-1,2-dihydro-indol-3-ylidenem-ethyl)-benzonitrile (1-19)
(E)-3-(6-Chloro-2-oxo-1,2-dihydro-indol-3-ylidenem-ethyl)-N,N-dimethyl-benzenesulfonamide (1-20);
(E)-3-(6-Chloro-2-oxo-1,2-dihydro-indol-3-ylidenem-ethyl)-N-ethyl-benzenesulfonamide (1-22)
(E/Z)-3-(6-Chloro-2-oxo-1,2-dihydro-indol-3-ylidenem-ethyl)-N-propyl-benzenesulfonamide (1-23)
(E/Z)-3-(6-Chloro-2-oxo-1,2-dihydro-indol-3-ylidenem-ethyl)-N-isopropyl-benzenesulfonamide (1-24)
(E)-5-Chloro-3-(3-trifluoromethoxyl-benzylidene)indol-2-one (2-10);
(E)-5-Chloro-3-(3-methanesulfonylbenzylidene)indol-2-one (2-11);
(E/Z)-3-(5-Chloro-2-oxo-1,2-dihydro-indol-3-ylidenem-ethyl)-benzenesulfonamide (2-12);
(E)-3-(5-Chloro-2-oxo-1,2-dihydro-indol-3-ylidenem-ethyl)-N-methyl-benzenesulphonamide (2-14);
(E)-6-Fluoro-3-(3-trifluoromethoxyl-benzylidene)indol-2-one (3-8)
(E)-6-Fluoro-3-(3-methanesulfonylbenzylidene)indol-2-one (3-9);
(E)-3-(6-Fluoro-2-oxo-1,2-dihydro-indol-3-ylidenem-ethyl)-N-methyl-benzenesulphonamide (3-10);
(E)-3-(6-Fluoro-2-oxo-1,2-dihydro-indol-3-ylidenem-ethyl)-N-ethyl-benzenesulfonamide (3-11)
(E/Z)-3-(6-Fluoro-2-oxo-1,2-dihydro-indol-3-ylidenem-ethyl)-N-propyl-benzenesulfonamide (3-12)
(E)-3-(6-Fluoro-2-oxo-1,2-dihydro-indol-3-ylidenem-ethyl)-N-isopropyl-benzenesulfonamide (3-13)
(E)-5-Fluoro-3-(3-trifluoromethoxyl-benzylidene)-1,3-dihydro-indol-2-one (4-13);
(E)-5-Fluoro-3-(3-methanesulfonylbenzylidene)-1,3-dihydro-indol-2-one (4-14);
(E)-3-(5-Fluoro-2-oxo-1,2-dihydro-indol-3-ylidenem-ethyl)-N-methyl-benzenesulphonamide (4-16);

(E)-3-(6-Methoxy-2-oxo-1,2-dihydro-indol-3-ylidenemethyl)-N-methyl-benzenesulphonamide (5-8);
(Z)-4,5-Difluoro-3-(3-trifluoromethoxyl-benzylidene)-1,3-dihydro-indol-2-one (6-8)
(E/Z)-4,5-Difluoro-3-(3-methanesulfonylbenzylidene)-1,3-dihydro-indol-2-one (6-9);
(Z)-3-(4,5-Difluoro-2-oxo-1,2-dihydro-indol-3-ylidenemethyl)-N-methyl-benzenesulphonamide (6-10);
(E)-5,6-Difluoro-3-(3-trifluoromethoxyl-benzylidene)-1,3-dihydro-indol-2-one (7-8);
(E)-5,6-Difluoro-3-(3-methanesulfonylbenzylidene)-1,3-dihydro-indol-2-one (7-9);
(E)-3-(5,6-Difluoro-2-oxo-1,2-dihydro-indol-3-ylidenemethyl)-N-ethyl-benzenesulfonamide (7-10):
and pharmaceutically acceptable salts thereof.

17. A process for preparing a compound of general formula (I) as defined in claim 1 comprising:
reacting a compound of general formula (II)

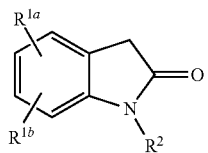

(II)

wherein $R^{1a}$, $R^{1b}$ and $R^2$ are as defined in claim 1 with an aldehyde of general formula (III)

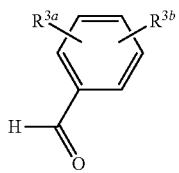

(III)

wherein $R^{3a}$ and $R^{3b}$ are as defined in claim 1.

18. A method for the treatment of liver carcinoma, hepatocellular carcinoma, lung cancer, atherosclerosis, arthritis, restenosis, abnormal angiogenesis and vasculogenesis, psoriasis, diabetes mellitus, and inflammation and slow wound healing rates, the method comprising administering to a patient in need of such treatment an effective amount of a compound according to claim 1.

19. A method for the treatment of a cancer selected from the group consisting of hepatocellular carcinoma, and lung cancer the method comprising administering to a patient in need of such treatment an effective amount of a compound according to claim 1.

20. A pharmaceutical composition comprising a compound according to claim 1 and a pharmaceutically acceptable excipient.

21. A pharmaceutical composition according to claim 20 which is adapted for oral, transdermal, buccal, nasal, sublingual or anal, intravenous or intramuscular administration.

* * * * *

UNITED STATES PATENT AND TRADEMARK OFFICE
CERTIFICATE OF CORRECTION

PATENT NO. : 8,877,946 B2  Page 1 of 1
APPLICATION NO. : 13/564179
DATED : November 4, 2014
INVENTOR(S) : Go et al.

It is certified that error appears in the above-identified patent and that said Letters Patent is hereby corrected as shown below:

In the Claims:

Claim 14, column 80, lines 14-15, "trifluoromethoxy –$SO_2(C_{1-4}$ alkyl)" should read – trifluoromethoxy, —$SO_2(C_{1-4}$ alkyl) –

Claim 15, column 80, lines 18-19, "trifluoromethoxy –$SO_2(C_{1-4}$ alkyl)" should read – trifluoromethoxy, —$SO_2(C_{1-4}$ alkyl) –

Claim 16, column 80, line 28, "(E)   3" should read – (E)-3 –

Claim 16, column 80, line 32, "(E)   3" should read – (E)-3 –

Claim 16, column 80, line 33, "(1-19)" should read – (1-19); –

Claim 16, column 80, line 37, "(1-22)" should read – (1-22); –

Claim 16, column 80, line 39, "(1-23)" should read – (1-23); –

Claim 16, column 80, line 41, "(1-24)" should read – (1-24); –

Claim 16, column 80, line 51, "(3-8)" should read – (3-8); –

Claim 16, column 80, line 57, "(3-11)" should read – (3-11); –

Claim 16, column 80, line 59, "(3-12)" should read – (3-12); –

Claim 16, column 80, line 61, "(3-13)" should read – (3-13); –

Claim 16, column 81, line 4, "(6-8)" should read – (6-8); –

Claim 16, column 81, line 14, "(7-10):" should read – (7-10); –

Claim 19, column 82, lines 20-21, "lung cancer the method comprising" should read – lung cancer, the method comprising –

Signed and Sealed this
Twenty-third Day of February, 2016

Michelle K. Lee
*Director of the United States Patent and Trademark Office*